United States Patent
Takemoto et al.

(10) Patent No.: US 10,520,518 B2
(45) Date of Patent: Dec. 31, 2019

(54) SPECIMEN ANALYZER AND SPECIMEN ANALYSIS METHOD

(71) Applicant: Sysmex Corporation, Kobe-shi, Hyogo (JP)

(72) Inventors: Seiji Takemoto, Kobe (JP); Takeshi Komoto, Kobe (JP); Hideki Hirayama, Kobe (JP); Takashi Yoshida, Kobe (JP); James Ausdenmoore, Elgin, IL (US)

(73) Assignee: SYSMEX CORPORATION, Kobe-shi (JP)

( * ) Notice: Subject to any disclaimer, the term of this patent is extended or adjusted under 35 U.S.C. 154(b) by 214 days.

(21) Appl. No.: 15/610,087

(22) Filed: May 31, 2017

(65) Prior Publication Data

US 2018/0348243 A1 Dec. 6, 2018

(51) Int. Cl.
  *G01N 35/00* (2006.01)
  *G01N 35/10* (2006.01)
  *G01N 33/80* (2006.01)

(52) U.S. Cl.
  CPC ....... *G01N 35/00663* (2013.01); *G01N 33/80* (2013.01); *G01N 35/00722* (2013.01); *G01N 35/1004* (2013.01); *G01N 2035/00673* (2013.01); *G01N 2035/00891* (2013.01)

(58) Field of Classification Search
  None
  See application file for complete search history.

(56) References Cited

U.S. PATENT DOCUMENTS

| | | |
|---|---|---|
| 6,635,488 B1 | 10/2003 | Saito et al. |
| 6,772,650 B2 | 8/2004 | Ohyama et al. |
| 6,938,502 B2 | 9/2005 | Tanoshima et al. |
| 8,474,692 B2 | 7/2013 | Mizumoto et al. |
| 8,790,577 B2 | 7/2014 | Mizumoto et al. |
| 8,967,459 B2 | 3/2015 | Mizumoto et al. |
| 9,297,819 B2 | 3/2016 | Ausdenmoore et al. |
| 9,317,653 B2 | 4/2016 | Ausdenmoore et al. |
| 9,395,378 B2 | 7/2016 | Mizumoto et al. |
| 2002/0060247 A1* | 5/2002 | Krishnaswamy .... A61B 5/0002 235/472.01 |
| 2006/0029520 A1 | 2/2006 | Tanoshima et al. |
| 2013/0023006 A1 | 1/2013 | Ausdenmoore et al. |
| 2013/0229352 A1* | 9/2013 | Tsutsumi ............... G06F 3/041 345/168 |

(Continued)

FOREIGN PATENT DOCUMENTS

| | | |
|---|---|---|
| JP | H06-027117 A | 2/1994 |
| JP | 2001-004634 A | 1/2001 |

(Continued)

*Primary Examiner* — Kathryn Wright
(74) *Attorney, Agent, or Firm* — Metrolex IP Law Group, PLLC

(57) ABSTRACT

This specimen analyzer includes: an analysis unit which analyzes a specimen collected from a subject; a manual input unit which receives an input of information by manual operation; an information read unit which receives an input of information by reading an information record section provided in a consumable; and a controller which does not permit an input of information on the consumable with the manual input unit, and permits an input of the information on the consumable with the information read unit.

16 Claims, 56 Drawing Sheets

(56) References Cited

U.S. PATENT DOCUMENTS

2015/0125938 A1    5/2015  Terashima et al.

FOREIGN PATENT DOCUMENTS

| JP | 2001-124781 A | 5/2001 |
| JP | 2003-083960 A | 3/2003 |
| JP | 2009-068979 A | 4/2009 |
| JP | 2012-073164 A | 4/2012 |
| JP | 2013-024880 A | 2/2013 |
| JP | 2013-024881 A | 2/2013 |
| JP | 2013-024882 A | 2/2013 |
| JP | 2014-145685 A | 8/2014 |
| JP | 2015-163904 A | 9/2015 |

* cited by examiner

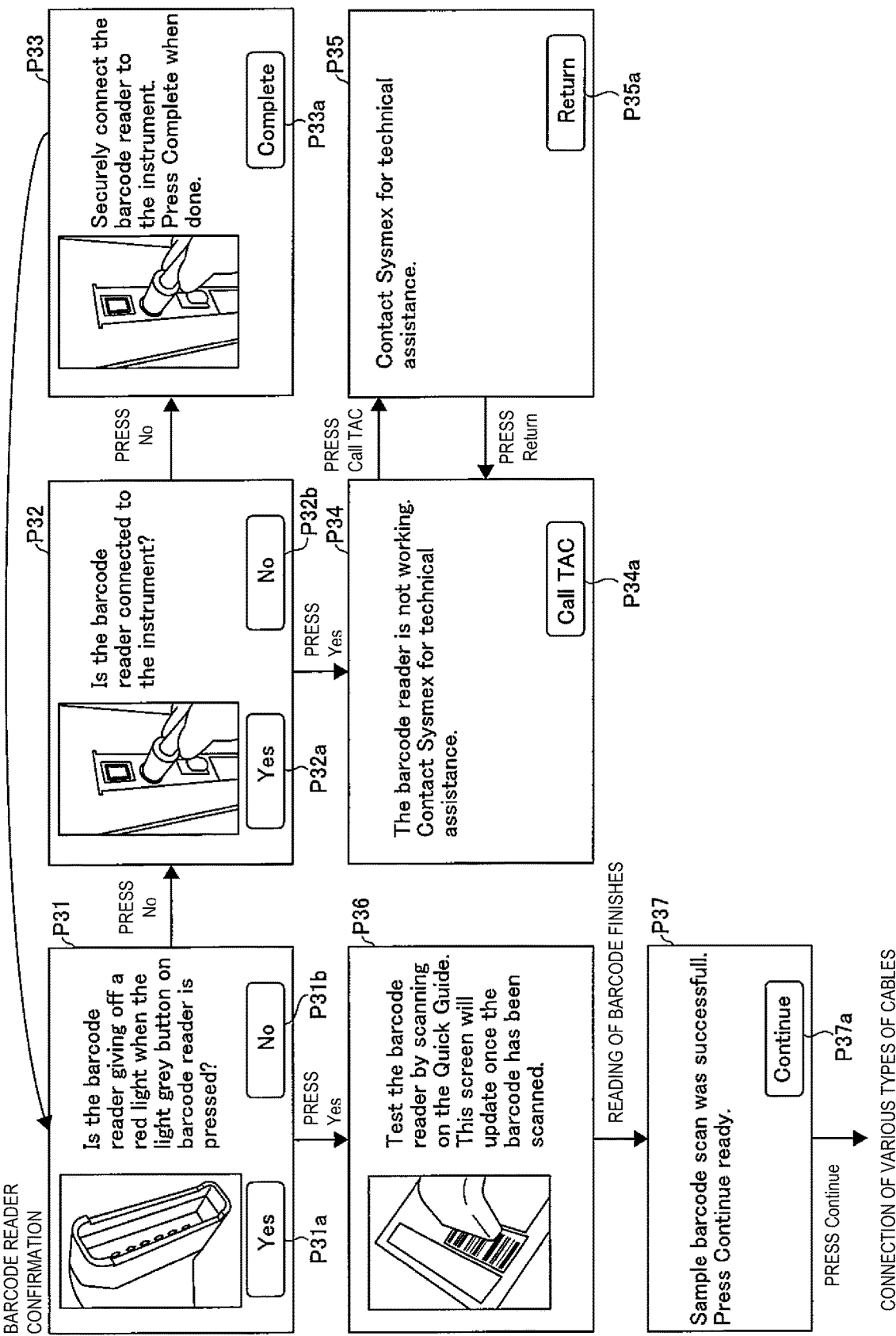

FIG. 14

CONNECTION OF VARIOUS TYPES OF CABLES

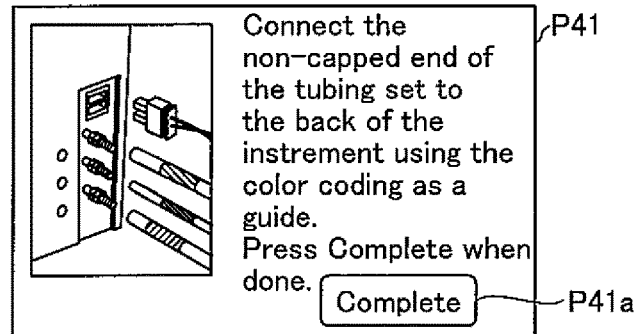

P41: Connect the non-capped end of the tubing set to the back of the instrument using the color coding as a guide. Press Complete when done. [Complete] — P41a ↓ PRESS Complete

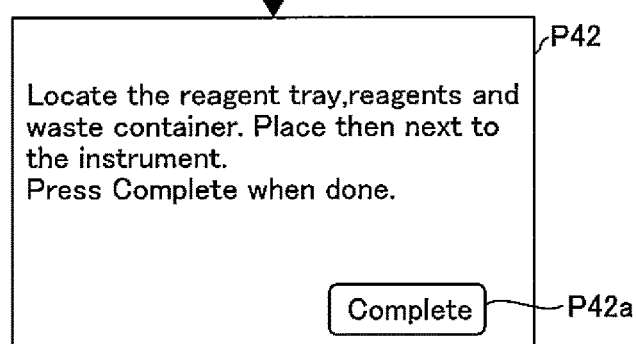

P42: Locate the reagent tray, reagents and waste container. Place then next to the instrument. Press Complete when done. [Complete] — P42a ↓ PRESS Complete

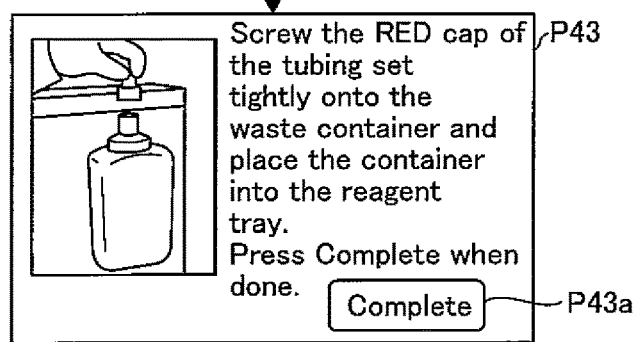

P43: Screw the RED cap of the tubing set tightly onto the waste container and place the container into the reagent tray. Press Complete when done. [Complete] — P43a ↓ PRESS Complete

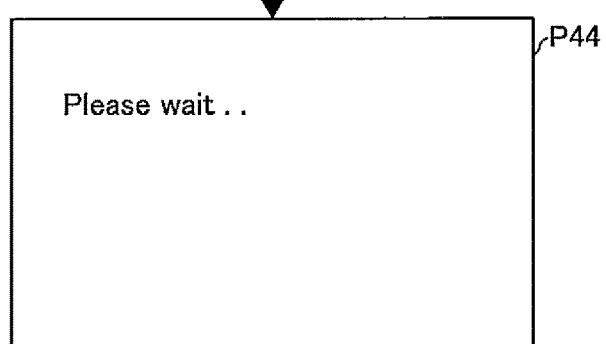

P44: Please wait..

↓

REAGENT SETTING

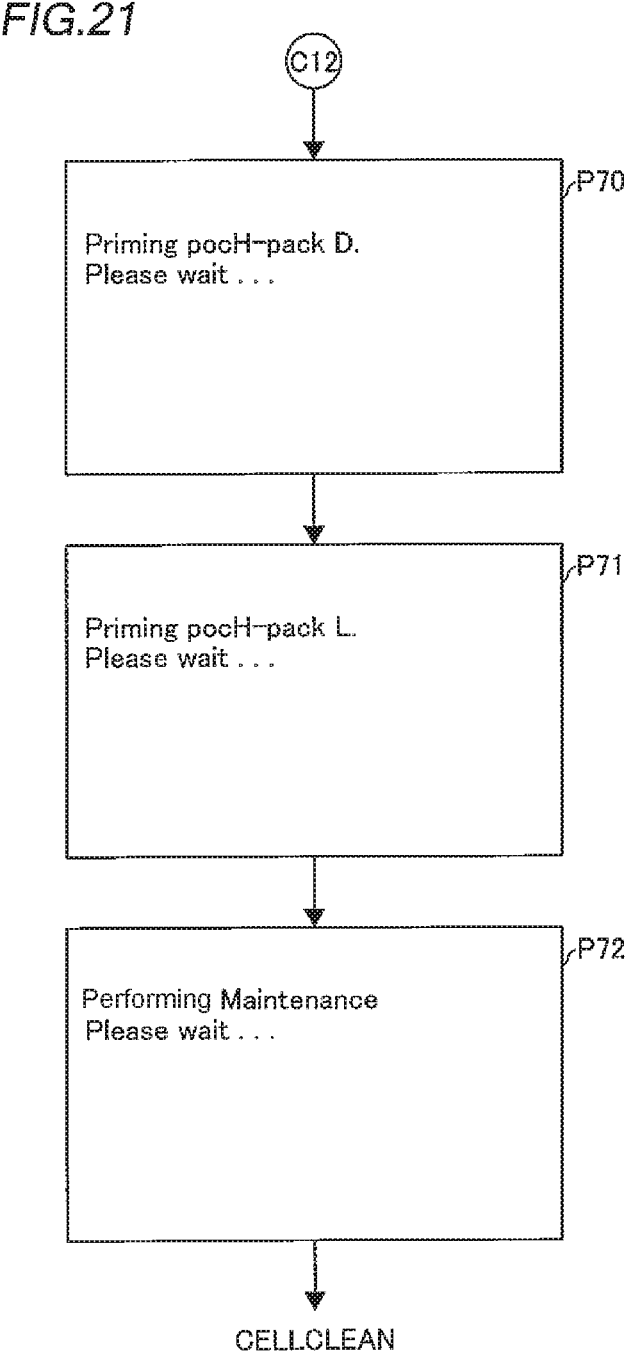

FIG.22

CELLCLEAN

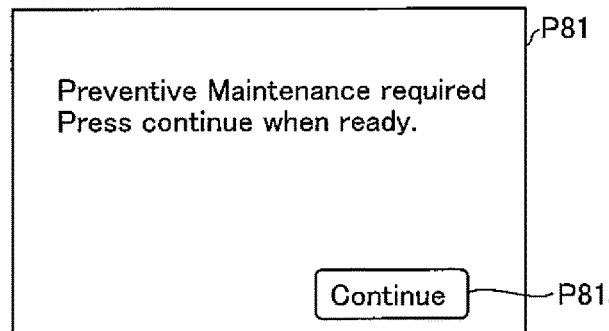

P81: Preventive Maintenance required Press continue when ready.
P81a: Continue

PRESS Continue

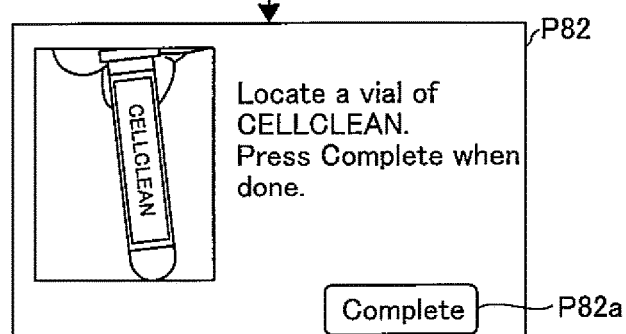

P82: Locate a vial of CELLCLEAN. Press Complete when done.
P82a: Complete

PRESS Complete

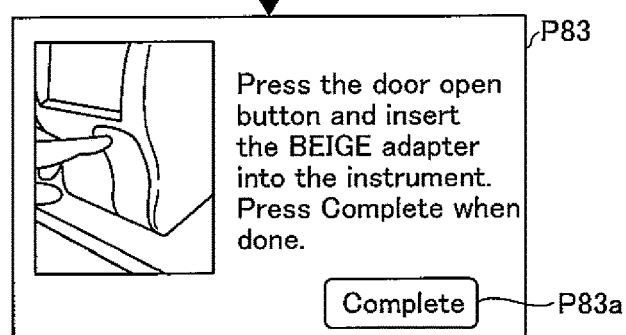

P83: Press the door open button and insert the BEIGE adapter into the instrument. Press Complete when done.
P83a: Complete PRESS Complete

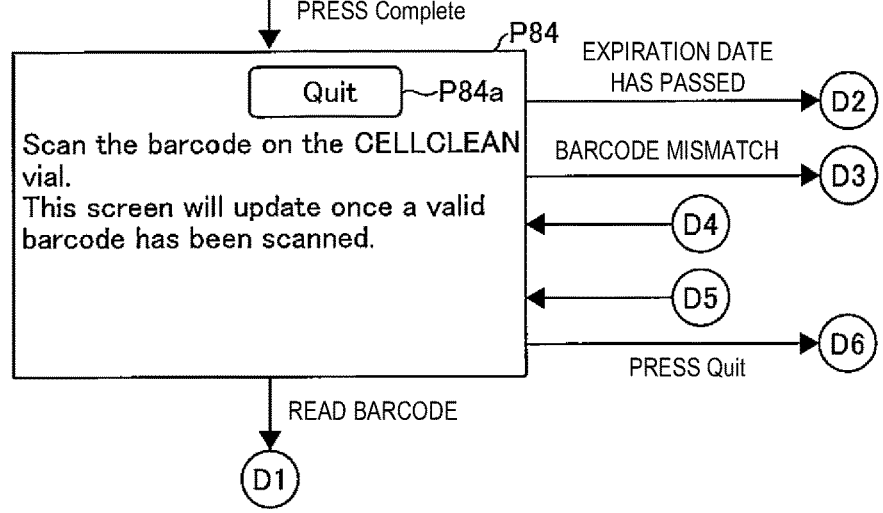

P84: Scan the barcode on the CELLCLEAN vial. This screen will update once a valid barcode has been scanned.
P84a: Quit EXPIRATION DATE HAS PASSED → D2
BARCODE MISMATCH → D3
← D4
← D5
PRESS Quit → D6

READ BARCODE ↓ D1

Auto Rinse

Remove Clog

FIG.45

Replace Pack-L

P181 pocH-pack L needs to be changed.
Press Continue when ready.

Continue — P181a

↓ PRESS Continue

SAME AS P51, P52, AND P172 TO P176

↓

SAMPLE MEASUREMENT

FIG.46

Prevent Maint

P191

Preventive Maintenance required.
Press Continue when ready.

Continue — P191a

↓ PRESS Continue

CELLCLEAN

↓

QC MEASUREMENT

↓

SAMPLE MEASUREMENT

FIG.49

```
┌─────────────────────────────────┐          300
│ Any Clinic                      │─── 301
│ Anytown, State                  │
├─────────────────────────────────┤
│ Instrument type XW100           │─── 302
│ Selial #                        │
├─────────────────────────────────┤
│ Date Feb 25, 2016               │─── 303
│ Time 08:00 AM                   │
├─────────────────────────────────┤
│ Operator                        │─── 304
├─────────────────────────────────┤
│ Patient ID      0000000         │─── 305
│ Patient DOB Jun 24, 1965        │─── 306
├─────────────────────────────────┤─── 307
│ WBC      ****       ALERT L     │
│ RBC      4.81 x 10⁶/μL          │
│ HGB      24.3 x g/dL  ALERT H   │
│ HCT      43.1 %                 │
│ PLT      ****       ALERT L     │
│                                 │
│ #Neut    ****       WBC Diff    │
│ %Neut    ****       WBC Diff    │
│                                 │
│ #Lymph   ****       WBC Diff    │
│ %Lymph   ****       WBC Diff    │
│                                 │
│ #OtherWBC ****      WBC Diff    │
│ %OtherWBC ****      WBC Diff    │
│                                 │
│ MCV      81.6 fL    Low         │
│                                 │
│ MCH      29.8 pg                │
│                                 │
│ MCHC     35.6 g/dL              │
│                                 │
│ RDW SD   41.9 fL                │
│                                 │
│ RDW CV   14. 0 %                │
│                                 │
│ MPV      10.0 fL                │
└─────────────────────────────────┘
       102a(102)   102b(102)
```

308

```
┌─────────────────────────────────┐
│ NOTES                           │
├─────────────────────────────────┤
│ RECOMMEND FURTHER TESTING       │─── 311
│                                 │
│ Potential ALERT Valve should be │─── 312
│ acted upon IMMEDIATELY          │
├─────────────────────────────────┤
│ Adult Reference Ranges          │
│ - - - - - - - - - - - - - - - - │
│                                 │
│ WBC        3.9 – 10.4 x 10³/μL  │
│ RBC        3.71 – 5.52 x 10⁶/μL │
│ HGB        10.9 – 16.7g/dL      │
│ HCT        32.5 – 49.4%         │
│ PLT        148 – 382 x 10³/μL   │
│ %Neut      46.4 – 76.9%         │
│ %Lymph     14.7 – 45.9%         │
│ %OtherWBC  3.2 – 16.9%          │
│ MCV        82.5 – 98.0 fL       │
│ MCH        26.1 – 32.8 pg       │
│ MCHC       30.7 – 35.9 g/dL     │
│ RDW SD     39.1 – 51.6 fL       │
│ RDW CV     11. 8 – 15.8 %       │
│ MPV        8.5 – 13.3 fL        │
├─────────────────────────────────┤
│ - - - End·Report - - -          │
└─────────────────────────────────┘
```

| | | 313 | 102a(102) 102b(102) |
|---|---|---|---|
| 300 | | | |
| | WBC | **** | ALERT L — 315 |
| 307 → | RBC | 4.81 x 10⁶/μL | |
| | HGB | 24.3 x g/dL | ALERT H — 315 |
| | HCT | 43.1 % | |
| | PLT | **** | ALERT L — 315 |
| 313 | | | |
| | #Neut | **** | WBC Diff |
| | %Neut | **** | WBC Diff |
| | #Lymph | **** | WBC Diff |
| | %Lymph | **** | WBC Diff — 102b(102) |
| | #OtherWBC | **** | WBC Diff |
| | %OtherWBC | **** | WBC Diff — 102b(102) |
| | MCV | 81.6 fL | Low — 314 |
| | MCH | 29.8 pg | — 102a(102) |
| | MCHC | 35.6 g/dL | |
| | RDW SD | 41.9 fL | |
| | RDW CV | 14.0 % | |
| | MPV | 10.0 fL | |

FIG.51

| ANALYSIS RESULTS | | | PERMISSION/ PROHIBITION OF OUTPUT | PRINT EMBODIMENTS WHEN OUTPUT IS PROHIBITED |
|---|---|---|---|---|
| OUTSIDE FIRST DETERMINATION RANGE | | | | |
| | | NUMERICAL INFORMATION | OUTPUT PROHIBITED | SUBSTITUTE INDICATION |
| | | CONTENT OF ERROR | OUTPUT PROHIBITED | NOT DISPLAYED |
| WITHIN NORMAL RANGE (Reference Range) | | | | |
| | | NUMERICAL INFORMATION | OUTPUT PERMITTED | — |
| | | CONTENT OF ERROR | — | — |
| WITHIN FIRST ERRONEOUS RANGE (High or Low) | | | | |
| | INITIAL TEST | NUMERICAL INFORMATION | OUTPUT PROHIBITED | PROHIBIT OUTPUT OF PRINTED MATTER |
| | | CONTENT OF ERROR | OUTPUT PROHIBITED | |
| | RETEST RESULTS DETERMINED AS MISMATCHED | NUMERICAL INFORMATION | OUTPUT PROHIBITED | SUBSTITUTE INDICATION |
| | | CONTENT OF ERROR | OUTPUT PERMITTED | — |
| | RETEST RESULTS DETERMINED AS MISMATCHED | NUMERICAL INFORMATION | OUTPUT PERMITTED | — |
| | | CONTENT OF ERROR | OUTPUT PERMITTED | — |
| WITHIN SECOND ERRONEOUS RANGE (ALERT H or ALERT L) | | | | |
| | WITHIN SECOND DETERMINATION RANGE | NUMERICAL INFORMATION | OUTPUT PROHIBITED | SUBSTITUTE INDICATION |
| | | CONTENT OF ERROR | OUTPUT PERMITTED | — |
| | OUTSIDE SECOND DETERMINATION RANGE | NUMERICAL INFORMATION | OUTPUT PERMITTED | — |
| | | CONTENT OF ERROR | OUTPUT PERMITTED | — |
| CONTENT OF ERROR | | | | |
| | | NUMERICAL INFORMATION | OUTPUT PROHIBITED | SUBSTITUTE INDICATION |
| | | CONTENT OF ERROR | OUTPUT PERMITTED | — |

FIG.52

| | LINEARITY GUARANTEE RANGE |
|---|---|
| WBC | 1.0 – 99.9 ($\times 10^3/\mu L$) |
| RBC | 0.30 – 7.00 ($\times 10^6/\mu L$) |
| HGB | 1 – 250 (g/L) |
| HCT | 10.0 – 60.0 (%) |
| PLT | 10 – 999 ($\times 10^3/\mu L$) |

350

| | Pediatric (≥2 to <12 years of age) | | | | |
|---|---|---|---|---|---|
| | ALERT LOW | Low | Reference Range | High | ALERT HIGH |
| WBC($\times 10^3/\mu$L) | 1.0-2.9 | 3.0-4.7 | 4.8-13.5 | 13.6-50.0 | 50.1-63.2 |
| RBC($\times 10^6/\mu$L) | – | 0.30-4.10 | 4.20-5.40 | 5.50-7.00 | – |
| HGB(g/dL) | 0.1-9.9 | 10.0-10.4 | 10.5-16.0 | 16.1-24.0 | 24.1-25.0 |
| HCT (%) | 10.0-24.9 | 25.0-28.9 | 29.0-48.0 | 48.1-60.0 | – |
| PLT ($\times 10^3/\mu$L) | 10-99 | 100-162 | 163-369 | 370-999 | – |
| %Neut (%) | – | 0.0-34.9 | 35.0-76.0 | 76.1-100.0 | – |
| #Neut ($\times 10^3/\mu$L) | – | 1.0-1.8 | 1.9-8.6 | 8.7-63.2 | – |
| %Lymph (%) | – | 0.0-19.9 | 20.0-54.0 | 54.1-100.0 | – |
| #Lymph ($\times 10^3/\mu$L) | – | – | 1.0-7.2 | 7.3-63.2 | – |
| %OtherWBC (%) | – | – | 0.0-19.0 | 19.1-100.0 | – |
| #OtherWBC($\times 10^3/\mu$L) | – | – | 1.0-2.2 | 2.3-63.2 | – |
| MCV (fL) | – | 0.0-75.9 | 76.0-99.0 | 99.1-999.9 | – |
| MCH (pg) | – | 0.0-25.5 | 25.6-32.2 | 32.3-999.9 | – |
| MCHC (g/dL) | – | 0.0-32.1 | 32.2-36.5 | 36.6-999.9 | – |
| RDW CV (%) | – | 0.0-35.0 | 35.1-46.1 | 46.2-100.0 | – |
| RDW SD(fL) | – | 0.0-11.5 | 11.6-14.4 | 14.5-250.0 | – |
| MPV (fL) | – | 0.0-9.3 | 9.4-12.4 | 12.5-40.0 | – |

360(373)　372　371　372　373

| | Adolescents (≥12 to <21 years of age) | | | | |
|---|---|---|---|---|---|
| | ALERT LOW | Low | Reference Range | High | ALERT HIGH |
| WBC(×10³/μL) | 1.0-2.9 | 3.0-4.7 | 4.8-10.8 | 10.9-50.0 | 50.1-63.2 |
| RBC(×10⁶/μL) | – | 0.30-4.10 | 4.20-6.10 | 6.20-7.00 | – |
| HGB(g/dL) | 0.1-9.9 | 10.0-11.9 | 12.0-18.0 | 18.1-24.0 | 24.1-25.0 |
| HCT (%) | 10.0-24.9 | 25.0-36.9 | 37.0-52.0 | 52.1-60.0 | – |
| PLT (×10³/μL) | 10-99 | 100-162 | 163-369 | 370-999 | – |
| %Neut (%) | – | 0.0-39.9 | 40.0-80.0 | 80.1-100.0 | – |
| #Neut (×10³/μL) | – | 1.0-1.8 | 1.9-8.6 | 8.7-63.2 | – |
| %Lymph (%) | – | 0.0-14.9 | 15.0-40.0 | 40.1-100.0 | – |
| #Lymph (×10³/μL) | – | – | 1.0-3.9 | 4.0-63.2 | – |
| %OtherWBC (%) | – | – | 0.0-19.0 | 19.1-100.0 | – |
| #OtherWBC(×10³/μL) | – | – | 1.0-2.0 | 2.1-63.2 | – |
| MCV (fL) | – | 0.0-79.9 | 80.0-99.0 | 99.1-999.9 | – |
| MCH (pg) | – | 0.0-25.5 | 25.6-32.2 | 32.3-999.9 | – |
| MCHC (g/dL) | – | 0.0-32.1 | 32.2-36.5 | 36.6-999.9 | – |
| RDW CV (%) | – | 0.0-35.0 | 35.1-46.1 | 46.2-100.0 | – |
| RDW SD(fL) | – | 0.0-11.5 | 11.6-14.4 | 14.5-250.0 | – |
| MPV (fL) | – | 0.0-9.3 | 9.4-12.4 | 12.5-40.0 | – |

|  | Adult (≥21 years of age) | | | | |
|---|---|---|---|---|---|
|  | ALERT LOW | Low | Reference Range | High | ALERT HIGH |
| WBC (×10³/μL) | 1.0–2.9 | 3.0–3.8 | 3.9–10.4 | 10.5–50.0 | 50.1–63.2 |
| RBC (×10⁶/μL) | – | 0.30–3.70 | 3.71–5.52 | 5.53–7.00 | – |
| HGB (g/dL) | 0.1–9.9 | 10.0–10.8 | 10.9–16.7 | 16.8–24.0 | 24.1–25.0 |
| HCT (%) | 10.0–24.9 | 25.0–32.4 | 32.5–49.4 | 49.5–60.0 | – |
| PLT (×10³/μL) | 10–99 | 100–147 | 148–382 | 383–999 | – |
| %Neut (%) | – | 0.0–46.3 | 46.4–76.9 | 77.0–100.0 | – |
| #Neut (×10³/μL) | – | 1.0–2.1 | 2.2–7.1 | 7.2–63.2 | – |
| %Lymph (%) | – | 0.0–14.6 | 14.7–45.9 | 46.0–100.0 | – |
| #Lymph (×10³/μL) | – | – | 1.0–3.4 | 3.5–63.2 | – |
| %OtherWBC (%) | – | 0.0–3.1 | 3.2–16.9 | 17.0–100.0 | – |
| #OtherWBC (×10³/μL) | – | – | 1.0–1.2 | 1.3–63.2 | – |
| MCV (fL) | – | 0.0–82.4 | 82.5–98.0 | 98.1–999.9 | – |
| MCH (pg) | – | 0.0–26.0 | 26.1–32.8 | 32.9–999.9 | – |
| MCHC (g/dL) | – | 0.0–30.6 | 30.7–35.9 | 36.0–999.9 | – |
| RDW CV (%) | – | 0.0–39.0 | 39.1–51.6 | 51.7–100.0 | – |
| RDW SD (fL) | – | 0.0–11.7 | 11.8–15.8 | 15.8–250.0 | – |
| MPV (fL) | – | 0.0–8.4 | 8.5–13.3 | 13.4–40.0 | – |
|  | 360(373) | 372 | 371 | 372 | 373 |

FIG.56

```
300 →        313   313    102
             WBC   ****         ALERT L  ---- 315
             RBC   4.81 x 10⁶/μL
             HGB   ****         ALERT H  ---- 315
307 →        HCT   43.1 %
             PLT   ****         ALERT L  ---- 315
        313

#Neut    ****      WBC Diff
             %Neut    ****      WBC Diff

#Lymph   ****      WBC Diff
             %Lymph   ****      WBC Diff

#OtherWBC ****     WBC Diff
             %OtherWBC ****     WBC Diff
```

FIG.57

```
             RBC      4.81 x 10⁶/μL  ← ---- 102
300 →        HCT      43.1 %         ← ---- 102

MCV      81.6 fL        Low  ---- 314

307 →        MCH      29.8 pg

MCHC     35.6 g/dL

RDW SD   41.9 fL

RDW CV   14.0 %

MPV      10.0 fL

NOTES
             ----------------------------------
             RECOMMEND FURTHER TESTING ← ---- 311

308 →        Potential ALERT Valve should be ← ---- 312
             acted upon IMMEDIATELY
```

FIG.58

| ANALYSIS RESULTS | | FIRST MODIFIED EXAMPLE | SECOND MODIFIED EXAMPLE |
|---|---|---|---|
| OUTSIDE FIRST DETERMINATION RANGE | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PROHIBITED | NOT DISPLAYED |
| WITHIN NORMAL RANGE (Reference Range) | | | |
| | NUMERICAL INFORMATION | OUTPUT PERMITTED | OUTPUT PERMITTED |
| | CONTENT OF ERROR | — | — |
| WITHIN FIRST ERRONEOUS RANGE (High or Low) | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PERMITTED | NOT DISPLAYED |
| WITHIN SECOND ERRONEOUS RANGE (= WITHIN SECOND DETERMINATION RANGE) (ALERT H or ALERT L) | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PERMITTED | NOT DISPLAYED |
| FRACTIONATION ERROR | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PERMITTED | NOT DISPLAYED |

SPECIMEN ANALYZER AND SPECIMEN ANALYSIS METHOD

BACKGROUND

The invention relates to a specimen analyzer and a specimen analysis method.

Consumables such as a reagent are used in a specimen analyzer. Since it is necessary to use reagents of appropriate kinds and quality in order to obtain correct measurement results, consumables are managed by inputting information on the consumables prior to use in the analyzer.

Japanese Patent Application Publication No. 2009-68979 discloses a specimen analyzer which includes a keyboard to input information by manual operation, and a barcode reader which receives barcode read information. This specimen analyzer of Japanese Patent Application Publication No. 2009-68979 is capable of inputting information on consumables such as a reagent with both the keyboard and the barcode reader.

Here, a specimen analyzer intended to be used by a user with insufficient expertise and test skills is required to be simply operated while preventing mistakes and the like. However, the specimen analyzer of Japanese Patent Application Publication No. 2009-68979 is capable of inputting information on consumables with both the keyboard and the barcode reader, and this good usability which enables inputting with the two input units may conversely cause trouble in the form of input mistakes with the keyboard.

SUMMARY

The invention is aimed at appropriately managing consumables such as a reagent.

Specimen analyzer (100) according to a first aspect of the invention includes: analysis unit (10) which analyzes a specimen collected from a subject; manual input unit (20) which receives an input of information by manual operation; information read unit (30) which receives an input of information by reading information record section (51) provided in consumable (50); and controller (40) which does not permit an input of information on the consumable with manual input unit (20), but permits an input of the information on the consumable with information read unit (30).

As described above, specimen analyzer (100) according to the first aspect includes controller (40) which does not permit the input of information on the consumable with manual input unit (20), but permits an input of the information on the consumable with information read unit (30). This makes it possible to prevent a situation where the information on the consumables is mistakenly inputted due to an input mistake with manual input unit (20). Hence, it is possible to appropriately manage consumables such as a reagent. As a result, input mistakes and inappropriate use of consumables (50) are prevented, enabling appropriate consumable management.

It is preferable that above-described specimen analyzer (100) according to the first aspect include display unit (131) which displays information, and controller (40) perform control of causing display unit (131) to display how to input the information on the consumable. Such a configuration makes it possible to input the information on the consumable in accordance with the display of display unit (131), facilitating input operation without mistakes.

In this case, it is preferable that controller (40) perform control of causing display unit (131) to display an instruction prompting to input the information on the consumable with information read unit (30). Such a configuration makes it possible to guide the user to read the information on the consumable with information read unit (30). Hence, the user can easily input the information on the consumable.

In the above-described configuration of specimen analyzer (100) which includes display unit (131), it is preferable that controller (40) perform control of causing display unit (131) to display a message based on a determination as to whether or not the inputted information is appropriate. Such a configuration makes it possible to prevent use of inappropriate consumable (50) because information on the inappropriateness is displayed as a message if consumable (50) is inappropriate. Also, it is possible to prompt to use the appropriate consumable by displaying the reason for inappropriateness.

In this case, it is preferable that controller (40) perform control of acquiring an expiration date of consumable (50) based on the information on the consumable, and causing display unit (131) to display a message based on a determination as to whether or not the expiration date has passed. Such a configuration makes it possible to prevent use of expired consumable (50), which can prompt to use a more appropriate consumable.

In above-described specimen analyzer (100) which causes display unit (131) to display a message based on an appropriateness determination, it is preferable that consumable (50) include a disposable consumable, and if information record section (51) of disposable consumable (50) is read again after use of the disposable consumable, controller (40) perform control of not permitting use of consumable (50), and causing display unit (131) to display an error message. Such a configuration makes it possible to prevent a situation where disposable consumable (50) is used again, which can prompt to use a more appropriate consumable.

In above-described specimen analyzer (100) which causes display unit (131) to display a message based on an appropriateness determination, it is preferable that controller (40) perform control of acquiring whether or not consumable (50) is usable based on the information on the consumable, and causing display unit (131) to display an error message in a case where consumable (50) is unusable. Such a configuration makes it possible to prevent a situation where, for example, unusable consumables (50) such as consumables (50) of different types are set and used.

In above-described specimen analyzer (100) according to the first aspect, it is preferable that information read unit (30) receive an input of the information on each consumable by reading information record section (51) provided in consumable (50). Such a configuration makes it possible to reliably input information for each of consumables (50) when using more than one consumable (50).

It is preferable that the above-described specimen analyzer (100) according to the first aspect include communication unit (145) which is capable of communicating with external server (200), and controller (40) perform control of causing communication unit (145) to transmit the information on the consumable inputted with information read unit (30) to server (200). Such a configuration makes it possible to manage consumable (50) with external server (200), enabling more appropriate and easier management of consumable (50).

In this case, it is preferable that controller (40) do not permit inputting of the information on the consumable when it is impossible to connect to server (200) via communication unit (145). Such a configuration makes it possible to reliably manage consumable (50) with external server (200)

because placement or replacement of consumable (50) is not allowed when it is impossible to connect to server (200).

In the above-described configuration of specimen analyzer (100) which includes communication unit (145), it is preferable that controller (40) permit use of consumable (50) if the information on the consumable inputted with information read unit (30) is registered in server (200). Such a configuration makes it possible to effectively prevent use of inappropriate consumable (50).

In this case, it is preferable that controller (40) permit use of consumable (50) if a lot number as the information on the consumable is registered in server (200). Such a configuration makes it possible to more easily manage consumable (50) by managing the lot number of consumable (50) with server (200).

In above-described specimen analyzer (100) according to the first aspect, it is preferable that controller (40) do not shift to a next process concerning placement or replacement of consumable (50) unless the information on the consumable is input with information read unit (30). Such a configuration makes it possible to advance the processing concerning the placement or replacement of consumable (50) after inputting information to determine whether or not consumable (50) is an appropriate one. Hence, it is possible to reliably place or replace appropriate consumable (50).

In this case, it is preferable that the analyzer include display unit (131) which displays information, and controller (40) perform control of causing display unit (131) not to shift a screen of display unit (131) concerning placement or replacement of consumable (50) to a next screen unless the information on the consumable is input with information read unit (30). Such a configuration makes it possible to effectively prevent placement or replacement of inappropriate consumable (50) because a screen to advance placement or replacement of consumable (50) is not displayed until the information on the consumable is input with information read unit (30).

In above-described specimen analyzer (100) according to the first aspect, it is preferable that the information on the consumable includes at least one of a type, an expiration date, a lot number, and a serial number of consumable (50). Such a configuration makes it possible to appropriately manage consumable (50) to be used based on at least one of the type, the expiration date, the lot number, and the serial number of consumable (50).

In above-described specimen analyzer (100) according to the first aspect, it is preferable that analysis unit (10) analyzes the specimen by use of consumable (50). Such a configuration makes it possible to accurately analyze the specimen because appropriately managed consumable (50) is used for analysis.

In above-described specimen analyzer (100) according to the first aspect, it is preferable that the specimen is blood, and analysis unit (10) analyzes the number of blood cells and a concentration of a component contained in the blood. To be more specific, specimen analyzer (100) is a blood cell counting apparatus. The blood cell counting apparatus counts the number of blood cells contained in a predetermined volume of a blood specimen. The analysis results of the blood cell counting apparatus can include analysis values such as the number of cell components such as various blood cells and platelets, a measurement value of e.g. a concentration of a component in blood, ratios of blood cells based on the measured values, an average volume, and a distribution width. The blood cell counting apparatus performs some of the blood tests widely used in laboratory medicine. The analysis results of the blood cell counting apparatus are important in the field of laboratory medicine because they are related to various types of diseases. For this reason, the invention, which is capable of appropriately managing consumables such as a reagent, is suitably applied to blood cell counting apparatuses.

In above-described specimen analyzer (100) according to the first aspect, it is preferable that consumable (50) include at least one of a reagent used for analysis, a quality control sample, and a cleaning liquid. Such a configuration makes it possible to input information on the reagent used for analysis, the quality control sample, or the cleaning liquid without mistakes.

In above-described specimen analyzer (100) according to the first aspect, it is preferable that information read unit (30) include a barcode reader. Such a configuration makes it possible to easily receive an input of the information on the consumable using the barcode reader.

A specimen analysis method according to a second aspect of the invention includes: inputting information on a consumable by causing information read unit (30) to read information record section (51) provided in consumable (50), and placing consumable (50) or replacing an old one with consumable (50); analyzing a specimen collected from a subject; and rejecting reception of the information on the consumable until the information on the consumable is input with information read unit (30).

As described above, the specimen analysis method according to the second aspect does not receive the information on the consumable until the information on the consumable is input with information read unit (30). This makes it possible to prevent a situation where the information on the consumables is mistakenly inputted due to an input mistake with manual input unit (20) and the like. Hence, it is possible to provide a specimen analysis method which can appropriately manage consumables such as a reagent. As a result, input mistakes and inappropriate use of consumables (50) are prevented, enabling appropriate consumable management.

Specimen analyzer (100) according to a third aspect of the invention includes: analysis unit (10) which analyzes a specimen collected from a subject; an input unit which receives an input of information on a consumable; communication unit (145) which is capable of transmitting the information on the consumable inputted with the input unit to external server (200); and controller (40) which allows analysis unit (10) to analyze the specimen if connection is established between server (200) and communication unit (145).

As described, specimen analyzer (100) according to the third aspect includes communication unit (145) which is capable of transmitting the information on the consumable inputted with the input unit to external server (200), and controller (40) which allows analysis unit (10) to analyze the specimen under a condition that connection be established between server (200) and communication unit (145). This makes it possible to manage consumable (50) with external server (200), enabling appropriate management of consumables such as a reagent.

In above-described specimen analyzer (100) according to the third aspect, it is preferable that the input unit include information read unit (30) which reads information record section (51) provided in consumable (50). Such a configuration makes it possible to easily input the information on the consumable with information read unit (30).

BRIEF DESCRIPTION OF DRAWINGS

FIG. 13 is a diagram illustrating a display example for barcode reader confirmation;

FIG. 14 is a diagram illustrating a display example for connecting various types of tubes;

FIG. 21 is a diagram illustrating display example 7 for setting a reagent;

FIG. 22 is a diagram illustrating display example 1 for cleaning by CELLCLEAN;

FIG. 45 is a diagram illustrating display example 5 for maintenance;

FIG. 46 is a diagram illustrating display example 6 for maintenance;

FIG. 49 is a diagram illustrating an example of print content of printed sheet;

FIG. 50 is a diagram for explaining a result displaying section of the printed sheet;

FIG. 51 is a diagram for explaining rules of outputting analysis results on the printed sheet;

FIG. 52 is a diagram for explaining first determination ranges;

FIG. 55 is a diagram for explaining numerical ranges for evaluating analysis results for an adult;

FIG. 56 is a diagram for explaining a first modification of a printing embodiment of the analysis results;

FIG. 57 is a diagram for explaining a second modification of the printing embodiment of the analysis results;

FIG. 58 is a diagram for explaining first and second modifications of the rules of outputting the analysis results.

DETAILED DESCRIPTION

Hereinafter, embodiments are described based on the drawings.

[Overview of Specimen Analyzer]

Figure 1:
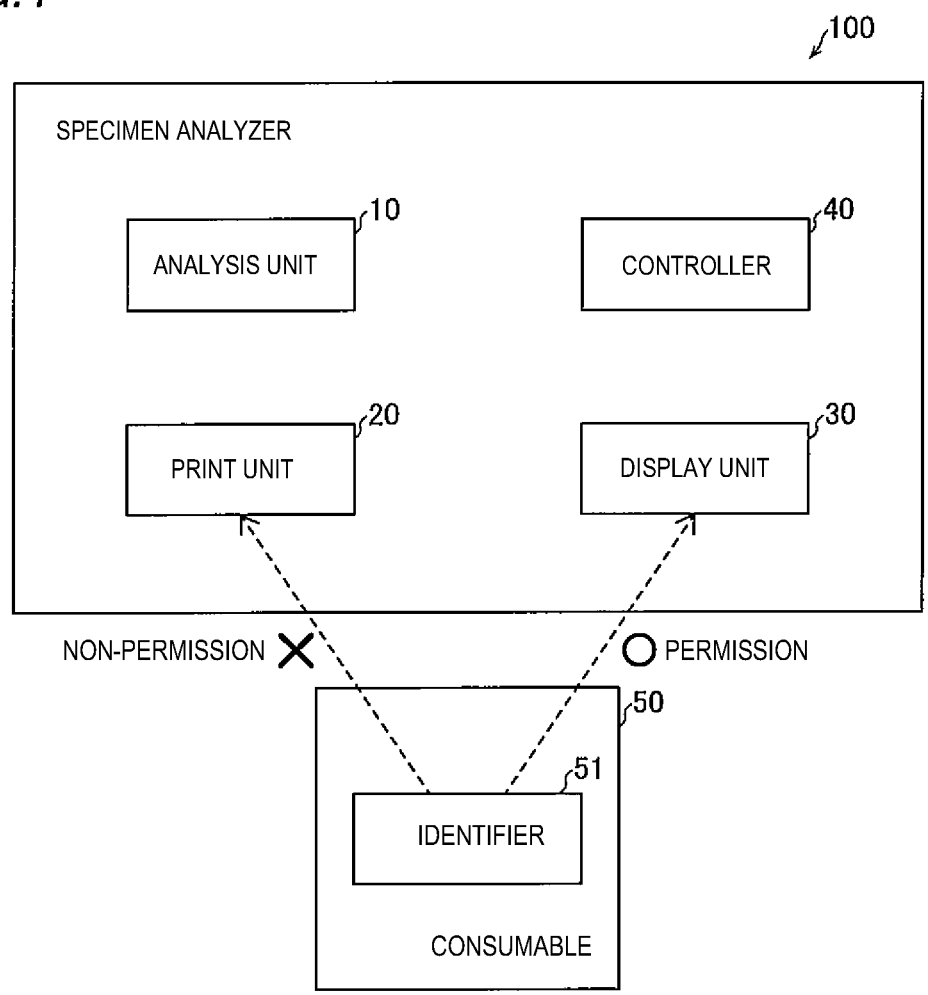
FIG. 1 is a diagram for explaining an overview of a specimen analyzer.

With reference to FIG. 1, an overview of specimen analyzer 100 according to an embodiment is described.

Specimen analyzer 100 according to the embodiment is an analysis apparatus for analyzing a specimen collected from a subject. As illustrated in FIG. 1, specimen analyzer 100 includes analysis unit 10, manual input unit 20, information read unit 30, and controller 40.

The specimen is blood of the subject, for example. Note that the specimen may be, for example, a body fluid other than urine and blood of the subject. Also, the specimen may be, for example, part of the tissue or a cell of the subject. In addition, the specimen may be, for example, DNA or RNA. Specimen analyzer 100 is, for example, an analysis apparatus which analyzes blood. For example, specimen analyzer 100 is a blood cell counting apparatus. Here, specimen analyzer 100 may be an analysis apparatus which analyzes a body fluid other than urine and blood of the subject. Moreover, specimen analyzer 100 may be an analysis apparatus which analyzes, for example, part of the tissue or a cell of the subject, DNA, or RNA.

Analysis unit 10 analyzes the specimen collected from the subject. Analysis unit 10 includes, for example, a controller which includes a CPU and a memory. Analysis unit 10 analyzes the specimen on the basis of measurement results obtained by measuring the specimen. In addition, analysis unit 10 is configured to analyze the specimen with use of consumables 50.

Manual input unit 20 receives inputs of information by manual operation. Manual input unit 20 includes, for example, a touch panel, a keyboard, and a mouse. Manual input unit 20 receives, for example, inputs of information on the subject. Also, manual input unit 20 receives, for example, inputs of the information on the user. In addition, manual input unit 20 receives inputs of the information on the operation of specimen analyzer 100.

Information read unit 30 reads information record section 51 provided in each of consumables 50, and receives inputs of information. Information read unit 30 includes, for example, a barcode reader and an RFID reader. Information read unit 30 receives inputs of the information on the consumables. To be more specific, information read unit 30 receives inputs of information on the consumables by reading information record section 51 provided in each of consumables 50. Consumables 50 are placed or replaced based on the inputs of the information on the consumables by information read unit 30.

Controller 40 is configured to control the units of specimen analyzer 100. Controller 40 includes, for example, a CPU and a memory. Controller 40 does not permit manual input unit 20 to input the information on the consumables, but permits information read unit 30 to input the information on the consumables. To be more specific, only information read unit 30 is permitted to input the information on the consumables. Moreover, the analysis of the specimen does not become ready if information read unit 30 does not input the information on the consumables. Furthermore, the information on the consumables is not received until the information on the consumables is input with information read unit 30. This makes it possible to prevent a situation where the information on the consumables is mistakenly inputted due to an input mistake with manual input unit 20. Hence, it is possible to appropriately manage consumables 50 such as a reagent. As a result, input mistakes and inappropriate use of consumables 50 are prevented, enabling appropriate consumable management. For example, information read unit 30 is capable of reading even a code with many digits fast and accurately compared to the inputting by manual input unit 20.

Consumables 50 are consumables used for specimen analyzer 100. Consumables 50 include, for example, a reagent used for specimen analyzer 100. Consumables 50 include, for example, a reagent used for measurement of the specimen. Also, consumables 50 include a reagent used for the analysis. Moreover, consumables 50 include, for example, a reagent used for quality control of specimen analyzer 100. Furthermore, consumables 50 include, for example, a reagent used for cleaning of specimen analyzer 100.

Each of consumables 50 is provided with information record section 51 which includes the information on the consumable. Information record section 51 is attached to, for example, a container of each consumable 50. Information record section 51 includes, for example, a one-dimensional or two-dimensional barcode. Moreover, information record section 51 may be an RFID tag. Furthermore, information record section 51 may be a sign being a combination of characters, symbols, etc. It is possible to read information record section 51 with information read unit 30. The information which is possessed by information record section 51 and is related to each consumable includes at least one of the type, the expiration date, a lot number, and a serial number of the consumable. In addition, the information on the consumables may include information on the type of the analysis apparatus to be used.

Controller 40 is configured to perform control such that the process does not shift to the next one concerning placement or replacement of consumables 50 unless the information on the consumables is input with information read unit 30. This makes it possible to advance the processing concerning the placement or replacement of consumables 50 after inputting information to determine whether or not consumables 50 are appropriate ones. Hence, it is possible to reliably place or replace appropriate consumables 50.

[Configuration Example of Specimen Analyzer]

Figure 2:
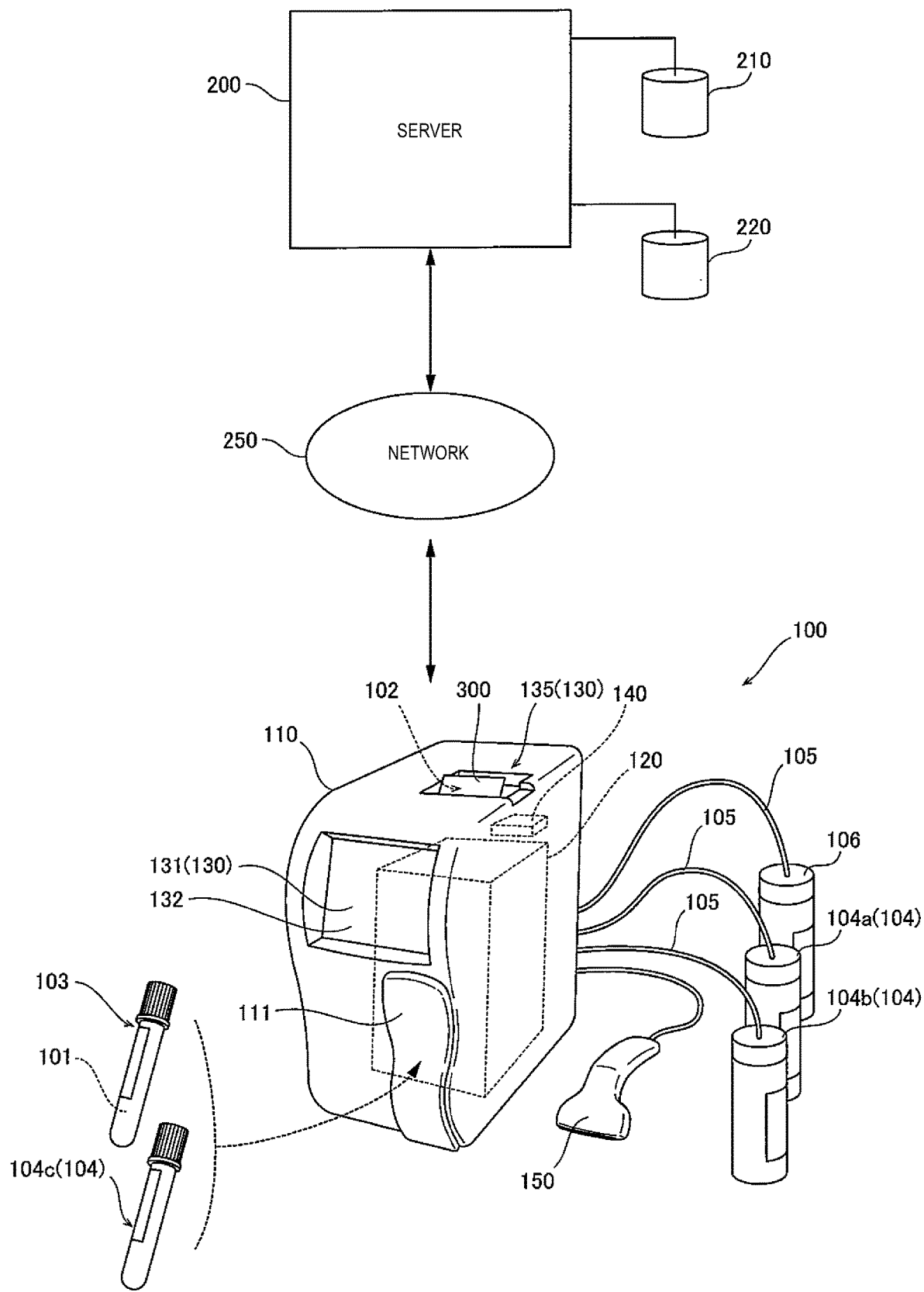
FIG. 2 is a perspective view illustrating a configuration example of the specimen analyzer.

With reference to FIG. 2 to FIG. 57, a configuration example of specimen analyzer 100 is described.

(Overall Configuration)

In the example illustrated in FIG. 2, specimen 101 is blood in specimen analyzer 100, and specimen analyzer 100 is a blood cell counting apparatus. The blood cell counting apparatus is an apparatus which counts the number of blood cells contained in a predetermined volume of blood specimen. Analysis unit 120 analyzes the number of blood cells and concentrations of the components contained in the blood.

When specimen container 103 containing specimen 101 is set, specimen analyzer 100 aspirates specimen 101 in specimen container 103 and analyzes the specimen. For example, a container in the shape of a generally-used blood collection tube can be used as specimen container 103. Specimen container 103 is, for example, a vacuum blood collection tube capped with a rubber cap or an open blood collection tube which has an opening. Specimen 101 to be contained in specimen container 103 is, for example, whole blood of a subject (human), and is added with an anticoagulant. The necessary amount of added anticoagulant is, for example, 10 µL to 15 µL inclusive.

Specimen analyzer 100 has apparatus body 110 which includes analysis unit 120 for analyzing the specimen collected from the subject, output unit 130 for outputting analysis results 102 of analysis unit 120, and controller 140. Moreover, specimen analyzer 100 includes information read unit 150 connected to apparatus body 110. Further, specimen analyzer 100 is connected to various types of consumables 104 used along with analysis operation for specimen 101.

Apparatus body 110 is a unit provided with analysis unit 120, output unit 130, etc. in a box-shaped housing. Apparatus body 110 is configured as a small blood cell counting apparatus which can be a desktop one, including information read unit 150 and consumables 104. Analysis unit 120 and controller 140 are built in apparatus body 110.

Container set unit 111 is provided at a front and lower portion of apparatus body 110. Container set unit 111 is configured such that it is openable and closable from the front surface of apparatus body 110 in the direction toward the user (see FIG. 3). Using container set unit 111, specimen container 103 containing specimen 101 is set in apparatus body 110.

In the example illustrated in FIG. 2, analysis unit 120 is configured to analyze multiple analysis items. As an example, as measurement items by analysis unit 120, the analysis items include e.g. eight items: white blood cell count (WBC), red blood cell count (RBC), hemoglobin concentration (HGB), hematocrit value (HCT), mean corpuscular volume (MCV), mean corpuscular hemoglobin (MCH), mean corpuscular hemoglobin concentration (MCHC), and platelet count (PLT). As analysis items to be analyzed on the basis of the analysis results of the measurement items, the analysis items include e.g. nine items: WBC-small cell ratio (% Lymph), WBC-middle cell ratio (% OtherWBC), WBC-large cell ratio (% Neut), WBC-small cell count (#Lymph), WBC-middle cell count (#Other-WBC), WBC-large cell ratio (#Neut), red blood cell distribution width (RDW-SD and RDW-CV), mean platelet volume (MPV). In this example, the number of analysis items of analysis unit 120 is 17.

Output unit 130 outputs various types of information on specimen analyzer 100 to the user. In the example of FIG. 2, output unit 130 includes display unit 131 and print unit 135. In the example of FIG. 2, display unit 131 is an LCD (liquid crystal display), and is disposed at a front and upper portion of apparatus body 110. Display unit 131 displays information. In the example of FIG. 2, print unit 135 is a thermal printer which prints on thermal paper with use of heat, and is located on an upper surface of apparatus body 110.

Moreover, specimen analyzer 100 includes manual input unit 132 which receives an input operation of the user. In the example of FIG. 2, manual input unit 132 is a touch panel provided on display unit 131. The user is allowed to input information and perform various operations by touching the icons displayed on display unit 131.

In the example of FIG. 2, information read unit 150 is configured to read an information record section provided on each of consumables 104, and to receive inputted information. To be more specific, information read unit 150 is a read apparatus such as a barcode reader, a two-dimensional code reader, and a camera. The information record section is a barcode or a two-dimensional code.

In the example of FIG. 2, inputting of information on consumables 104 by manual input unit 132 is not permitted, but inputting by information read unit 150 is permitted. Controller 140 determines whether to use consumables 104 based on information on consumables 104 inputted by information read unit 150. To be more specific, controller 140 allows use of consumables 104 if information on consumables 104 inputted by information read unit 150 is registered on server 200.

Consumables 104 are consumed along with analysis operation of specimen 101 by specimen analyzer 100. Consumables 104 contain the reagent used for the analysis of specimen 101. In the example of FIG. 2, used as consumables 104 are diluted solution container 104a containing a diluted solution for diluting specimen 101 and hemolyzer container 104b containing a hemolyzer which hemolyzes blood cells. Moreover, consumables 104 contain a cleaning agent for cleaning specimen analyzer 100. In the example of FIG. 2, used as consumable 104 is cleaning agent container 104c containing a cleaning agent for cleaning a fluid circuit in the apparatus. Note that the diluted solution is used for a cleaning process. The cleaning agent contains a cleaning component such as a sodium hypochlorite solution, and has more cleaning power than the diluted solution. Cleaning with use of the cleaning agent is regularly carried out each time a predetermined period elapses, e.g. one week. Cleaning with use of the diluted solution is carried out more frequently than the cleaning with use of the cleaning agent each time the analysis of specimen 101 is performed, for example. The information record sections provided on consumables 104 have information on consumables 104 recorded therein. Information on consumables 104 includes at least one of the type of consumable 104, expiration date, lot number, and serial number.

As an example, in the example of FIG. 2, "pocH-pack D (manufactured by Sysmex Corporation, registered trademark)" is preferably used as the diluted solution, "pocH-pack L (manufactured by Sysmex Corporation, registered trademark)" is preferably used as the hemolyzer, and "CELLCLEAN (manufactured by Sysmex Corporation, registered trademark)" is preferably used as the cleaning agent.

(Configuration of Each of Units of Specimen Analyzer)

Figure 3:
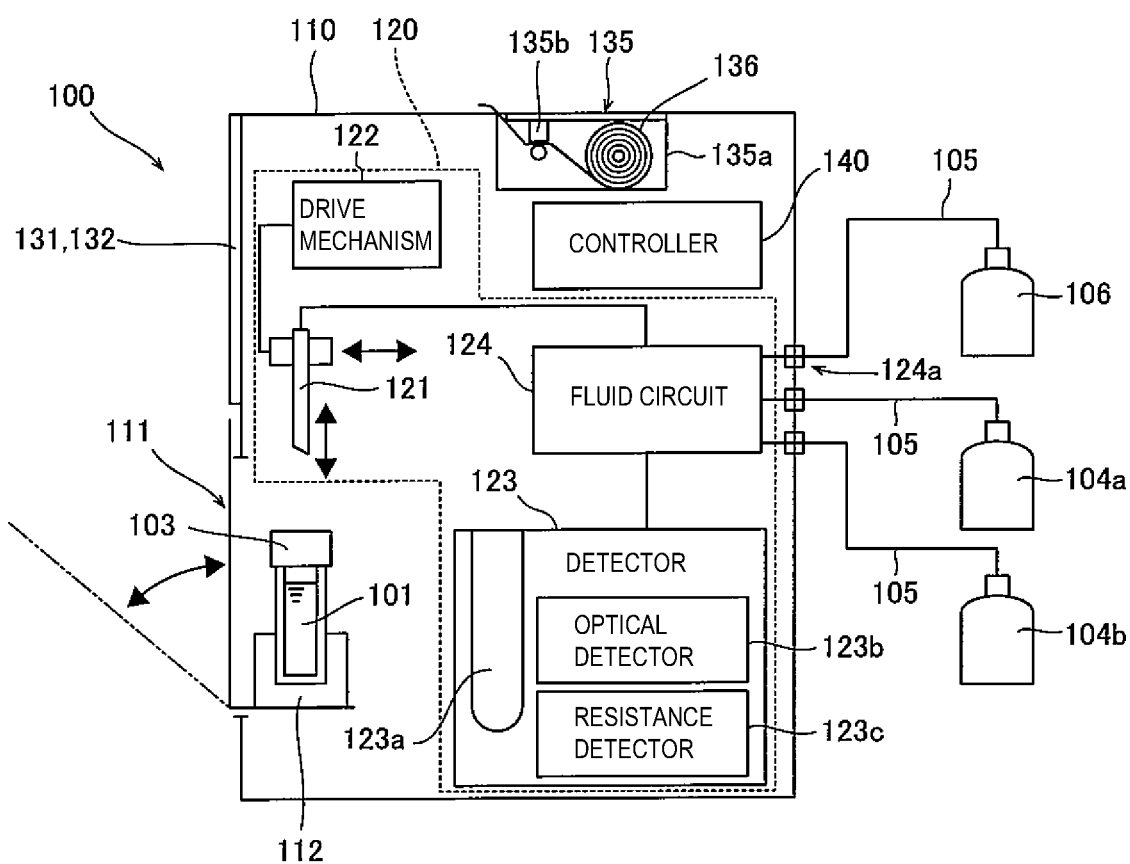
FIG. 3 is a schematic view illustrating an internal configuration example of the specimen analyzer.

In the example illustrated in FIG. 3, print unit 135 is configured such that it can change the size of print sheet 136, and is configured to print analysis results 102 on the same surface of a single piece of print sheet 136. To be more specific, print unit 135 includes sheet set unit 135a which holds print sheet 136 which is elongated, and changes the size of print sheet 136 by printing on an area of print sheet 136 with an appropriate length depending on the print amount. In the example of FIG. 3, set to sheet set unit 135a is print sheet 136 which is roll paper being rolled thermal paper which is elongated with a predetermined width. In addition, print unit 135 includes print head 135b which heats print sheet 136, and prints using print head 135b while forwarding rolled print sheet 136 with a not-illustrated motor. Thus, print unit 135 prints on an area of print sheet 136 with an appropriate length depending on the amount of information to be printed including analysis results 102. The user cuts the printed sheet sent from print unit 135 in an appropriate length, and acquires one sheet of printed sheet on which analysis results 102 are printed.

Container set unit 111 includes adapter 112 for holding a lower portion of specimen container 103. When open, container set unit 111 is capable of holding specimen container 103 in an upright state. Here, in addition to specimen container 103, it is possible to set, to container set unit 111, a QC reagent container (not illustrated) which contains a control specimen (hereinafter referred to as QC reagent) for quality control and cleaning agent container 104c.

Analysis unit 120 includes pipette 121 for aspirating specimen 101 from specimen container 103 set to container set unit 111 and drive mechanism 122 for pipette 121. Moreover, analysis unit 120 includes detector 123 for detecting components in specimen 101 and fluid circuit 124 for feeding liquid. Furthermore, analysis unit 120 (see FIG. 4) includes a computer which has processor 141 and memory 142.

Pipette 121 is an aspiration tube for measuring the amount of a liquid. Drive mechanism 122 includes linear mechanisms made up of e.g. a guiderail, a motor, and a belt pulley mechanism, and holds pipette 121. Pipette 121 is provided at a position above specimen container 103 set in container set unit 111, and is configured such that it can move in the up-down direction and in the horizontal direction. Pipette 121 is connected to a syringe pump provided in fluid circuit 124, and is capable of aspirating a predetermined amount of specimen 101 contained in specimen container 103. Pipette 121 is moved down from a position above specimen container 103, enters the inside of specimen container 103, and is allowed to aspirate a predetermined amount of specimen 101 by fluid circuit 124. Moreover, pipette 121 is moved by drive mechanism 122 to a position above a mixing chamber of fluid circuit 124 to be described later and to a position above container unit 123a of detector 123, and is allowed to aspirate and discharge liquid by fluid circuit 124 at each of the positions. In the case where the QC reagent container containing the QC reagent and the cleaning agent container are set in container set unit 111, pipette 121 can also aspirate the QC reagent and the cleaning agent by performing the same or similar operations.

Fluid circuit 124 includes e.g. a mixing chamber, a pressure source, a syringe pump, a diluted solution, chambers for hemolyzer and waste liquid, a cleaning Spitz for cleaning pipette 121, various valves for switching liquid feed, and a sensor. Fluid circuit 124 connects pipette 121 and detector 123 together in a fluid manner via a flow path such as a liquid feed tube. Moreover, fluid circuit 124 is connected in a fluid manner to external connectors 124a provided on the back surface of apparatus body 110. The number of external connectors 124a provided is three, which are separately connected via connection tubes 105 to diluted solution container 104a, hemolyzer container 104b, and waste liquid container 106.

Fluid circuit 124 mixes a predetermined amount of specimen 101 aspirated by pipette 121 and a predetermined amount of diluted solution in a mixing chamber to prepare an RBC/PLT measurement specimen, which is a diluted specimen with a predetermined ratio. In addition, fluid circuit 124 mixes a predetermined amount of specimen 101, a predetermined amount of diluted solution, and a predetermined amount of hemolyzer to prepare a WBC/HGB measurement specimen which includes a mixed solution of blood specimen, diluted solution, and hemolyzer.

Detector 123 is configured to measure the target components in specimen 101 corresponding to the analysis items. In the example of FIG. 3, detector 123 measures multiple items. In the example of FIG. 3, detector 123 is configured to perform measurement in accordance with multiple measurement principles depending on the target components of the analysis items.

To be more specific, detector 123 performs RBC measurement and PLT measurement using a sheath flow electrical resistance method. Detector 123 performs WBC measurement using an electrical resistance method. Detector 123 includes resistance detector 123b for performing measurement using the sheath flow electrical resistance method and the electrical resistance method. Moreover, detector 123 performs HGB measurement using a colorimetric method. Detector 123 includes optical detector 123c for performing measurement using the colorimetric method.

The sheath flow electrical resistance method forms a sheath flow of a specimen flow and a flow of sheath liquid surrounding the specimen flow, and causes the sheath flow to pass through an orifice. Electrodes are provided in front and rear of the orifice, respectively, in the flow direction. A pulse signal, which represents the presence and volume information of each blood cell, is measured based on the change in resistance between the electrodes generated by the blood cells passing through the orifice.

Here, the diluted solution forms the flow of sheath liquid, and the RBC/PLT measurement specimen forms the specimen flow. Resistance detector 123b includes an orifice and a pair of electrodes used for measurement. Analysis unit 120 obtains the red blood cell count (RBC), the platelet count (PLT), and the hematocrit value (HCT) from the measured count value of the pulse signal.

The electrical resistance method causes the WBC/HGB measurement specimen to pass through an orifice, and measures a pulse signal which represents the presence and volume information of each blood cell based on the change in resistance between the front and rear electrodes of the orifice. Analysis unit 120 obtains the white blood cell count (WBC) from the measured count value of the pulse signal.

The colorimetric method causes a light source to emit measurement light to the WBC/HGB measurement specimen, and detects the measurement light having passed through the specimen with a light receiving element. Additionally, the same process is also performed on the diluted solution, and analysis unit 120 obtains the hemoglobin concentration (HGB) based on the difference in absorbance between the diluted solution and the WBC/HGB measurement specimen. Optical detector 123c includes the light source and the light receiving element used for measurement. The light source is, for example, an LED, and the light receiving element is, for example, a photodiode.

The mean corpuscular volume (MCV), the mean corpuscular hemoglobin (MCH), and the mean corpuscular hemoglobin concentration (MCHC) are calculated by analysis unit 120 from the measurement values of the red blood cell count (RBC), the platelet count (PLT), and the hematocrit value (HCT), respectively.

Based on the analysis results of the measurement items, analysis unit 120 obtains the analysis items of the WBC-small cell ratio (% Lymph), the WBC-middle cell ratio (% OtherWBC), the WBC-large cell ratio (% Neut), the WBC-small cell count (#Lymph), the WBC-middle cell count (#OtherWBC), the WBC-large cell ratio (#Neut), the red blood cell distribution width (RDW-SD and RDW-CV), the mean platelet volume (MPV).

Figure 4:
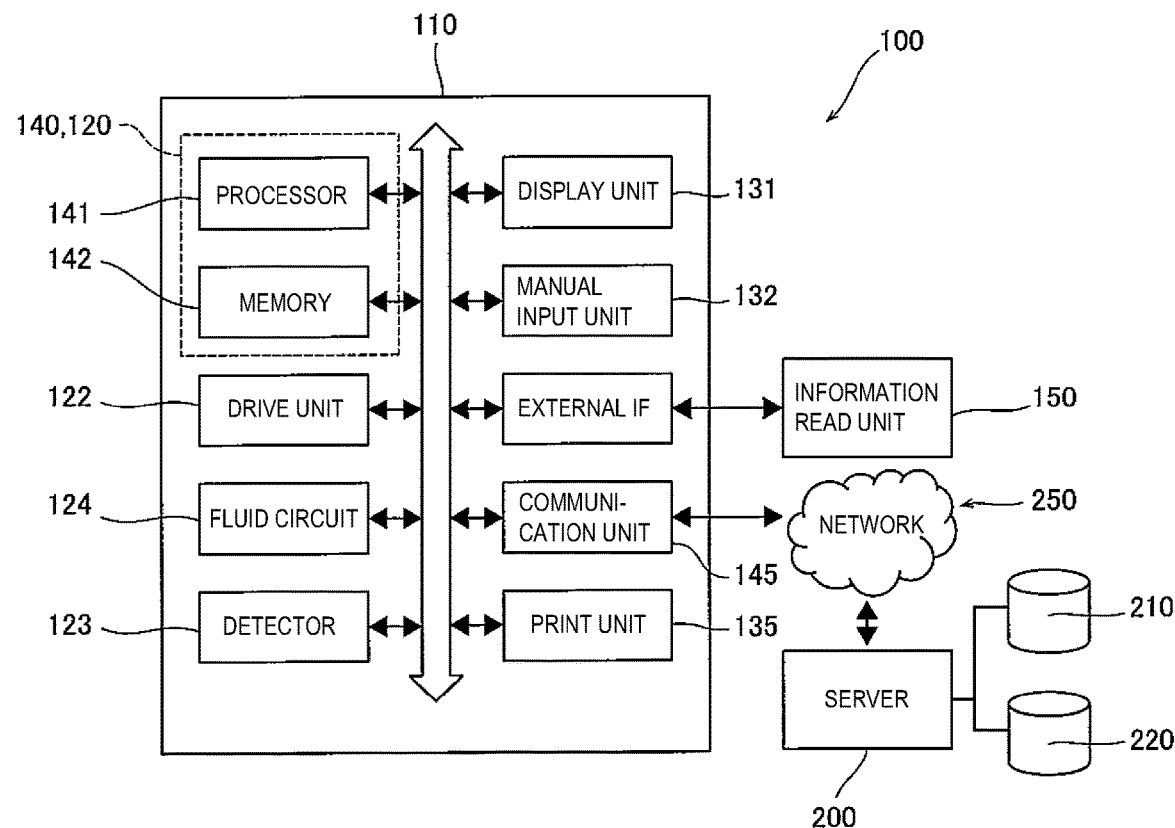
FIG. 4 is a block diagram illustrating a configuration of the specimen analyzer.

As illustrated in FIG. 4, controller 140 includes processor 141 such as a CPU and memory 142. Memory 142 can include a volatile memory such as a RAM, and a non-volatile memory such as a ROM, a flash memory, and a hard disk. Memory 142 has, for example, a control program for controlling specimen analyzer 100, analysis program for obtaining analysis results 102, and display screen data of display unit 131 recorded therein. Processor 141 executes a program recorded in memory 142 and thereby functions as controller 140 which performs operation control of units such as drive mechanism 122, fluid circuit 124, detector 123, display unit 131, and print unit 135. Moreover, processor 141 functions as part of analysis unit 120 which obtains analysis results 102 of the analysis items by executing the programs recorded in memory 142. Controller 140 and analysis unit 120 may be configured as a separate processor and memory. Furthermore, controller 140 obtains information inputted through manual input unit 132 and processes that information. What is more, controller 140 controls read operation by information read unit 150 through an external IF, and processes the read information. Still further, controller 140 is capable of connecting to network 250 via communication unit 145, and thus accessing management server 200 of specimen analyzer 100. Communication unit 145 includes a communication interface, and establishes cabled or wireless connection to network 250. Communication unit 145 connects to network 250 via, for example, an Ethernet cable.

Controller 140 is configured to perform control of causing display unit 131 to display how to input information on consumables. This makes it possible to input the information on the consumables in accordance with the display of display unit 131, facilitating input operation without mistakes. More specifically, controller 140 is configured to perform control of causing display unit 131 to display an instruction prompting to input the information on the consumables with information read unit 150. This makes it possible to guide a user to read the information on the consumables with information read unit 150. Hence, the user can easily input the information on the consumables.

In addition, controller 140 is configured to perform control of causing display unit 131 to display a message based on a determination as to whether or not inputted information is appropriate. This makes it possible to prevent use of inappropriate consumable 104 because information on the inappropriateness is displayed as a message if consumable 104 is inappropriate. Also, it is possible to prompt to use the appropriate consumable by displaying the reason for inappropriateness. For example, controller 140 is configured to perform control of acquiring an expiration date of a consumable based on information on the consumable, and causing display unit 131 to display a message based on a determination as to whether or not the expiration date has passed. This makes it possible to prevent use of expired consumable 104, which can prompt to use a more appropriate consumable.

Also, consumables 104 include a disposable consumable. For example, a cleaning agent for cleaning the inside of specimen analyzer 100 is a disposable consumable 104. If an information record section of disposable consumable 104 is read again after use of the disposable consumable, controller 140 is configured to perform control of not permitting use of consumable 140, and causing display unit 131 to display an error message. This makes it possible to prevent a situation where disposable consumable 104 is used again, which can prompt to use a more appropriate consumable.

Furthermore, controller 40 is configured to perform control of acquiring whether or not consumable 104 is usable based on information on the consumable, and causing display unit 131 to display an error message in a case where consumable 104 is unusable. For example, controller 140 is configured to perform control of acquiring a type of consumable 104 based on information on the consumable, and causing display unit 131 to display an error message in a case where the type of consumable 104 is different. This makes it possible to prevent a situation where consumable 104 of different types is set and used.

In addition, controller 140 is configured to perform control of causing communication unit 145 to transmit information on consumables inputted with information read unit 150 to server 200. This makes it possible to manage consumables 140 with external server 200, enabling more appropriate and easier management of consumables 140. For example, controller 140 does not permit inputting of information on a consumable when it is impossible to connect to server 200 via communication unit 145. This makes it possible to reliably manage consumables 104 with external server 200 because placement or replacement of consumables 104 is not allowed when it is impossible to connect to server 200.

In other words, communication unit 145 can transmit the information on the consumable inputted with information read unit 150, which works as an input unit, to external server 200. Controller 140 is configured to allow analysis unit 120 to analyze a specimen if connection is established between server 200 and communication unit 145. This makes it possible to manage consumable 50 with external server 200, enabling more appropriate and easier management of consumables 104 such as reagents.

Also, controller 140 is configured to permit use of consumable 104 if the information on the consumable inputted with information read unit 150 is registered in server 200. This makes it possible to effectively prevent use of inappropriate consumable 104. More specifically, controller 140 is configured to permit use of consumable 104 if a lot number as the information on the consumable is registered in server 200. This makes it possible to more easily manage consumable 104 by managing the lot number of consumable 104 with server 200.

In addition, controller 140 does not shift to a next process concerning placement or replacement of consumable 104 unless the information on the consumable is input with information read unit 150. This makes it possible to advance the processing concerning the placement or replacement of consumable 104 after inputting information to determine whether or not consumable 104 is an appropriate one. Hence, it is possible to reliably place or replace appropriate consumable 104. For example, controller 140 is configured to perform control of causing display unit 131 not to shift a screen of display unit 131 concerning placement or replacement of consumable 104 to a next screen unless the information on the consumable is input with information read unit 150. This makes it possible to effectively prevent placement or replacement of inappropriate consumable 104 because a screen to advance placement or replacement of consumable 104 is not displayed until the information on the consumable is input with information read unit 150.

(Description on Server)

Registered with storage unit 210 of server 200 are serial numbers of individual specimen analyzers 100. To be more specific, the user is allowed to use only specimen analyzers 100 registered with server 200. Registered with storage unit 220 of server 200 are lot numbers and serial numbers of reagents. To be more specific, the user is allowed to use only the reagents registered with server 200 in specimen analyzer 100. Moreover, stored in storage unit 220 of server 200 is information on a QC reagent. Information on a QC reagent is stored associated with the lot number of that QC reagent. To be more specific, information on a QC reagent includes information on a measurement range of the QC reagent. For example, QC reagents used include a High QC reagent containing a highly concentrated component, a Normal QC reagent containing a normally concentrated component, and a Low QC reagent containing a low concentrated component. A normal value of the measurement result is set for each QC reagent depending on High, Normal, and Low. Moreover, the QC reagent has a varying normal value depending on the lot. In light of this, storage unit 220 of server 200 stores ranges of normal values in the case of measuring QC reagents depending on the types High, Normal, and Low, and the lot number.

[Operation Example of Specimen Analyzer]

Figure 5:
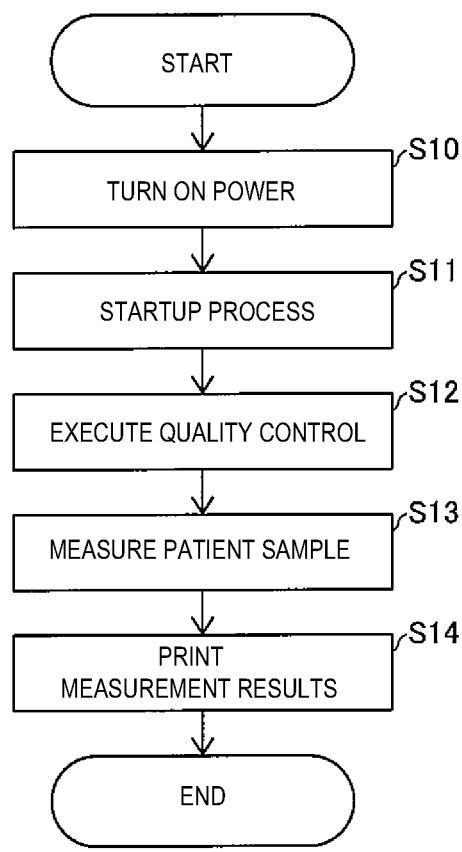
FIG. 5 is a flowchart illustrating an example of operations of the specimen analyzer.

With reference to FIG. 5, an operation example of specimen analyzer 100 is described.

When the power is turned ON at step S10, a startup process is performed at step S11. To be more specific, the system is automatically checked. Also, the inside of the apparatus is automatically cleaned. Additionally, blank check is performed.

At step S12, quality control is executed. The quality control is performed at predetermined intervals. Display unit 131 displays a screen requiring quality control at predetermined intervals. The user inputs data concerning quality control in accordance with what is being displayed, and instructs to measure quality control substances.

At step S13, a patient sample as a specimen is measured. Display unit 131 displays a screen of an instruction for sample measurement. The user performs sample measurement instruction in accordance with what is being displayed. At step S14, the measurement results are printed. To be more specific, the measured and analyzed results are printed and outputted from print unit 135. Note that display unit 131 does not display the measurement results.

[Description on Sample Measurement Process]

Figure 6:
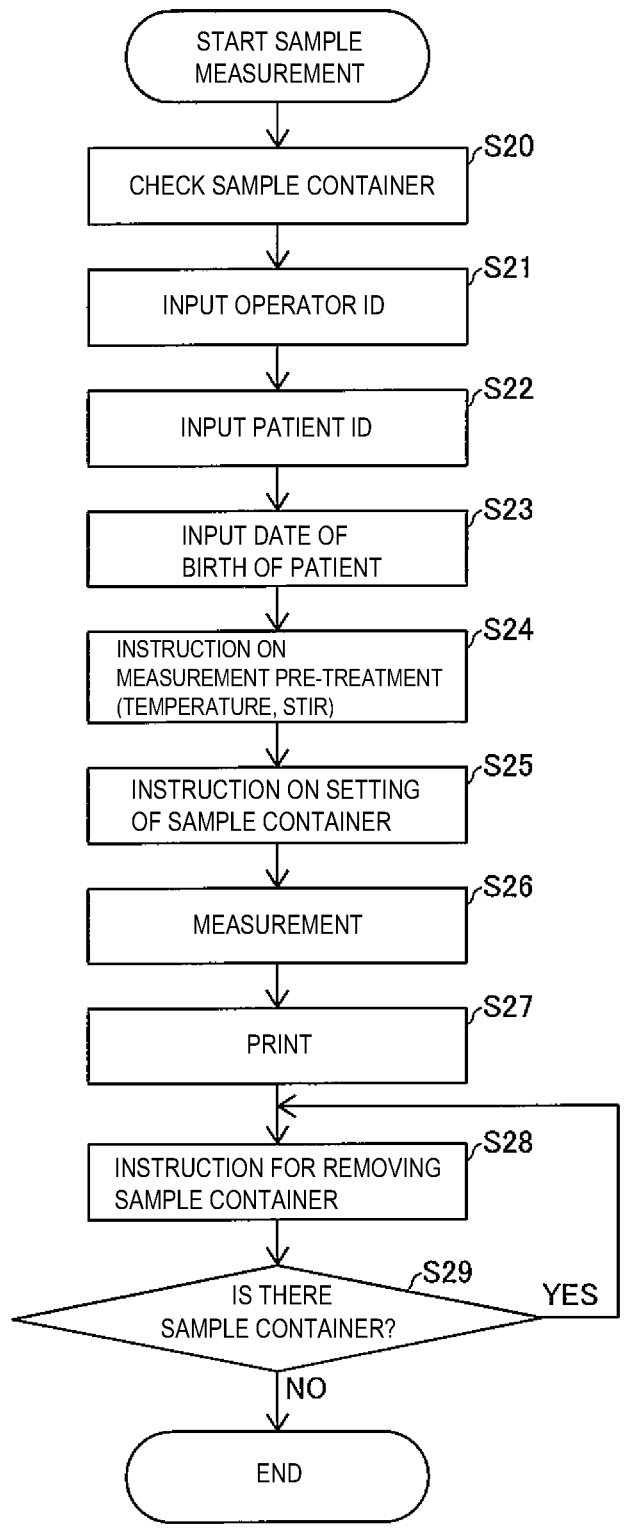
FIG. 6 is a flowchart illustrating an example of a sample measurement process.

With reference to FIG. 6, an example of a sample measurement process by specimen analyzer 100 is described. In the example illustrated in FIG. 6, specimen analyzer 100 measures and analyzes the sample of a patient as a specimen.

At step S20, a sample container is checked. To be more specific, display unit 131 displays images of the types of sample containers available. The user checks the sample container by comparing the images and the actual sample container. At step S21, an operator ID is inputted. To be more specific, the user inputs an ID for identifying the operator in accordance with the instructions of display unit 131.

At step S22, a patient ID is inputted. To be more specific, the user inputs an ID for identifying the patient in accordance with the instructions of display unit 131. At step S23, the date of birth of the patient is inputted. To be more specific, the user inputs the date of birth of the patient being the sample to be measured in accordance with the instructions of display unit 131.

At step S24, a measurement pre-treatment is performed. To be more specific, display unit 131 displays the instructions on the pre-treatment. The user performs the pre-treatment such as heating and stirring of the sample in accordance with the instructions of display unit 131. At step S25, a sample container is set. To be more specific, display unit 131 displays the instructions on the setting of the sample container. The user sets the sample container in specimen analyzer 100 in accordance with the instructions of display unit 131.

At step S26, the sample is measured. When the measurement of the sample finishes, measurement results are printed at step S27. To be more specific, after the measurement finishes, display unit 131 displays a button for starting of the printing. When the user operates the button for starting of the printing, print unit 135 prints the measurement result. The printing results are, for example, the name of the hospital, its location, the name of the measurement apparatus, the date and time of measurement, the operator ID, patient ID, the date of birth of the patient, the measurement results, messages, information on the reference value, and a print end mark.

At step S28, the sample container is removed. To be more specific, display unit 131 displays the instructions for removing the sample container. The user removes the sample container from specimen analyzer 100 in accordance with the instructions of display unit 131. At step S29, determination is made as to whether or not there is a sample container. If there is a sample container, the process returns to step S28, and if there is no sample container, the sample measurement process finishes.

[Display Example of Display Unit]

With reference to FIG. 7 to FIG. 48, a display example of display unit 131 in a case of using specimen analyzer 100 is described. It is possible to operate specimen analyzer 100 by following a series of instructions displayed on display unit 131.

(Display Example when Connecting Ethernet Cable)

Figure 7:
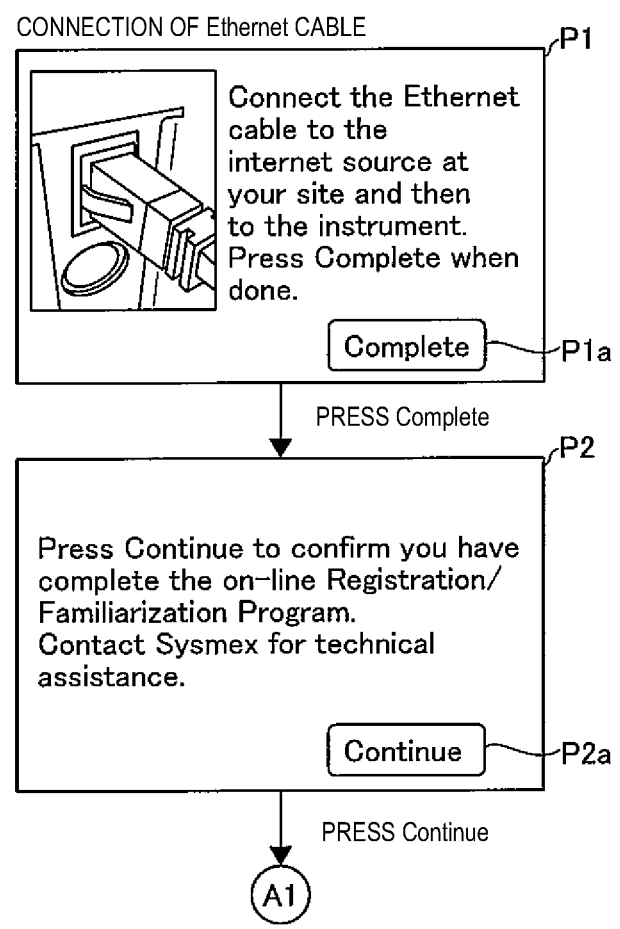
FIG. 7 is a diagram illustrating display example 1 for connecting an Ethernet cable.
Figure 8:
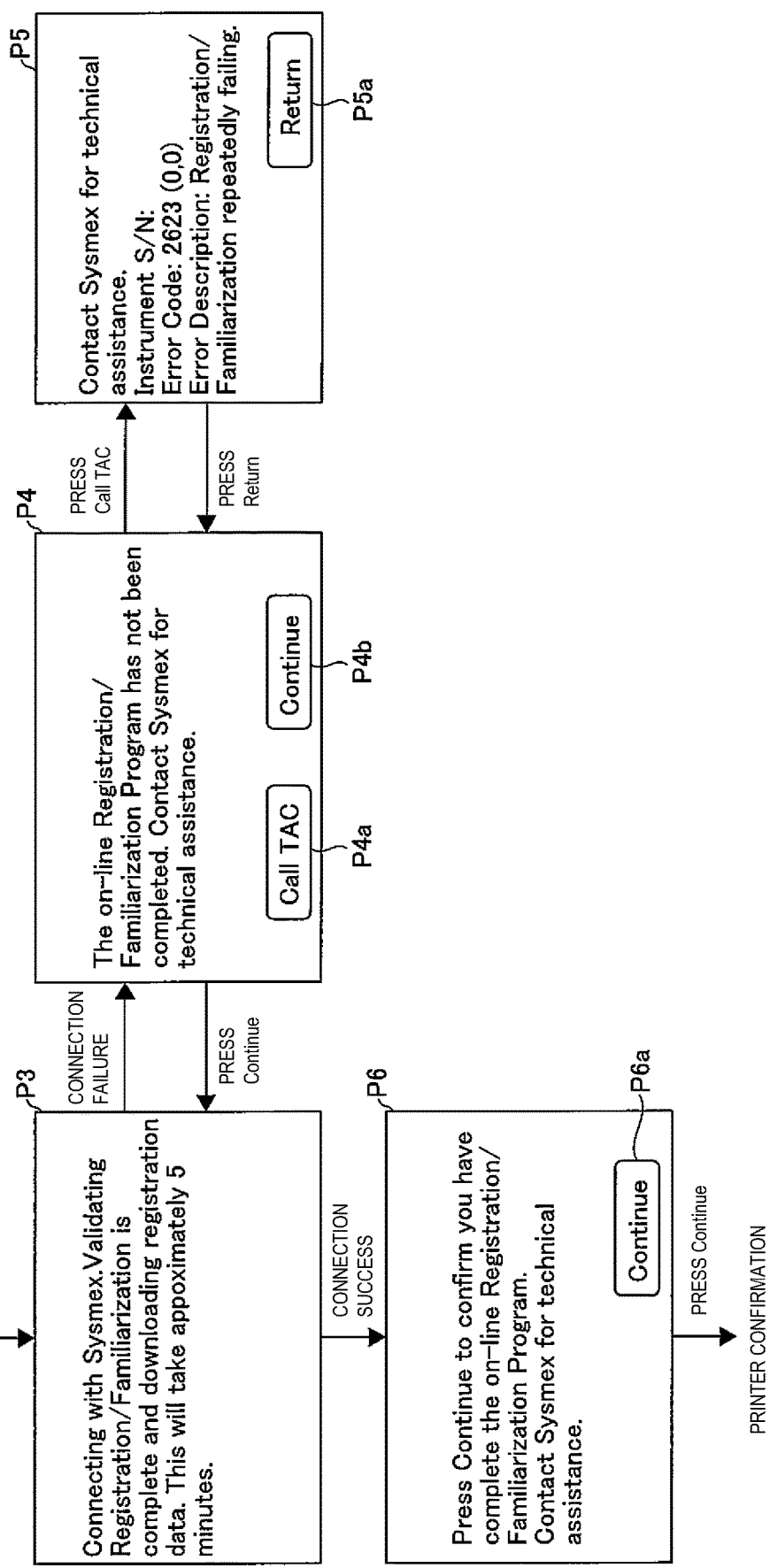
FIG. 8 is a diagram illustrating display example 2 for connecting an Ethernet cable.

With reference to FIG. 7 and FIG. 8, a display example when connecting an Ethernet cable is described.

It is impossible to use specimen analyzer 100 unless it is connected to server 200 via network 250. To be more specific, it is possible to use specimen analyzer 100 if it is registered with server 200. It is necessary to connect to server 200 in order to check whether or not specimen analyzer 100 is registered. Specimen analyzer 100 is connected to network 250 with an Ethernet cable. To this end, it is necessary to connect an Ethernet cable to specimen analyzer 100.

To begin with, when specimen analyzer 100 is set and the power is turned on, display unit 131 first displays a screen for connecting an Ethernet cable. To be more specific, as illustrated in FIG. 7, display unit 131 displays screen P1. Screen P1 shows a picture and an instruction on how to insert the Ethernet cable to specimen analyzer 100. Also, screen P1 shows Complete button P1a. When Complete button P1a is pressed, display unit 131 displays screen P2. Screen P2 shows Continue button P2a. When Continue button P2a is pressed, display unit 131 displays screen P3, as illustrated in FIG. 8. Thus, communication unit 145 of specimen analyzer 100 starts connection to server 200.

If the connection fails while screen P3 is being displayed, display unit 131 displays screen P4. Screen P4 shows Call TAC button P4a and Continue button P4b. When Call TAC button P4a is pressed, display unit 131 displays screen P5. When Continue button P4b is pressed, display unit 131 again displays screen P3.

Screen P5 shows error details. If the user telephones to a TAC (Technical Assistance Center) and communicates the description of screen P5, he/she can receive support smoothly. Screen P5 shows Return button P5a. When Return button P5a is pressed, display unit 131 displays screen P4.

If the connections succeeds while screen P3 is being displayed, display unit 131 displays screen P6. Screen P6 shows Continue button P6a. When Continue button P6a is pressed, the instructions to connect an Ethernet cable stop being displayed. Then, the screen proceeds to a screen of printer confirmation.

(Display Example at Printer Confirmation)

With reference to FIG. 9 to FIG. 12, a display example at printer confirmation is described.

Figure 9:
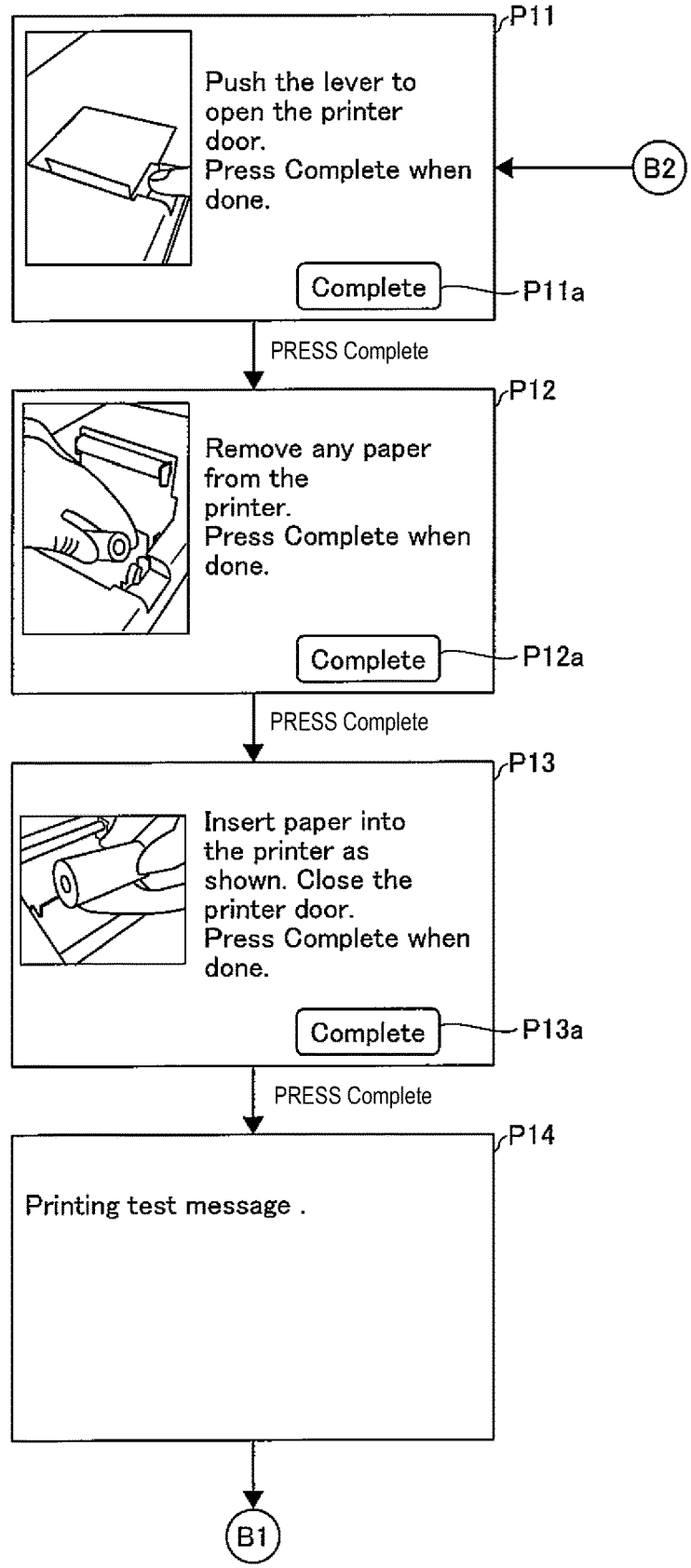
FIG. 9 is a diagram illustrating display example 1 for printer confirmation.

Display unit 131 displays a screen for confirming a printer as print unit 135. As illustrated in FIG. 9, display unit 131 displays screen P11. Screen P11 shows a picture and an instruction on how to open a door of the printer. Also, screen P11 shows Complete button P11a. When Complete button P11a is pressed, display unit 131 displays screen P12. Screen P12 shows a picture and an instruction on how to remove paper from the printer. Also, screen P12 shows Complete button P12a. When Complete button P12a is pressed, display unit 131 displays screen P13.

Screen P13 shows a picture and an instruction on how to insert paper in the printer and close the door. Also, screen P13 shows Complete button P13a. When Complete button P13a is pressed, display unit 131 displays screen P14. Thus, print unit 135 starts test printing.

Figure 10:
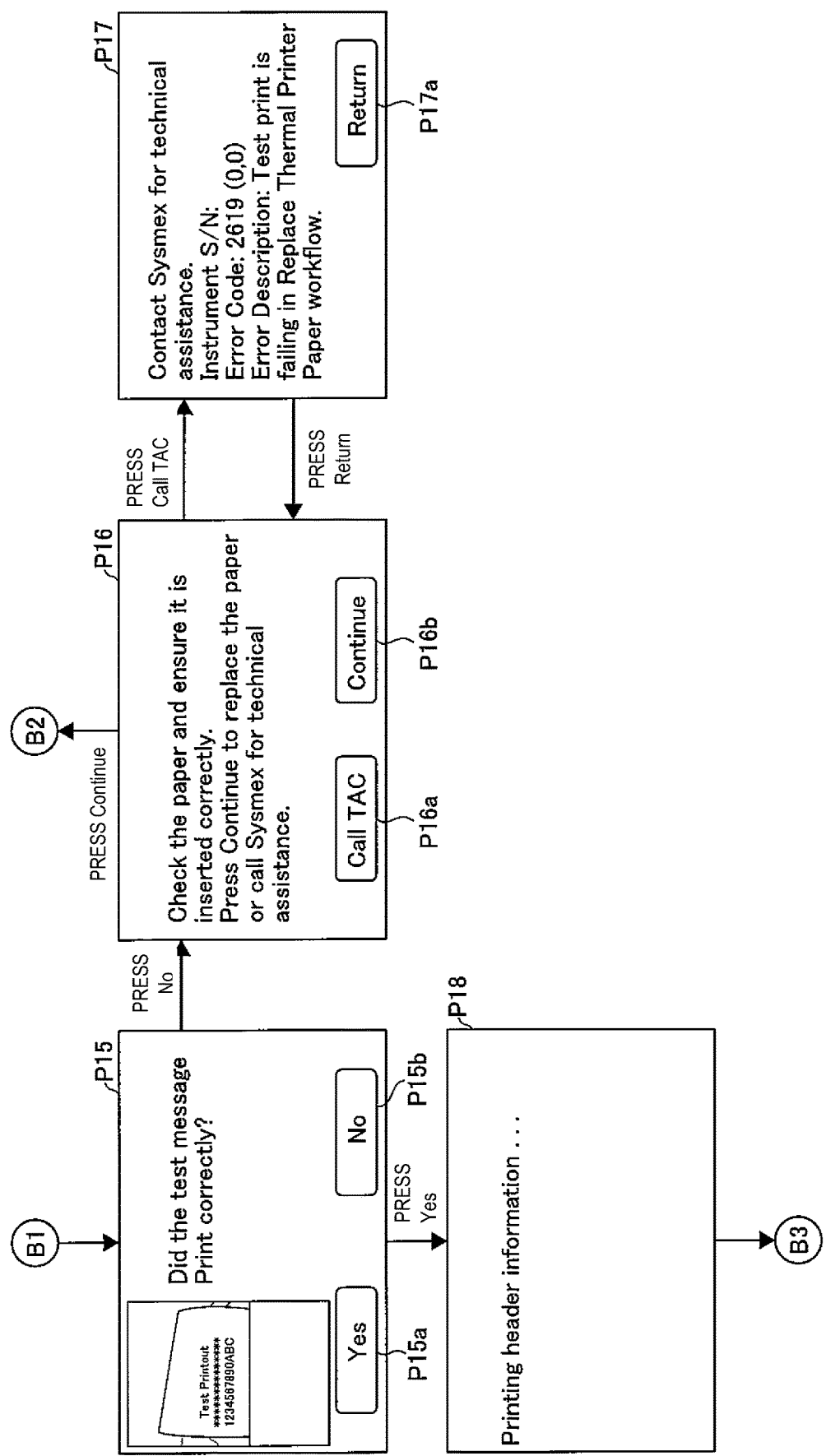
FIG. 10 is a diagram illustrating display example 2 for printer confirmation.

When the test printing finishes, display unit 131 displays screen P15 as illustrated in FIG. 10. Screen P15 shows a question asking whether or not the test printing has been correctly done, Yes button P15a, and No button P15b. When No button P15b is pressed, display unit 131 displays screen P16. When Yes button P15a is pressed, display unit 131 displays screen P18.

Screen P16 shows Call TAC button P16a and Continue button P16b. When Call TAC button P16a is pressed, display unit 131 displays screen P17. When Continue button P16b is pressed, display unit 131 again displays screen P11 (see FIG. 9).

Screen P17 shows error details. If the user telephones to the TAC and communicates the description of screen P17, he/she can receive support smoothly. Screen P17 shows Return button P17a. When Return button P17a is pressed, display unit 131 displays screen P16.

Figure 11:
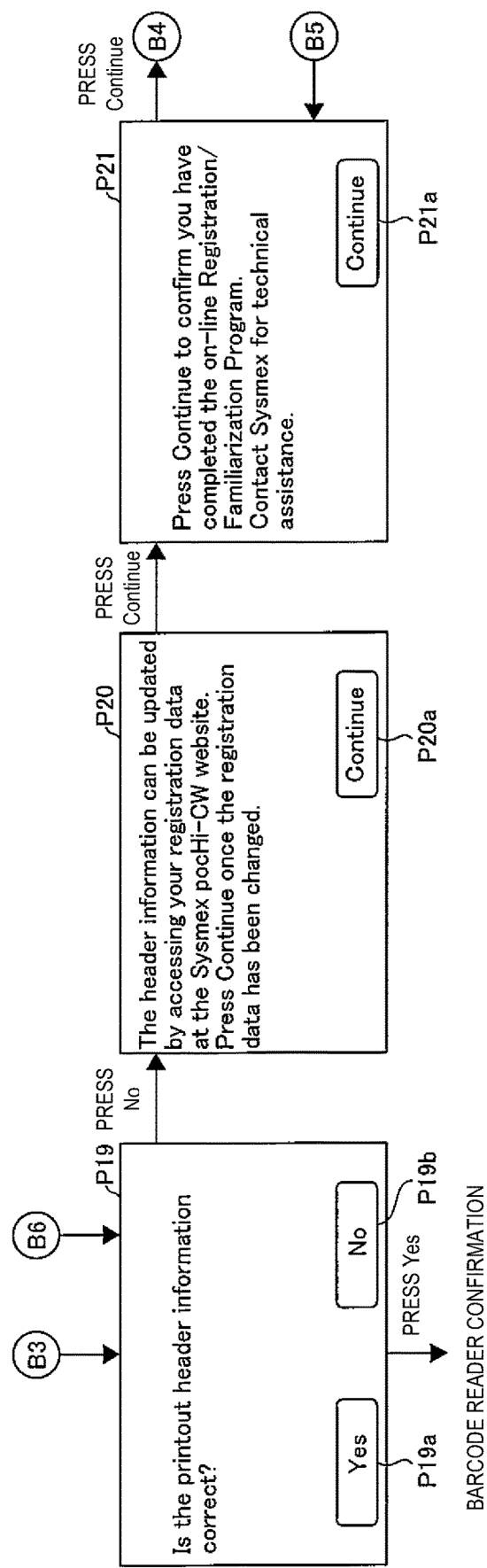
FIG. 11 is a diagram illustrating display example 3 for printer confirmation.

Display unit 131 displays screen P18 and print unit 135 starts printing header information. When the printing of the header information finishes, display unit 131 displays screen P19, as illustrated in FIG. 11. Screen P19 shows a question asking whether or not the header information is correct, Yes button P19a, and No button P19b. When No button P19b is pressed, display unit 131 displays screen P20. When Yes button P19a is pressed, printer confirmation stops being displayed. Then, the screen proceeds to a screen of barcode reader conformation.

Figure 12:
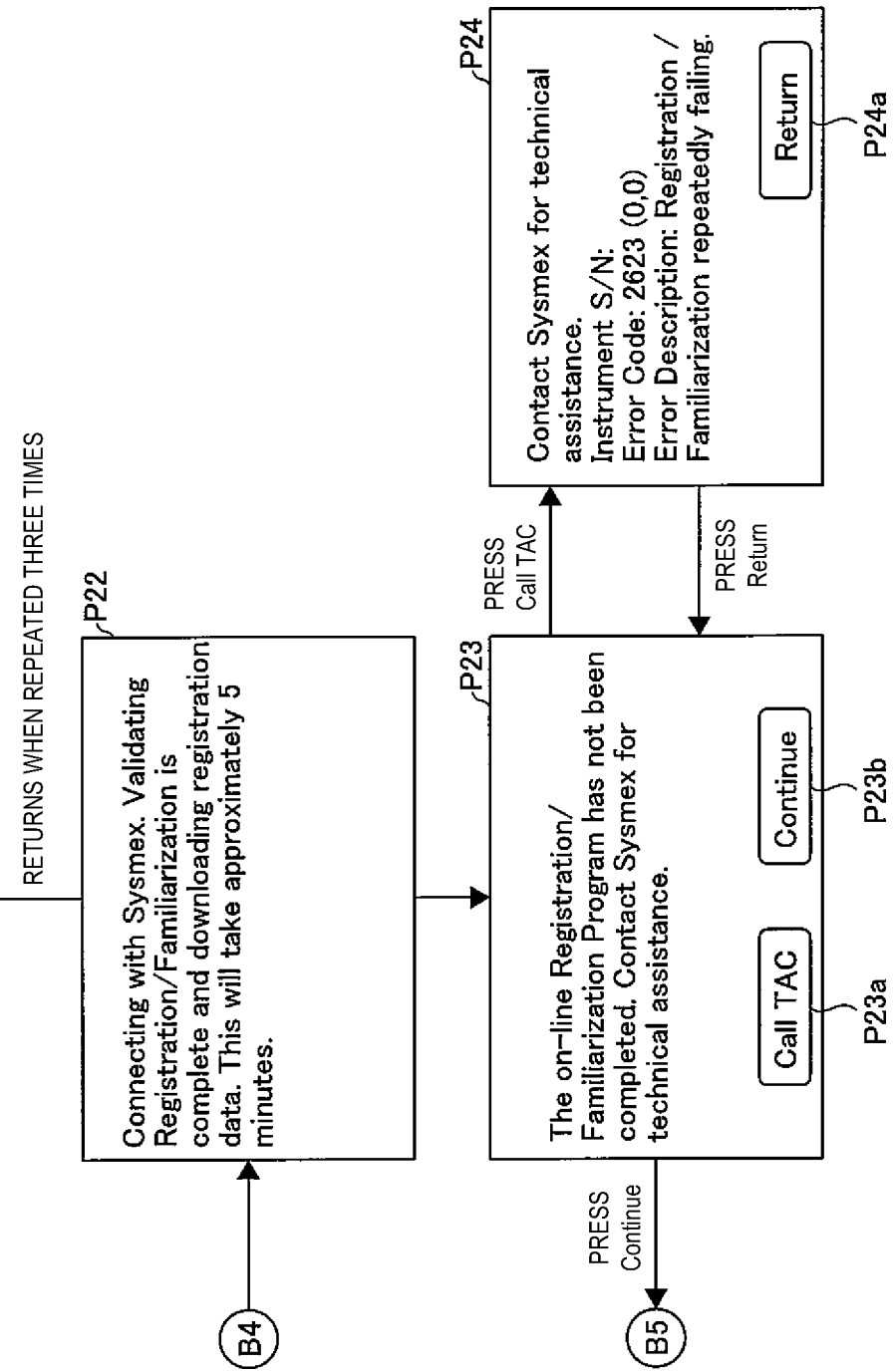
FIG. 12 is a diagram illustrating display example 4 for printer confirmation.

Screen P20 shows a description on update of header information and Continue button P20a. When Continue button P20a is pressed, display unit 131 displays screen P21. Screen P21 shows Continue button P21a. When Continue button P21a is pressed, screen P22 is displayed, as illustrated in FIG. 12.

Screen P22 shows a description on data download. Then, display unit 131 displays screen P23. It is to be noted that if screen P22 is repeated three times, display unit 131 displays screen P19 (see FIG. 11). Screen P23 shows Call TAC button P23a and Continue button P23b. When Call TAC button P23a is pressed, display unit 131 displays screen P24. When Continue button P23b is pressed, display unit 131 again displays screen P21 (see FIG. 11).

Screen P24 shows error details. If the user telephones to the TAC and communicates the description of screen P24, he/she can receive support smoothly. Screen P24 shows Return button P24a. When Return button P24a is pressed, display unit 131 displays screen P23.

(Display Example at Barcode Reader Confirmation)

With reference to FIG. 13, a display example at barcode reader confirmation is described.

Specimen analyzer 100 can input information on a reagent as a consumable and on CELLCLEAN for cleaning only through a barcode reader as information read unit 150. To be more specific, it is necessary to correctly attach a barcode reader to specimen analyzer 100.

As barcode reader confirmation, display unit 131 displays screen P31, as illustrated in FIG. 13. Screen P31 shows a picture of the barcode reader, a question asking whether or not the barcode reader gives off red light when the button is pressed, Yes button P31a, and No button P31b. When No button P31b is pressed, display unit 131 displays screen P32. When Yes button P31a is pressed, display unit 131 displays screen P36.

Screen P32 shows a picture instructing to connect the barcode reader, a question asking whether or not the barcode reader is connected to specimen analyzer 100, Yes button P32a, and No button P32b. When No button P32b is pressed, display unit 131 displays screen P33. When Yes button P32a is pressed, display unit 131 displays screen P34. Screen P33 shows a picture and an instruction on how to connect the barcode reader. Also, screen P33 shows Complete button P33a. When Complete button P33a is pressed, display unit 131 displays screen P31.

Screen P34 shows a description on a problem with the barcode reader and Call TAC button P34a. When Call TAC button P34a is pressed, display unit 131 displays screen P35. Screen P35 shows Return button P35a. When Return button P35a is pressed, display unit 131 displays screen P34.

Screen P36 shows a picture and an instruction on how to read the barcode of the Quick Guide using the barcode reader. When the barcode reader completes reading the barcode of the Quick Guide, display unit 131 displays screen P37. Screen P37 shows Continue button P37a. When Continue button P37a is pressed, the screen of barcode reader confirmation finishes being displayed. Then, the screen proceeds to a screen of the connection of various types of tubes.

(Display Example at Connection of Various Types of Tubes)

With reference to FIG. 14, a display example at the connection of various types of tubes is described.

Display unit 131 displays screen P41 in order to connect various types of tubes to specimen analyzer 100, as illustrated in FIG. 14. Screen P41 shows a picture and an instruction on how to connect various types of tubes to specimen analyzer 100. Also, screen P41 shows Complete button P41a. When Complete button P41a is pressed, display unit 131 displays screen P42. Screen P42 shows instructions to place a reagent container, a waste liquid container etc. to be connected to tubes next to specimen analyzer 100. Also, screen P42 shows Complete button P42a. When Complete button P42a is pressed, display unit 131 displays screen P43.

Screen P43 shows a picture and an instruction on how to connect the waste liquid container. Also, screen P43 shows Complete button P43a. When Complete button P43a is pressed, display unit 131 displays screen P44. Finally, the screen on connecting various types of tubes finishes being displayed. Then, the screen proceeds to a screen of reagent setting.

(Display Example when Setting Reagent)

With reference to FIG. 15 to FIG. 21, a display example when setting a reagent is described.

Figure 15:
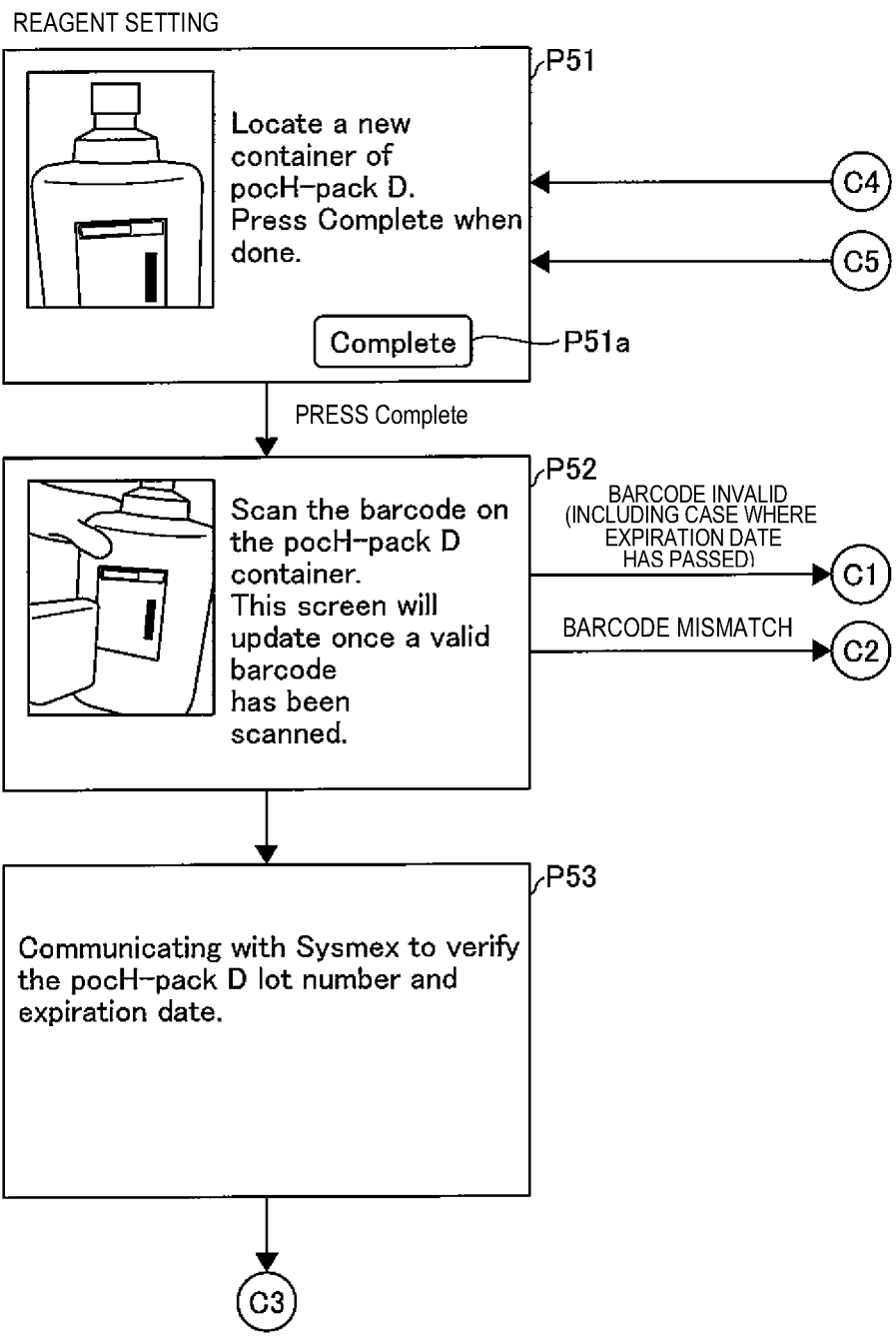
FIG. 15 is a diagram illustrating display example 1 for setting a reagent.

Display unit 131 displays screen P51 in order to set a reagent, as illustrated in FIG. 15. Screen P51 shows a picture and an instruction on how to set a container of a diluted solution used to analyze a specimen. Also, screen P51 shows Complete button P51a. When Complete button P51a is pressed, display unit 131 displays screen P52. Screen P52 shows a picture and an instruction on how to read a barcode attached on the container of the diluted solution. When the barcode is correctly read, display unit 131 displays screen P53. If a barcode is invalid, including the case where the expiration date has passed, display unit 131 displays screen P54 (see FIG. 16). If the barcode does not match, display unit 131 displays screen P55 (see FIG. 16).

While screen P53 is being displayed, connection is established to server 200, and whether or not the reagent can be used is checked. Thereafter, display unit 131 displays screen P57 (see FIG. 17).

Figure 16:
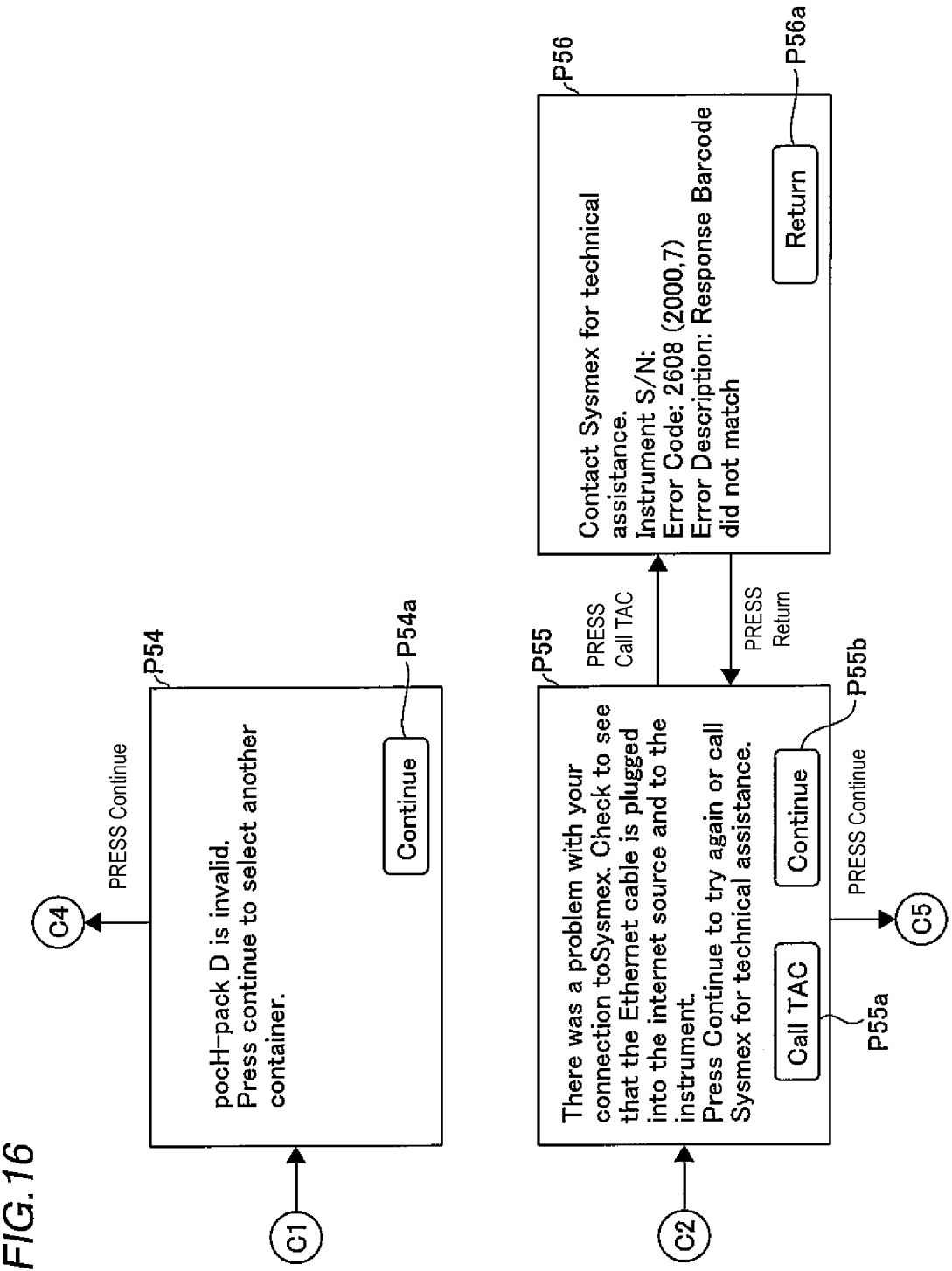
FIG. 16 is a diagram illustrating display example 2 for setting a reagent.

As illustrated in FIG. 16, screen P54 shows a description that the reagent of the read barcode is invalid. Also, screen P54 shows Continue button P54a. When Continue button P54a is pressed, display unit 131 displays screen P51 (see FIG. 15).

Screen P55 shows a description that there is a problem with the connection. Also, screen P55 shows Call TAC button P55a and Continue button P55b. When Call TAC button P55a is pressed, display unit 131 displays screen P56. When Continue button P55b is pressed, display unit 131 displays screen P51 (see FIG. 15). Screen P56 shows error details. If the user telephones to the TAC and communicates the description of screen P56, he/she can receive support smoothly. Screen P56 shows Return button P56a. When Return button P56a is pressed, display unit 131 displays screen P55.

Figure 17:
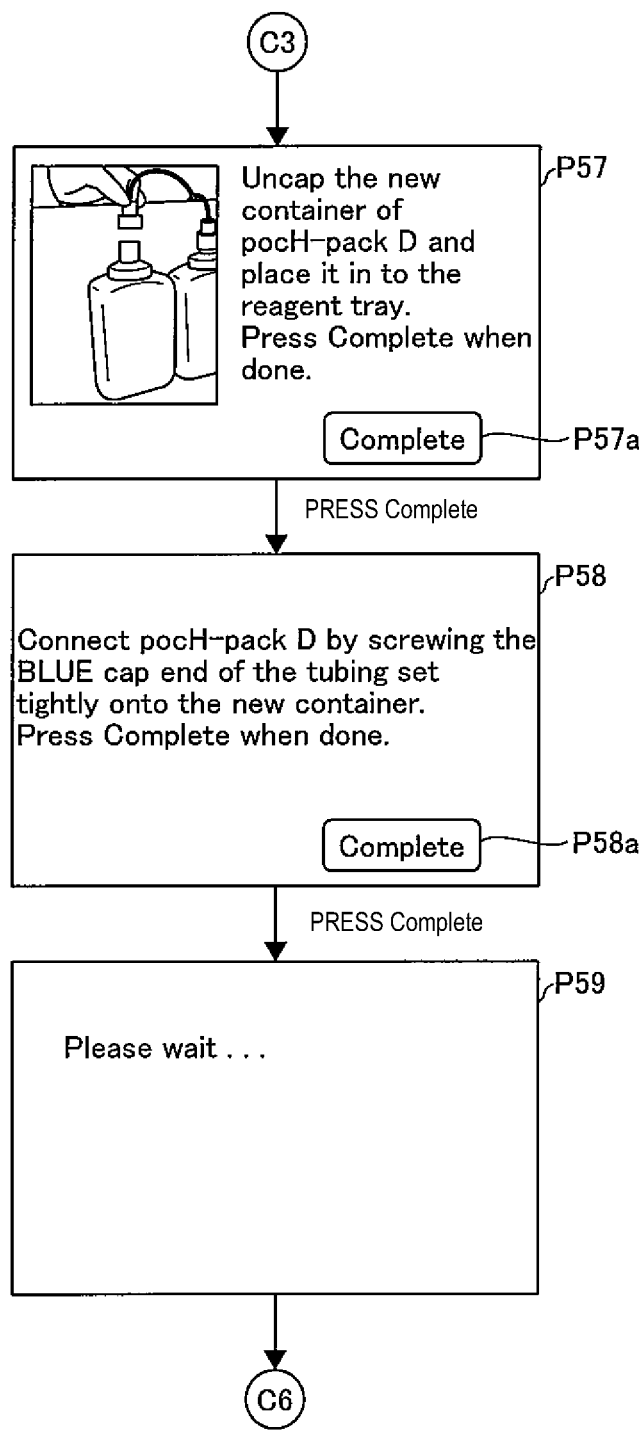
FIG. 17 is a diagram illustrating display example 3 for setting a reagent.
Figure 18:
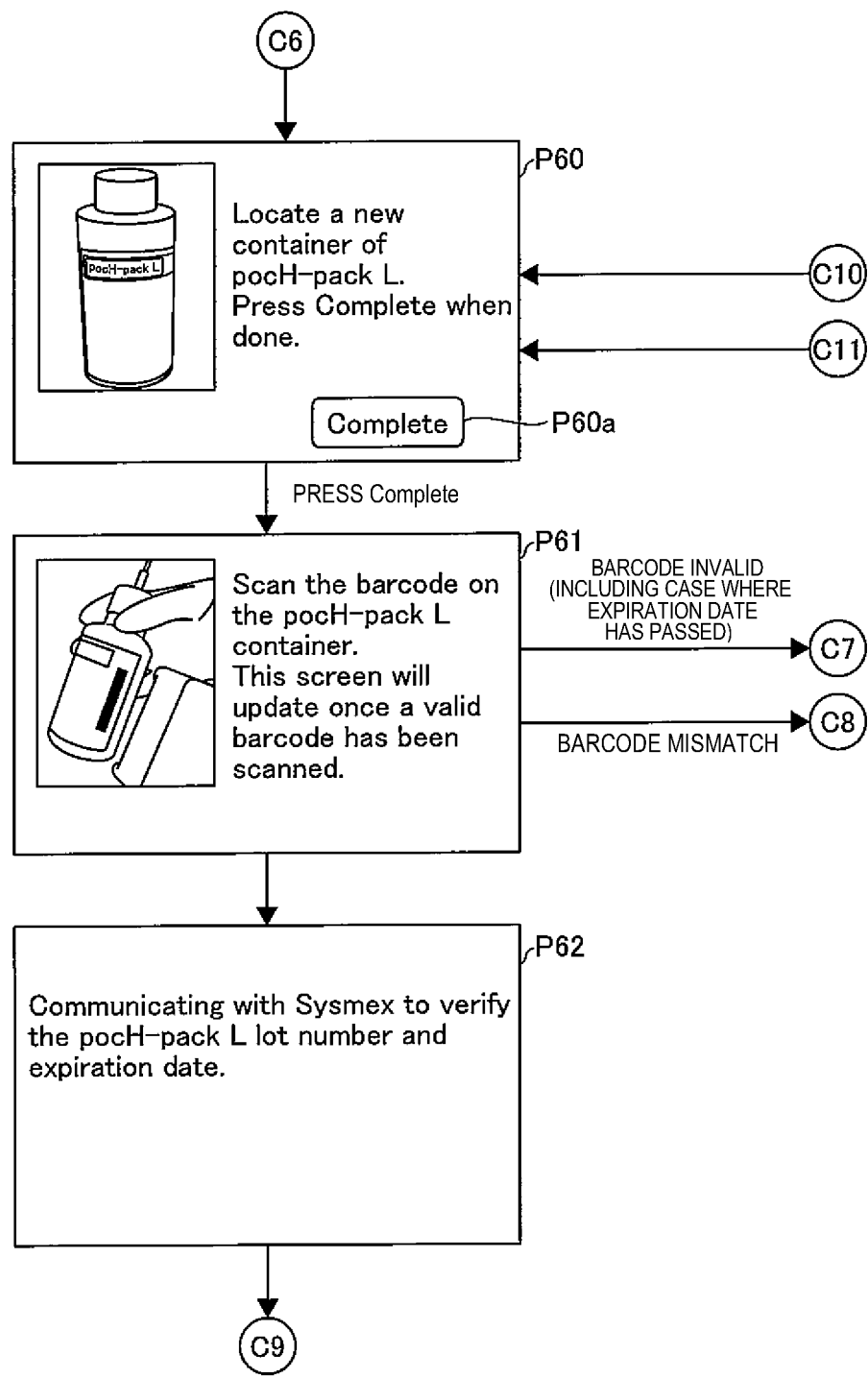
FIG. 18 is a diagram illustrating display example 4 for setting a reagent.

As illustrated in FIG. 17, screen P57 shows a picture and an instruction on how to place the reagent container. Also, screen P57 shows Complete button P57a. When Complete button P57a is pressed, display unit 131 displays screen P58. Screen P58 shows a description to connect the reagent container and the tube together. Also, screen P58 shows Complete button P58a. When Complete button P58a is pressed, display unit 131 displays screen P59. Thereafter, as illustrated in FIG. 18, display unit 131 displays screen P60.

Screen P60 shows a picture and an instruction on how to set a container of a hemolyzer used to analyze a specimen. Also, screen P60 shows Complete button P60a. When Complete button P60a is pressed, display unit 131 displays screen P61. Screen P61 shows a picture and an instruction on how to read a barcode attached on the container of the hemolyzer. When the barcode is correctly read, display unit 131 displays screen P62. If a barcode is invalid, including the case where the expiration date has passed, display unit 131 displays screen P63 (see FIG. 19). If the barcode does not match, display unit 131 displays screen P64 (see FIG. 19).

While screen P62 is being displayed, connection is established to server 200, and whether or not the reagent can be used is checked. Thereafter, display unit 131 displays screen P66 (see FIG. 20).

Figure 19:
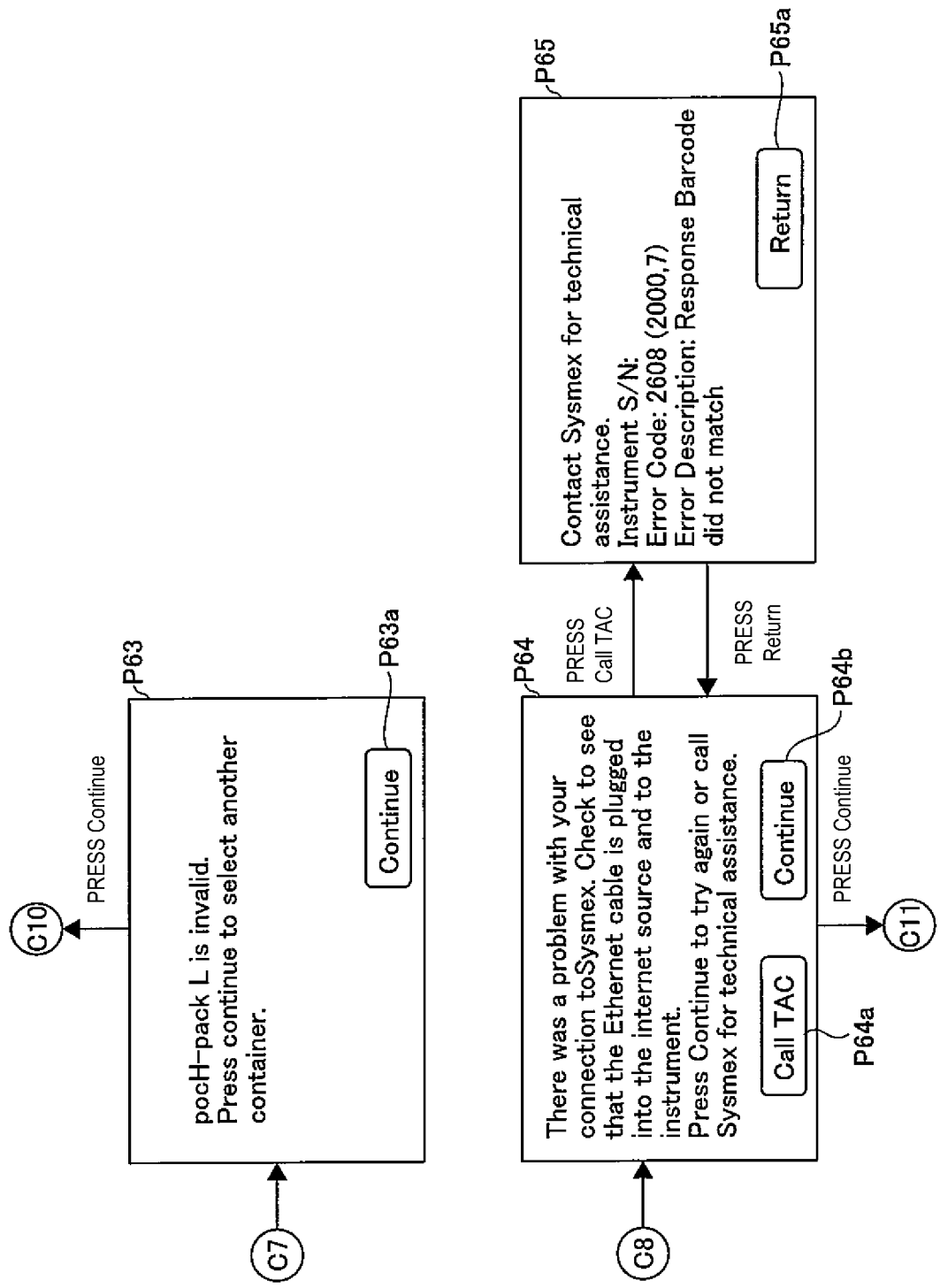
FIG. 19 is a diagram illustrating display example 5 for setting a reagent.

As illustrated in FIG. 19, screen P63 shows a description that the reagent of the read barcode is invalid. Also, screen P63 shows Continue button P63a. When Continue button P63a is pressed, display unit 131 displays screen P60 (see FIG. 18).

Screen P64 shows a description that there is a problem with the connection. Also, screen P64 shows Call TAC button P64a and Continue button P64b. When Call TAC button P64a is pressed, display unit 131 displays screen P65. When Continue button P64b is pressed, display unit 131 displays screen P60 (see FIG. 18). Screen P65 shows error details. If the user telephones to the TAC and communicates the description of screen P65, he/she can receive support smoothly. Screen P65 shows Return button P65a. When Return button P65a is pressed, display unit 131 displays screen P64.

Figure 20:
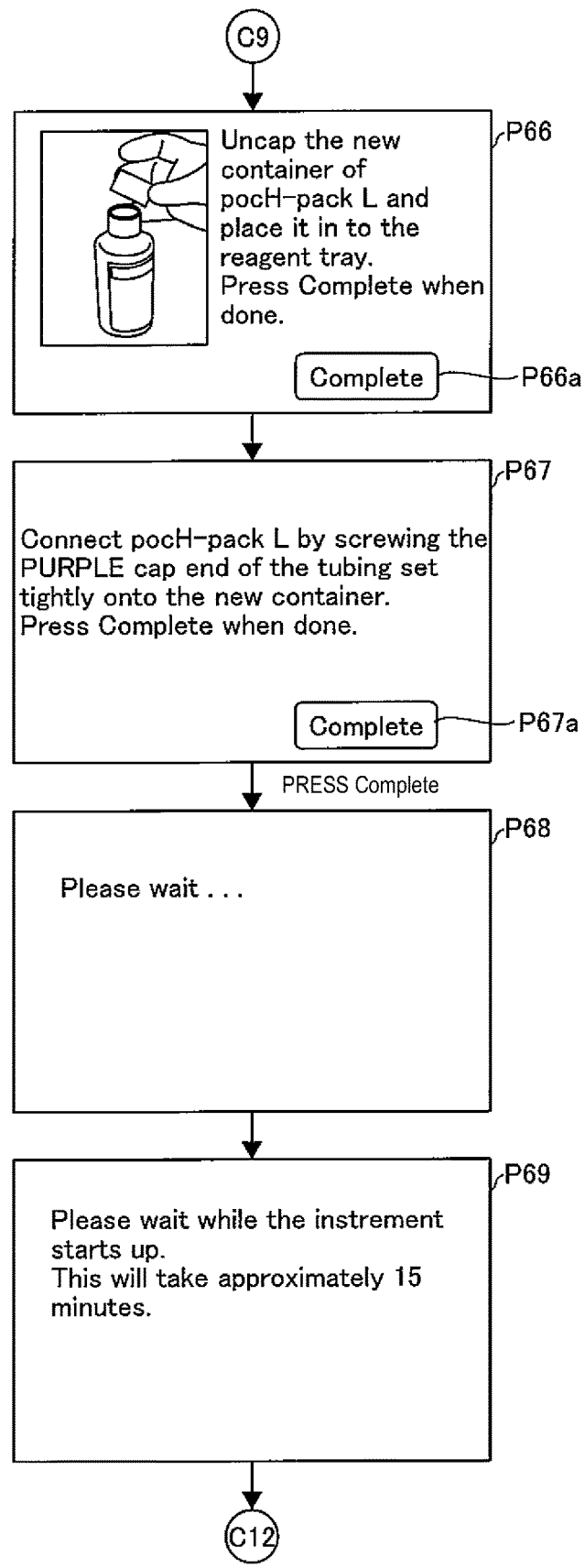
FIG. 20 is a diagram illustrating display example 6 for setting a reagent.
Figure 23:
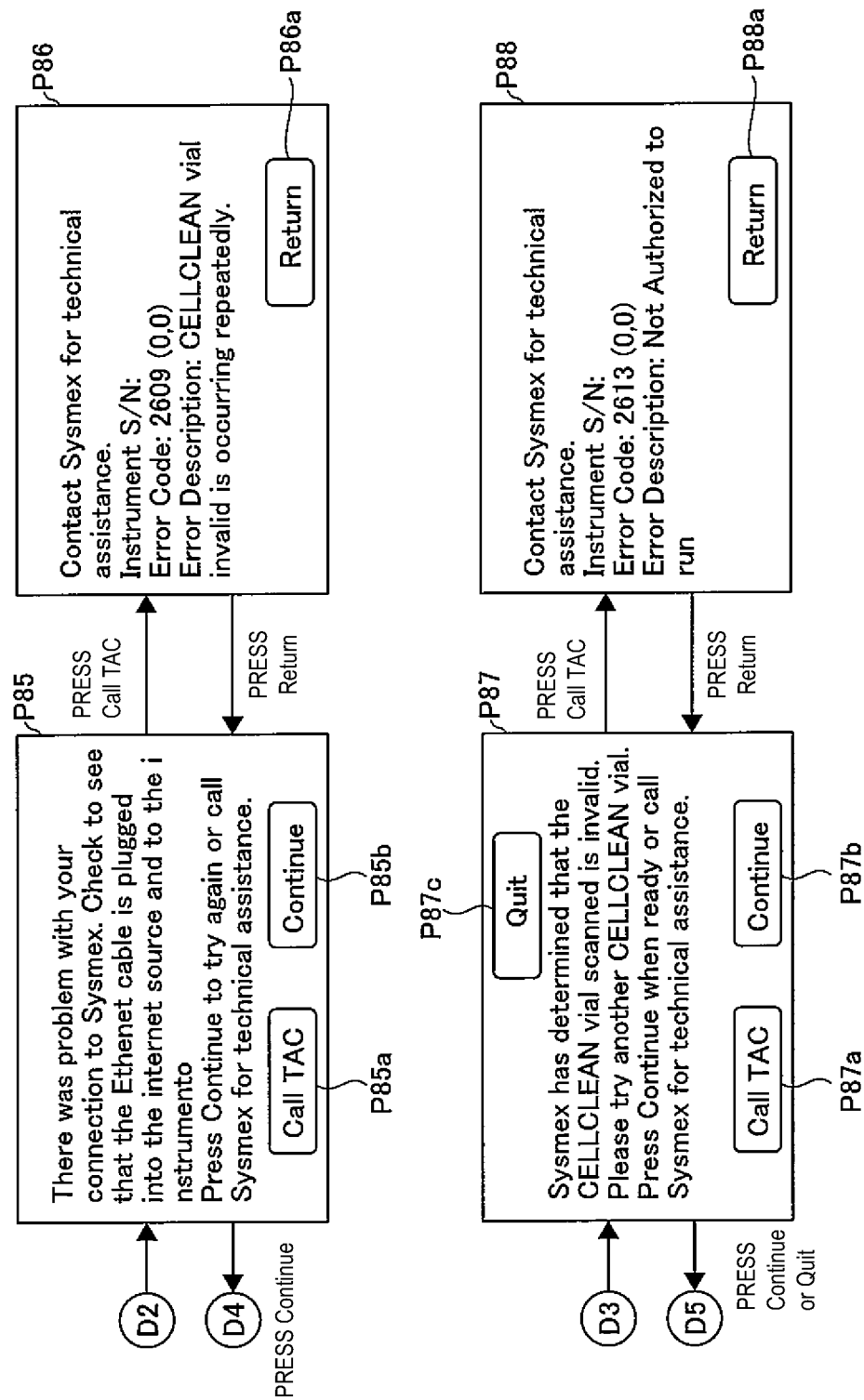
FIG. 23 is a diagram illustrating display example 2 for cleaning by CELLCLEAN.

As illustrated in FIG. 20, screen P66 shows a picture and an instruction on how to place the reagent container. Also, screen P66 shows Complete button P66a. When Complete button P66a is pressed, display unit 131 displays screen P67. Screen P67 shows a description to connect the reagent container and the tube together. Also, screen P67 shows Complete button P67a. When Complete button P67a is pressed, display unit 131 displays screen P68. Thereafter, display unit 131 displays screen P69.

Subsequently, display unit 131 displays screen P70. In addition, the diluted solution is fed to specimen analyzer 100. Thereafter, display unit 131 displays screen P71. Moreover, the hemolyzer is fed to specimen analyzer 100. Thereafter, display unit 131 displays screen P72. Finally, the screen of setting the reagent finished being displayed. Then, the screen proceeds to a screen of cleaning by CELLCLEAN.

(Display Example of Cleaning by CELLCLEAN)

With reference to FIG. 22 to FIG. 25, a display example of cleaning by CELLCLEAN is described.

As illustrated in FIG. 22, display unit 131 displays screen P81 in order to indicate the necessity of cleaning by CELLCLEAN. Screen P81 shows Continue button P81a. When Continue button P81a is pressed, display unit 131 displays screen P82. Screen P82 shows a picture and an instruction on CELLCLEAN to be used. Also, screen P82 shows Complete button P82a. When Complete button P82a is pressed, display unit 131 displays screen P83.

Screen P83 shows a picture and an instruction on how to open a door and insert an adapter. Also, screen P83 shows Complete button P83a. When Complete button P83a is pressed, display unit 131 displays screen P84. Screen P84 shows a description to read a barcode attached on the container of CELLCLEAN. Also, screen P84 shows Quit button P84a. When the barcode is correctly read, display unit 131 displays screen P89 (see FIG. 24). In the case where the expiration date has passed, display unit 131 displays screen P85 (see FIG. 23). If the barcode does not match, display unit 131 displays screen P87 (see FIG. 23). When Quit button P84a is pressed, display unit 131 displays screen P91 (see FIG. 24).

Screen P85 shows a description that there is a problem with the connection. Also, screen P85 shows Call TAC button P85a and Continue button P85b. When Call TAC button P85a is pressed, display unit 131 displays screen P86. When Continue button P85b is pressed, display unit 131 displays screen P84 (see FIG. 22). Screen P86 shows error details. If the user telephones to the TAC and communicates the description of screen P86, he/she can receive support smoothly. Screen P86 shows Return button P86a. When Return button P86a is pressed, display unit 131 displays screen P85.

Screen P87 shows a description that CELLCLEAN is invalid. Also, screen P87 shows Call TAC button P87a, Continue button P87b, and Quit button P87c. When Call TAC button P87a is pressed, display unit 131 displays screen P88. When Continue button P87b or Quit button P87c is pressed, display unit 131 displays screen P84 (see FIG. 22). Screen P88 shows error details. If the user telephones to the TAC and communicates the description of screen P88, he/she can receive support smoothly. Screen P88 shows Return button P88a. When Return button P88a is pressed, display unit 131 displays screen P87.

Figure 24:
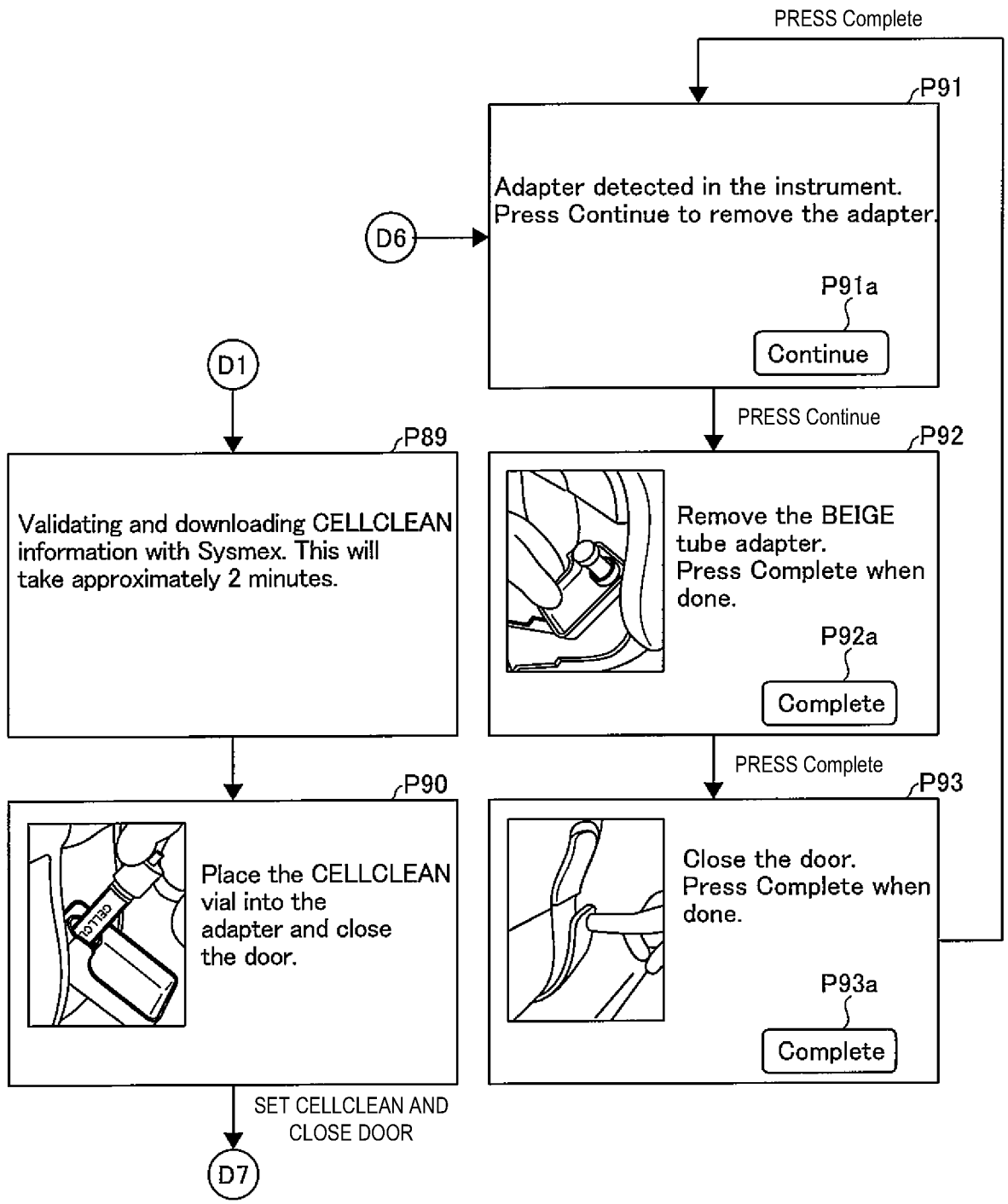
FIG. 24 is a diagram illustrating display example 3 for cleaning by CELLCLEAN.

As illustrated in FIG. 24, screen P89 shows a description on validation and download of CELLCLEAN information. Thereafter, display unit 131 displays screen P90. Screen P90 shows a picture and an instruction on how to place CELLCLEAN. After CELLCLEAN is placed and the door is closed, display unit 131 displays screen P94 (see FIG. 25).

Screen P91 shows a description that the adapter is set and Continue button P91a. When Continue button P91a is pressed, display unit 131 displays screen P92. Screen P92 shows a picture and an instruction on how to remove the adapter. Also, screen P92 shows Complete button P92a. When Complete button P92a is pressed, display unit 131 displays screen P93. Screen P93 shows a picture and an instruction on how to close the door. Also, screen P93 shows Complete button P93a. When Complete button P93a is pressed, display unit 131 displays screen P91.

Figure 25:
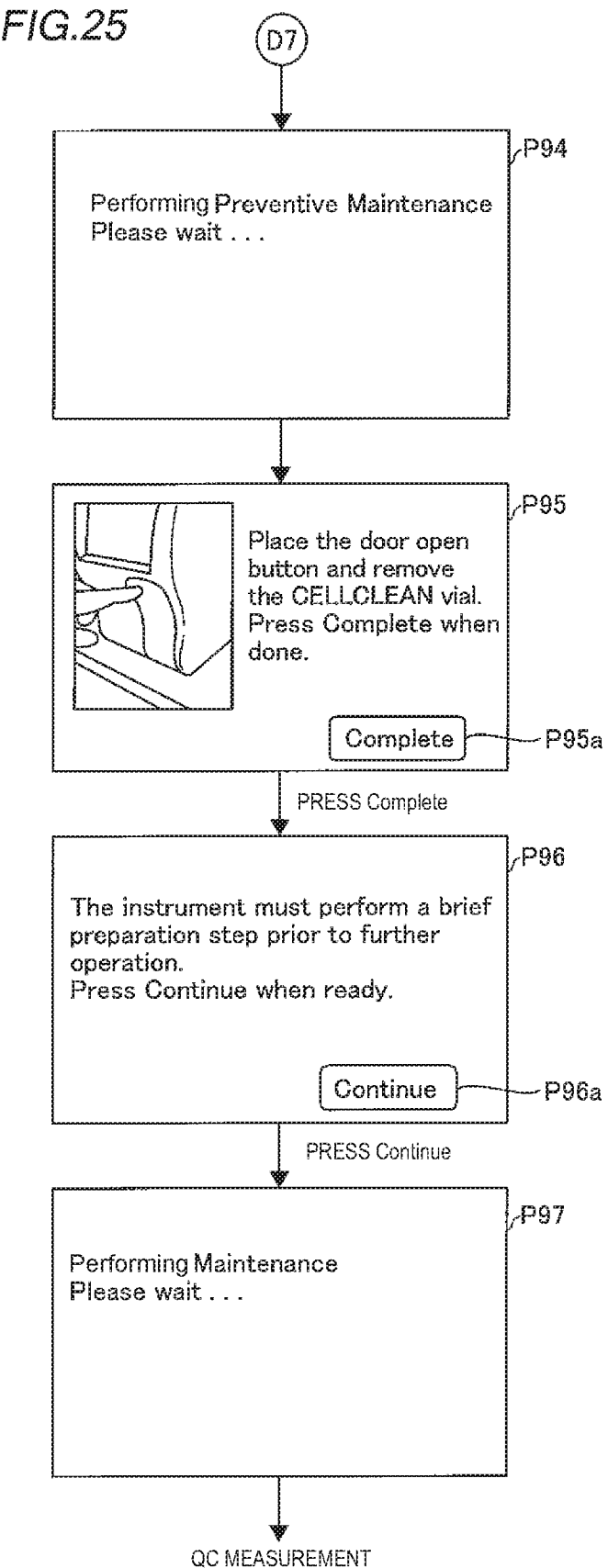
FIG. 25 is a diagram illustrating display example 4 for cleaning by CELLCLEAN.

As illustrated in FIG. 25, display unit 131 displays screen P94. Also, CELLCLEAN cleans the inside of specimen analyzer 100. Thereafter, display unit 131 displays screen P95. Screen P95 shows a picture and an instruction on how to remove the container of CELLCLEAN from specimen analyzer 100. Also, screen P95 shows Complete button P95a. When Complete button P95a is pressed, display unit 131 shows screen P96.

Screen P96 shows a description to prepare specimen analyzer 100 and Continue button P96a. When Continue button P96a is pressed, display unit 131 displays screen P97. Also, the preparation of specimen analyzer 100 proceeds. Finally, the screen of cleaning by CELLCLEAN finishes being displayed. Then, the screen proceeds to a screen of QC measurement.

(Display Example at QC Measurement)

With reference to FIG. 26 to FIG. 32, a display example at QC measurement is described.

Figure 26:
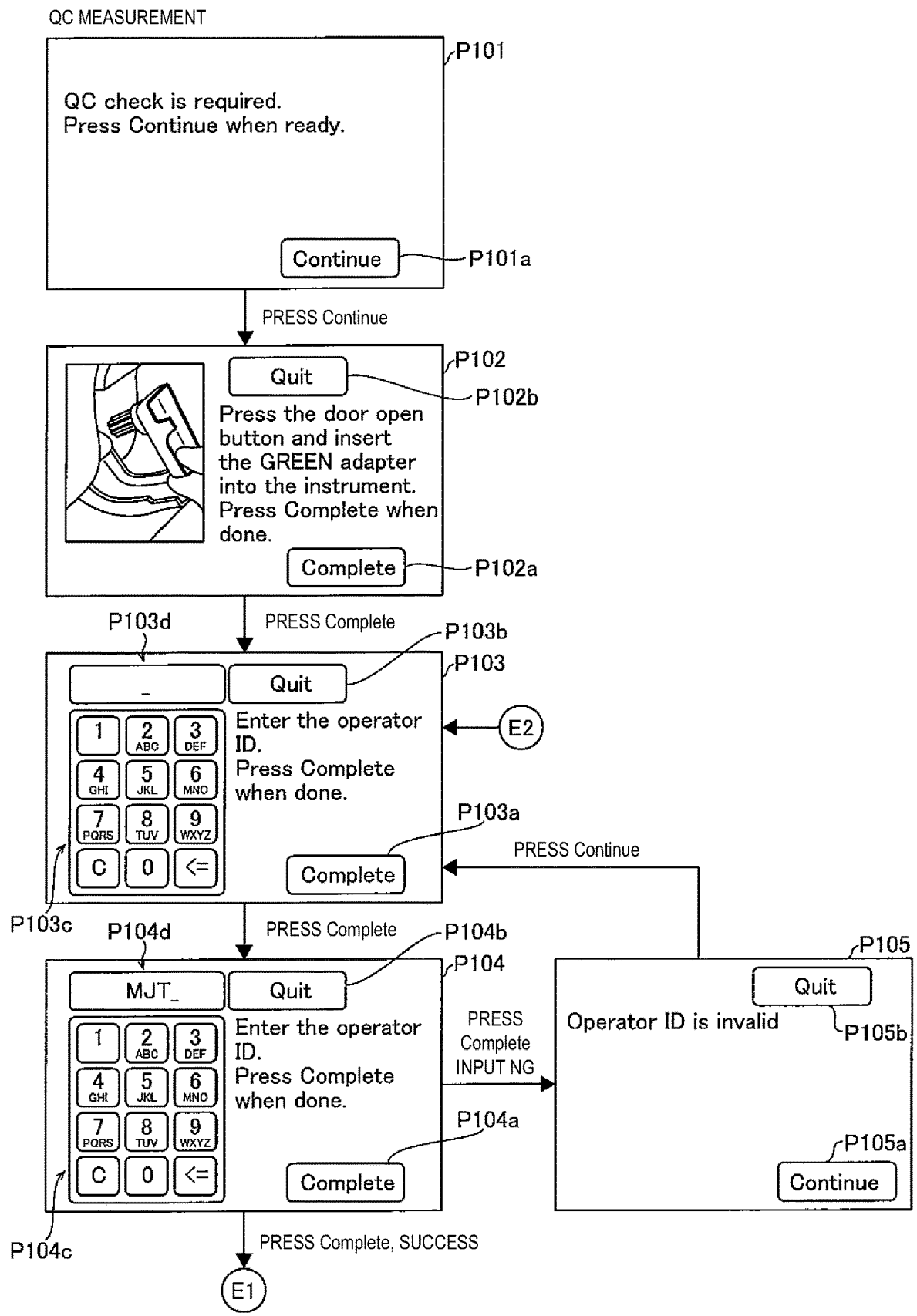
FIG. 26 is a diagram illustrating display example 1 for QC measurement.

As illustrated in FIG. 26, display unit 131 displays screen P101 in order to indicate the necessity of QC (Quality Control) measurement. Screen P101 shows Continue button P101a. When Continue button P101a is pressed, display unit 131 displays screen P102. Screen P102 shows a picture and an instruction on how to open the door and insert the adapter. Also, screen P102 shows Complete button P102a. When Complete button P102a is pressed, display unit 131 displays screen P103.

Screen P103 shows a description to input the ID of the operator. Also, screen P103 shows Complete button P103a, Quit button P103b, input buttons P103c, and input region P103d. When input buttons P103c are operated, input region P103d displays inputted characters. The ID of the operator can be set using, for example, any one to three alphabetical letters. Also, the ID of the operator may be different for each of the High, Low, and Normal QC reagents.

When Complete button P103a is pressed, display unit 131 displays screen P104. In the example of FIG. 26, the string "MJT" is inputted as the ID of the operator. Screen P104 shows Complete button P104a, Quit button P104b, input buttons P104c, and input region P104d. When the pressing of Complete button P104a succeeds, display unit 131 displays screen P106 (see FIG. 27). When Complete button P104a is pressed but the input is NG, display unit 131 displays screen P105.

Screen P105 shows a description that the operator ID is invalid, Continue button P105a, and Quit button P105b. When Continue button P105a is pressed, display unit 131 displays screen P103.

Figure 27:
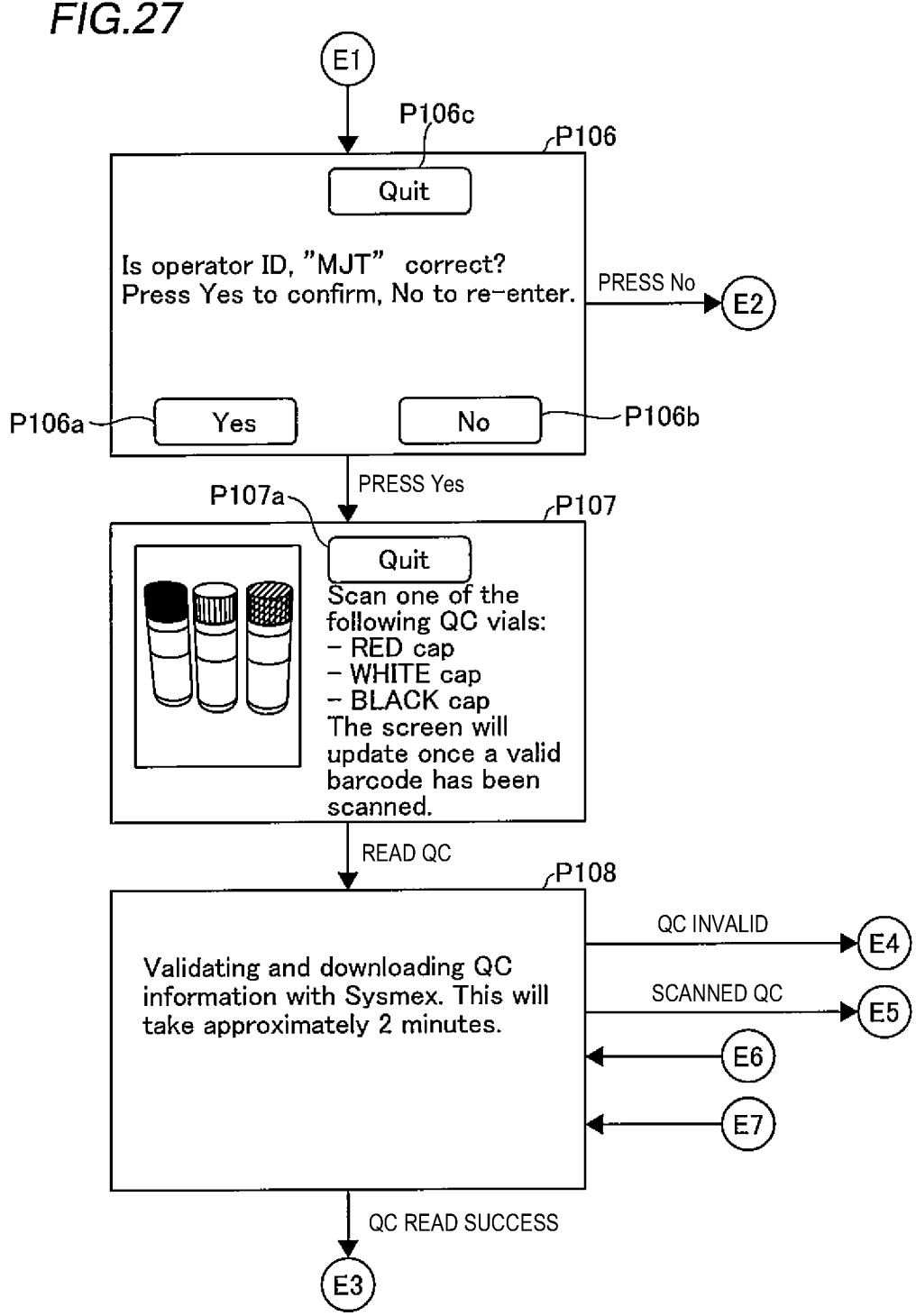
FIG. 27 is a diagram illustrating display example 2 for QC measurement.

As illustrated in FIG. 27, screen P106 shows a question asking whether or not the operator ID is correct, Yes button P106a and No button P106b, and Quit button P106c. When No button P106b is pressed, display unit 131 displays screen P103. When Yes button P106a is pressed, display unit 131 displays screen P107.

Screen P107 shows a picture and an instruction on how to read a barcode of a High QC reagent. Also, screen P107 shows Quit button P107a. When the barcode of the QC reagent is read, display unit 131 displays screen P108. Screen P108 shows a description on validation and download of information on the QC reagent. Once information on the QC reagent is downloaded from server 200, a range of a normal value of the measurement value of the QC reagent is obtained.

Figure 28:
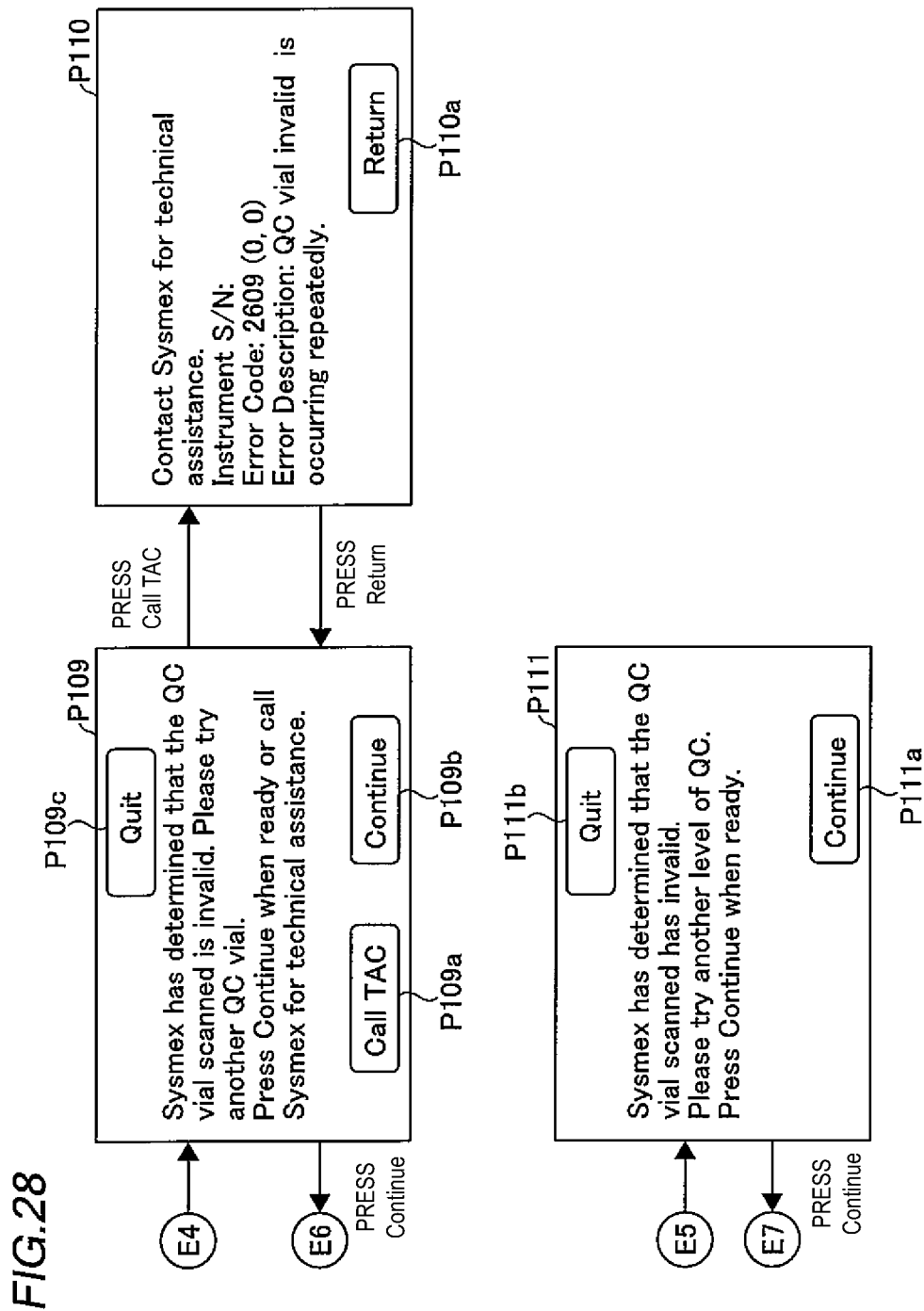
FIG. 28 is a diagram illustrating display example 3 for QC measurement.
Figure 29:
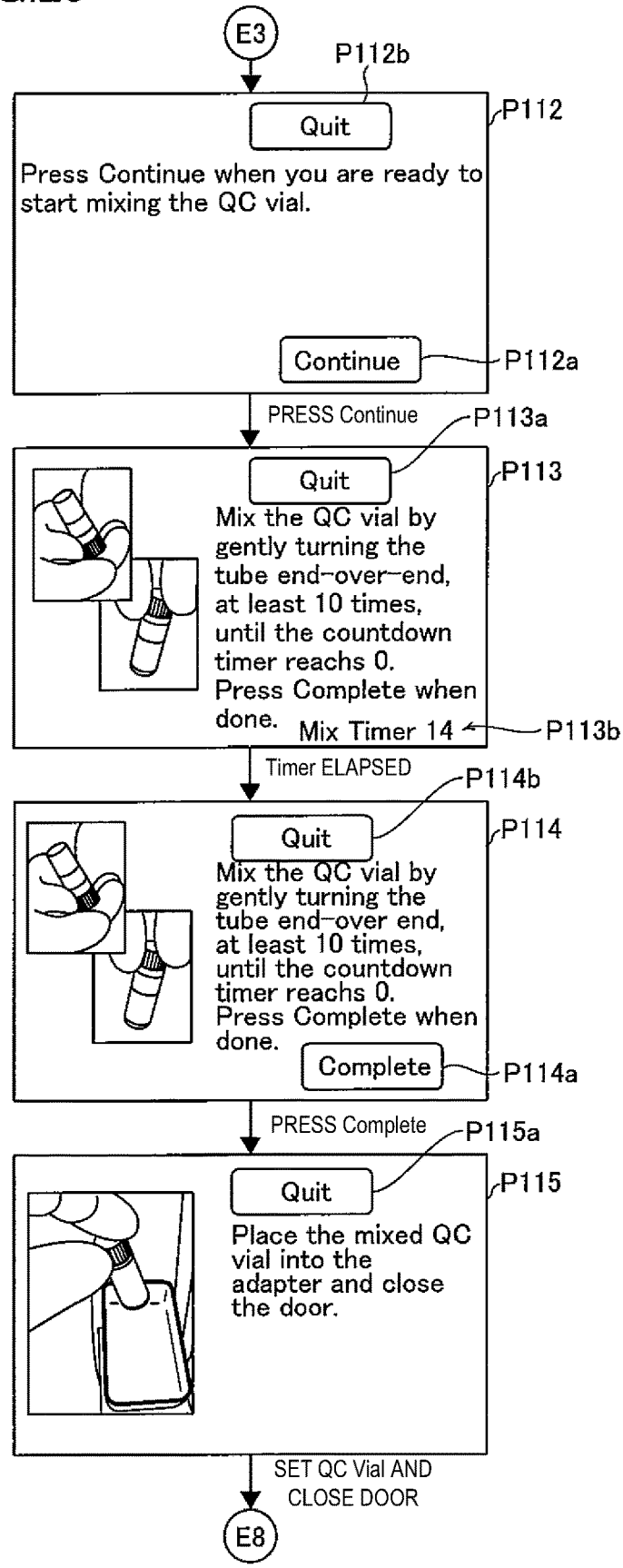
FIG. 29 is a diagram illustrating display example 4 for QC measurement.

When the validation and download of information on the QC reagent succeed, display unit 131 displays screen P112 (see FIG. 29). When the QC reagent is determined as invalid, display unit 131 displays screen P109 (see FIG. 28). When the QC reagent is determined as a scanned QC reagent, display unit 131 displays screen P111 (see FIG. 28).

As illustrated in FIG. 28, screen P109 shows a description that the QC reagent is invalid. Also, screen P109 shows Call TAC button P109a, Continue button P109b, and Quit button P109c. When Call TAC button P109a is pressed, display unit 131 displays screen P110. When Continue button P109b is pressed, display unit 131 displays screen P108 (see FIG. 27). Screen P110 shows error details. If the user telephones to the TAC and communicates the description of screen P110, he/she can receive support smoothly. Screen P110 shows Return button P110a. When Return button P110a is pressed, display unit 131 displays screen P109.

Screen P111 shows a description that the QC reagent is invalid. Also, screen P111 shows Continue button P111a and Quit button P111b. When Continue button P111a is pressed, display unit 131 displays screen P108 (see FIG. 27).

As illustrated in FIG. 29, screen P112 shows a description to start stirring the QC reagent, Continue button P112a, and Quit button P112b. When Continue button P112a is pressed, display unit 131 displays screen P113. Screen P113 shows a description to stir the QC reagent, Quit button P113a, and timer P113b. Timer P113b is displayed counting down from 15 sec, for example. When the time counted down by timer P113b has elapsed, display unit 131 displays screen P114.

Screen P114 shows Complete button P114a and Quit button P114b. When Complete button P114a is pressed, display unit 131 displays screen P115. Screen P115 shows a picture and an instruction on how to set the QC reagent. Also, screen P115 shows Quit button P115a.

Figure 30:
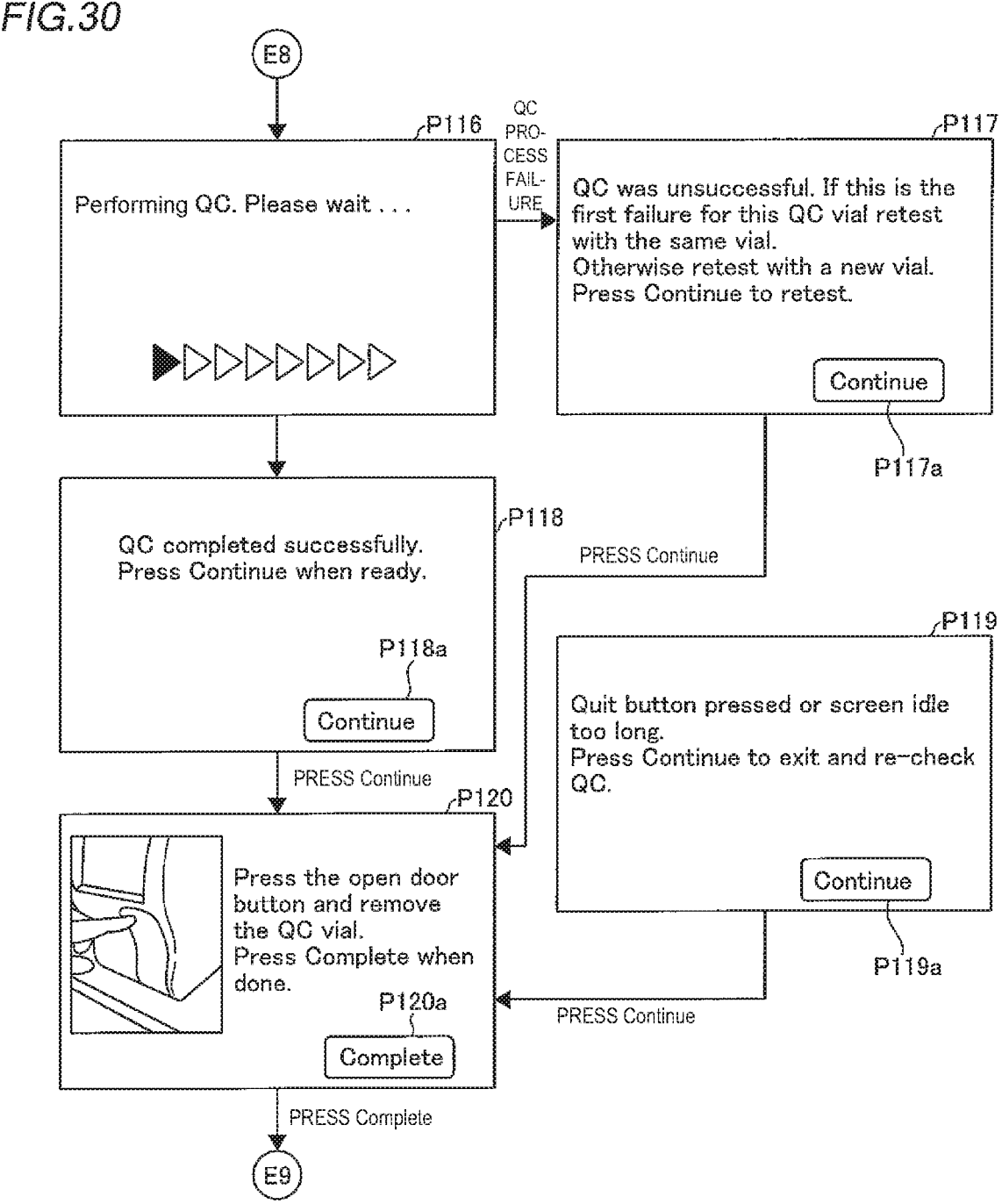
FIG. 30 is a diagram illustrating display example 5 for QC measurement.

When the QC reagent is set and the door is closed, display unit 131 displays screen P116, as illustrated in FIG. 30. Also, measurement of QC reagent is performed. When the treatment of the QC reagent fails, display unit 131 displays screen P117. Screen P117 shows a description to perform measurement again. Also, screen P117 shows Continue button P117a. When Continue button P117a is pressed, display unit 131 displays screen P120. When the measurement of the QC reagent finishes normally, display unit 131 displays screen P118. Screen P118 shows Continue button P118a. When Continue button P118a is pressed, display unit 131 displays screen P120.

Here, display unit 131 displays screen P119 when the Quit button is pressed in any of the screens, or when a predetermined time period has elapsed with the screen left unoperated. Screen P119 shows Continue button P119a. When Continue button P119a is pressed, display unit 131 displays screen P120.

Screen P120 shows a picture and an instruction on how to remove the container of the QC reagent from specimen analyzer 100. Also, screen P120 shows Complete button P120a. When Complete button P120a is pressed, display unit 131 displays screen P121 (see FIG. 31).

Figure 31:
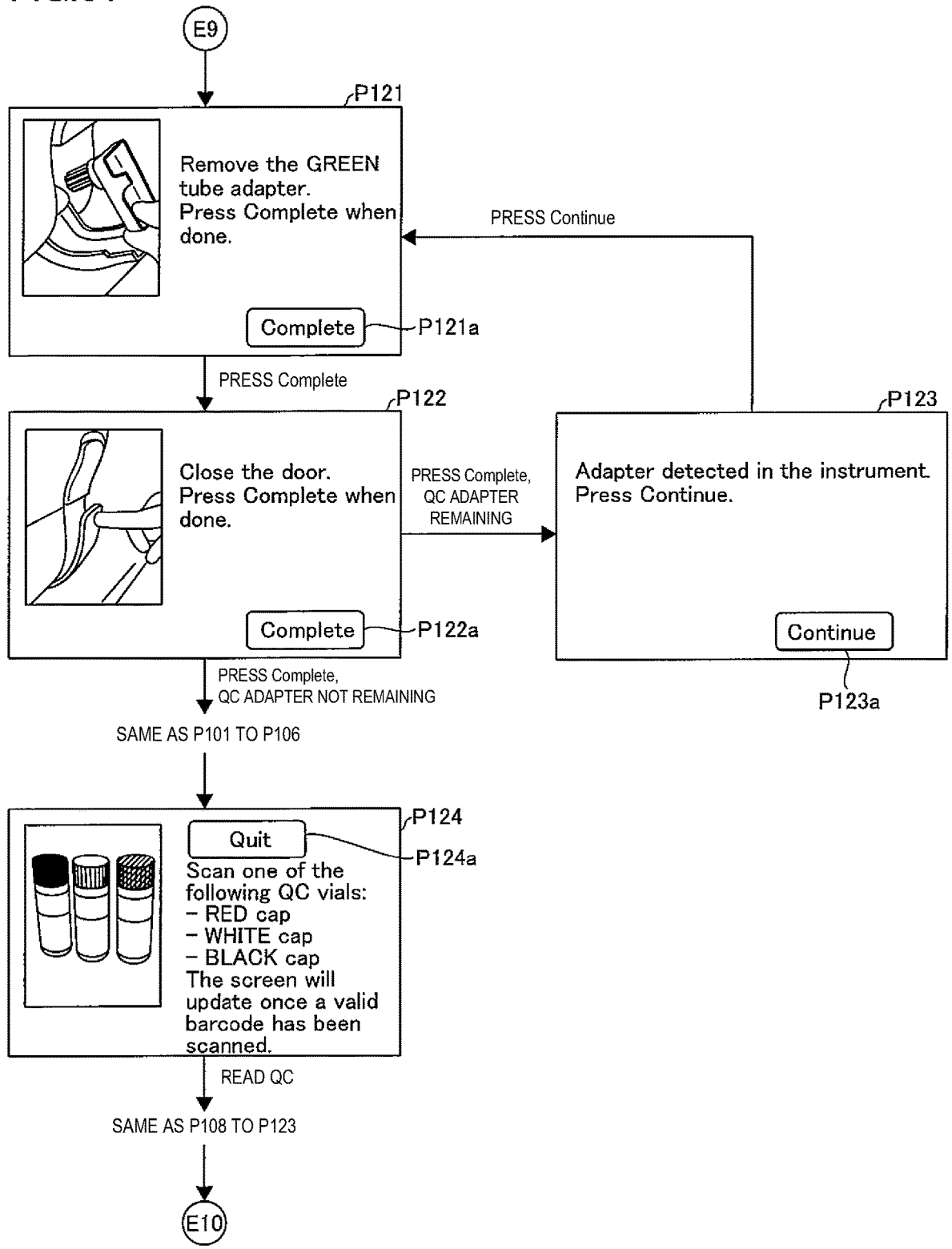
FIG. 31 is a diagram illustrating display example 6 for QC measurement.
Figure 32:
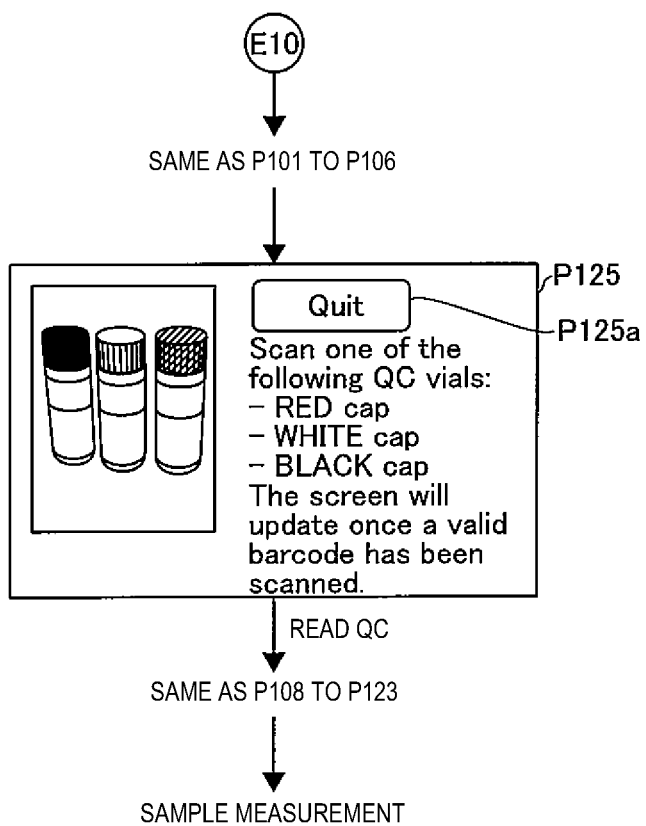
FIG. 32 is a diagram illustrating display example 7 for QC measurement.

As illustrated in FIG. 31, screen P121 shows a picture and an instruction on how to remove the adapter from specimen analyzer 100. In addition, screen P121 shows Complete button P121a. When Complete button P121a is pressed, display unit 131 displays screen P122. Screen P122 shows a picture and an instruction on how to close the door. Also, screen P122 shows Complete button P122a. When Complete button P122a is pressed, the measurement process of the High QC reagent finishes. Thereafter, a measurement process of a Low QC reagent is performed.

If the QC adapter is remaining when Complete button P122a is pressed, display unit 131 displays screen P123. Screen P123 shows Continue button P123a. When Continue button P123a is pressed, display unit 131 displays screen P121.

When the measurement process of the Low QC reagent starts, display unit 131 displays screens similar to screens P101 to P106, and similar processes are performed. Thereafter, display unit 131 displays screen P124. Screen P124 displays a picture and an instruction on how to read a barcode of the Low QC reagent. Also, screen P124 shows Quit button P124a. When the barcode of the QC reagent is read, display unit 131 displays screens similar to screen P108 to P123, and similar processes are performed. Finally, the measurement process of the Low QC reagent finishes. Thereafter, a measurement process of a Normal QC reagent is performed.

When the measurement process of the Normal QC reagent starts, display unit 131 displays screens similar to screen P101 to P106, and similar processes are performed. Thereafter, display unit 131 displays screen P125. Screen P125 displays a picture and an instruction on how to read a barcode of the Normal QC reagent. Also, screen P125 shows Quit button P125a. When the barcode of the QC reagent is read, display unit 131 displays screens similar to screen P108 to P123, and similar processes are performed. Finally, the measurement process of the Normal QC reagent finishes. Then, the screen of QC measurement stops being displayed. Subsequently, the screen proceeds to a screen of sample measurement. Thus, the preparation for sample measurement is done.

(Display Example at Sample Measurement)

With reference to FIG. 33 to FIG. 40, display example at sample measurement is described.

Figure 33:
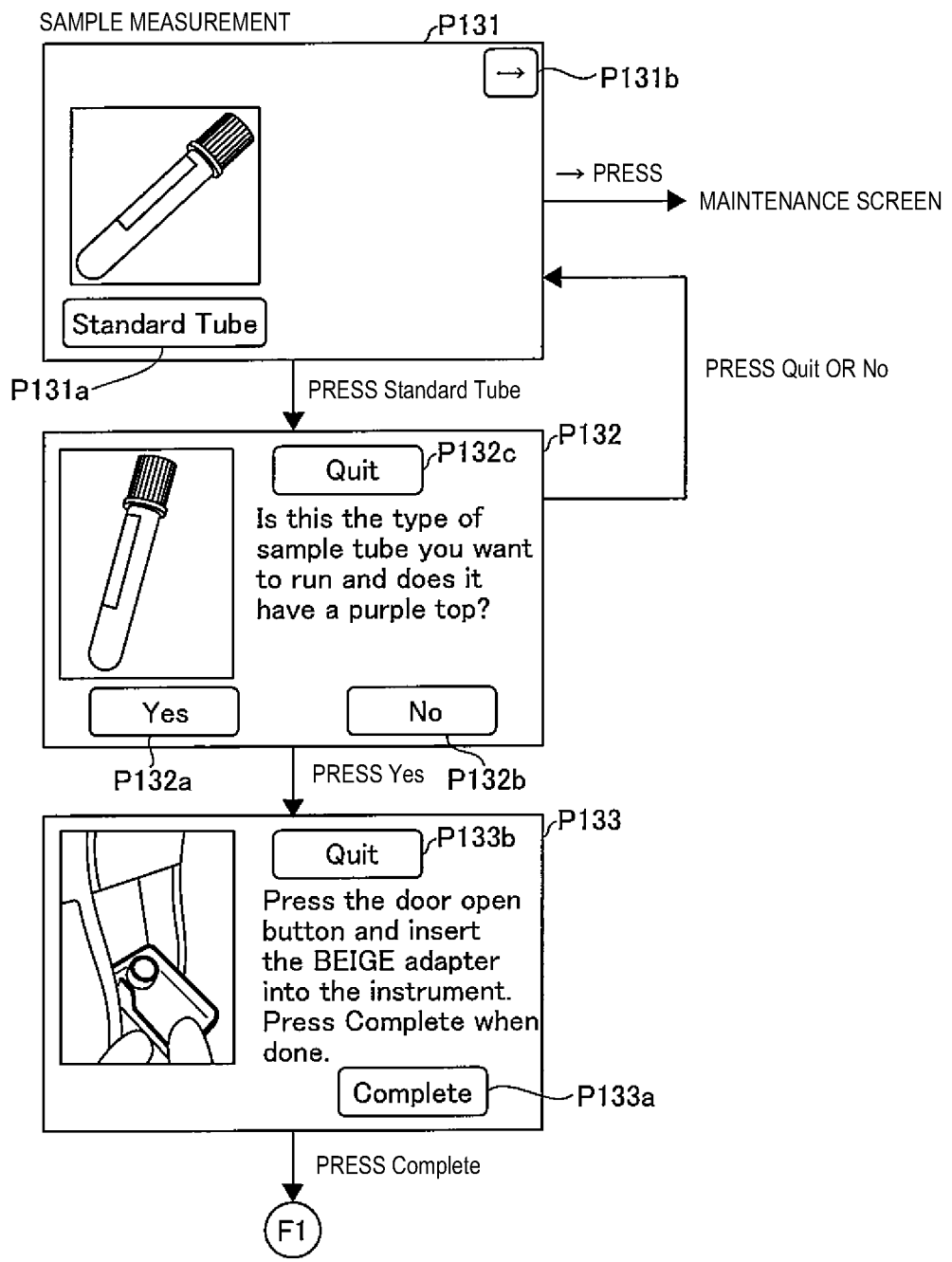
FIG. 33 is a diagram illustrating display example 1 for sample measurement.

As illustrated in FIG. 33, display unit 131 displays screen P131 for measuring the sample of the patient as the specimen. In the case of waiting for preparation of sample measurement, display unit 131 displays screen P131. Screen P131 shows Standard Tube button P131a and arrow button P131b. When arrow button P131b is pressed, display unit 131 displays screen P160 for maintenance (see FIG. 41). When Standard Tube button P131a is pressed, display unit 131 displays screen P132. Screen P132 shows a question asking whether or not the sample container is correct, Yes button P132a and No button P132b, and Quit button P132c. When No button P132b or Quit button P132c is pressed, display unit 131 displays screen P131. When Yes button P132a is pressed, display unit 131 displays screen P133.

Screen P133 shows a picture and an instruction on how to open the door and insert the adapter. Also, screen P133 shows Complete button P133a and Quit button P133b. When Complete button P133a is pressed, display unit 131 displays screen P134 (see FIG. 34).

Figure 34:
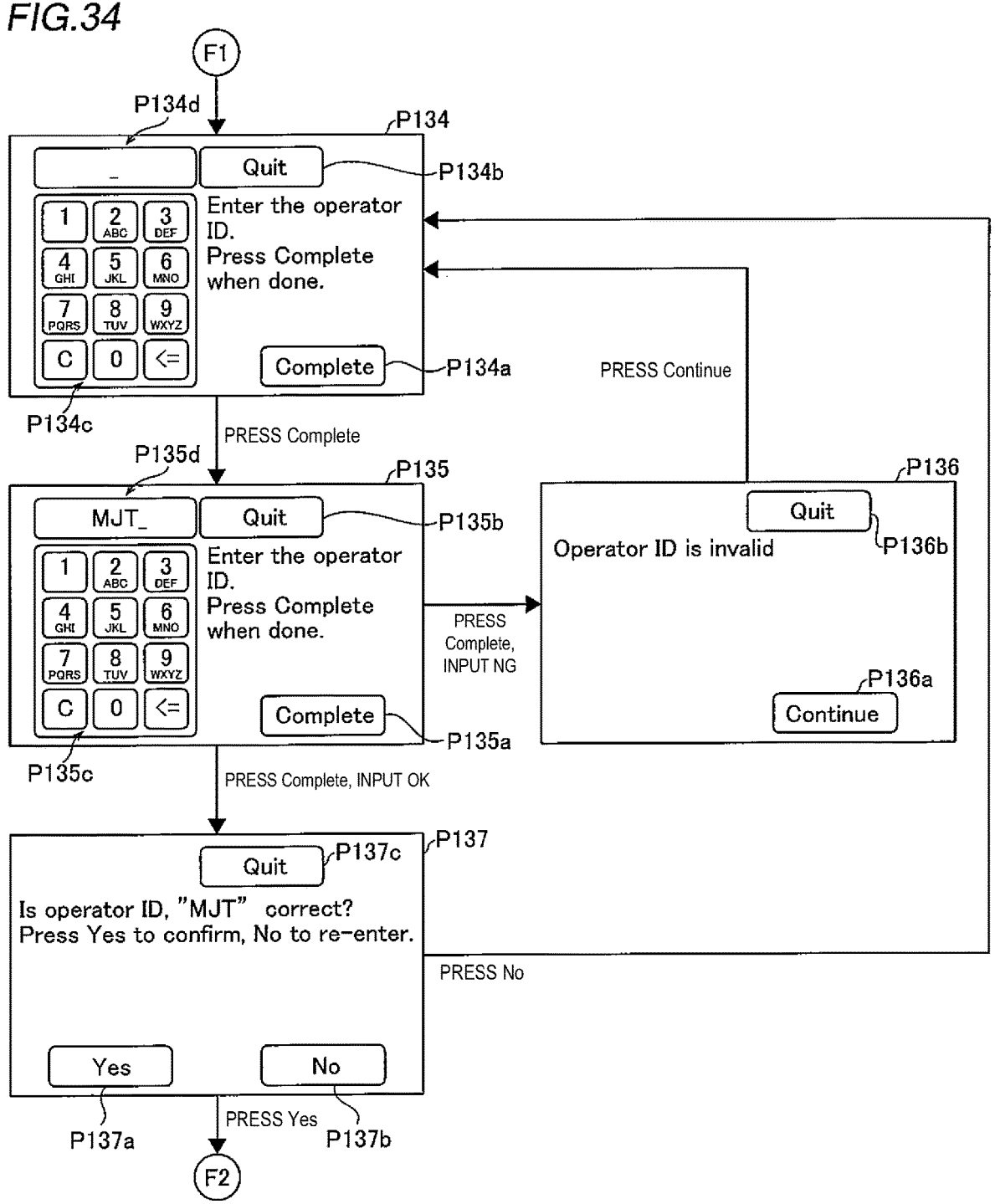
FIG. 34 is a diagram illustrating display example 2 for sample measurement.

As illustrated in FIG. 34, screen P134 shows a description for inputting the ID of the operator. Also, screen P134 shows Complete button P134a, Quit button P134b, input buttons P134c, and input region P134d. When input buttons P134c are operated, input region P134d displays inputted characters. The ID of the operator can be set using, for example, any one to three alphabetical letters.

When Complete button P134a is pressed, display unit 131 displays screen P135. In the example of FIG. 34, the string "MJT" is inputted as the ID of the operator. Screen P135 shows Complete button P135a, Quit button P135b, input buttons P135c, and input region P135d. When Complete button P135a is pressed and the input is OK, display unit 131 displays screen P137. When Complete button P135a is pressed but the input is NG, display unit 131 displays screen P136.

Screen P136 shows a description that the operator ID is invalid, Continue button P136a, and Quit button P136b. When Continue button P136a is pressed, display unit 131 displays screen P134.

Screen P137 shows a question asking whether or not the operator ID is correct, Yes button P137a and No button P137b, and Quit button P137c. When No button P137b is pressed, display unit 131 displays screen P134. When Yes button P137a is pressed, display unit 131 displays screen P138 (see FIG. 35).

Figure 35:
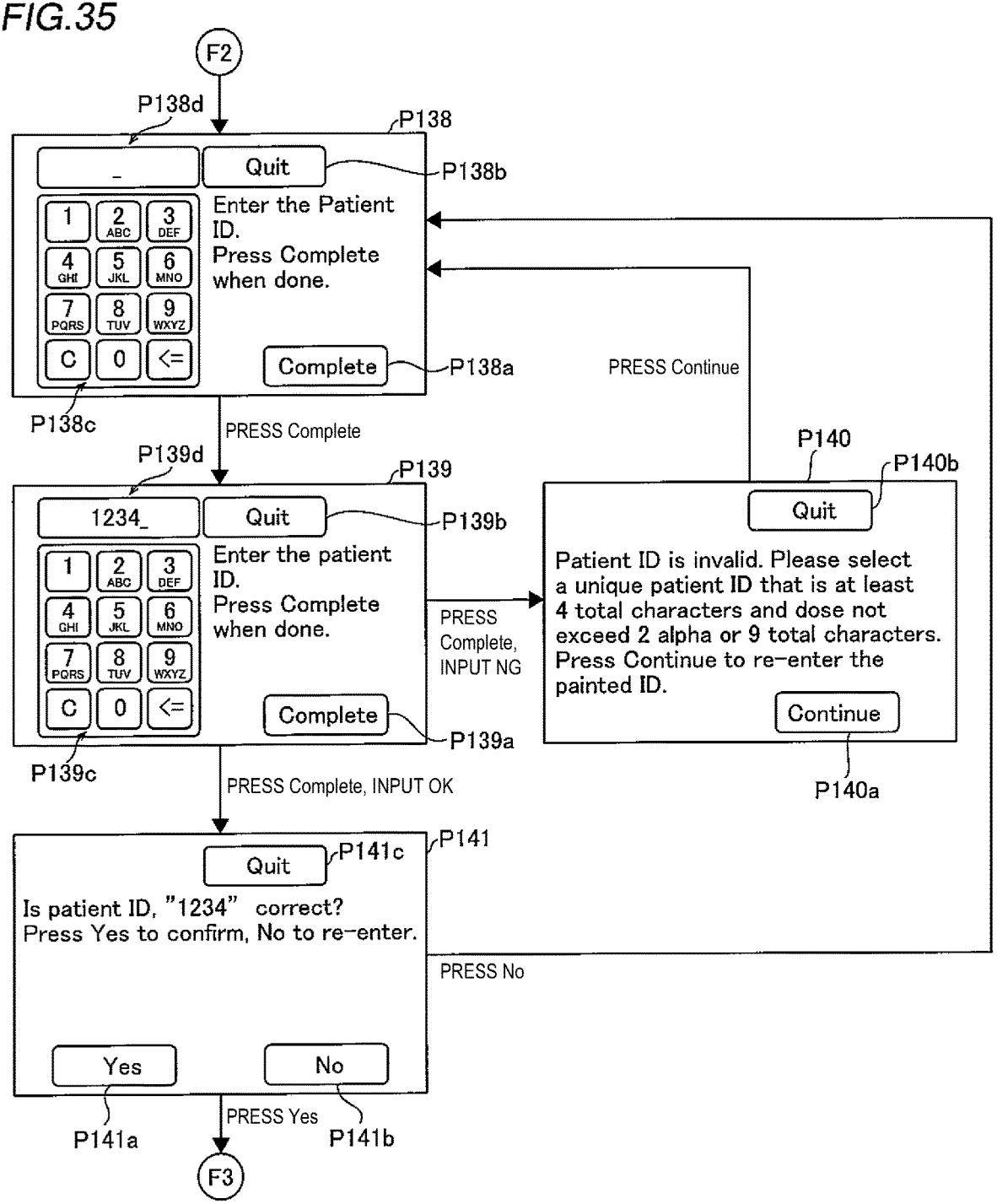
FIG. 35 is a diagram illustrating display example 3 for sample measurement.

As illustrated in FIG. 35, screen P138 shows a description for inputting the ID of the operator. Also, screen P138 shows Complete button P138a, Quit button P138b, input buttons P138c, and input region P138d. When input buttons P138c are operated, input region P138d displays inputted characters. The ID of the patient can be set using, for example, any four or more characters. The ID of the patient can be set using four to nine characters. Also, the ID of the patient can include zero to two alphabetical letters. In addition, the ID of the patient can include numbers from zero to eight characters.

When Complete button P138a is pressed, display unit 131 displays screen P139. In the example of FIG. 35, the string "1234" is inputted as the ID of the patient. Screen P139 shows Complete button P139a, Quit button P139b, input buttons P139c, and input region P139d. When Complete button P139a is pressed and the input is OK, display unit 131 displays screen P141. When Complete button P139a is pressed but the input is NG, display unit 131 displays screen P140.

Screen P140 shows a description that the patient ID is invalid, Continue button P140a, and Quit button P140b. When Continue button P140a is pressed, display unit 131 displays screen P138.

Screen P141 shows a question asking whether or not patient ID is correct, Yes button P141a and No button P141b, and Quit button P141c. When No button P141b is pressed, display unit 131 displays screen P138. When Yes button P141a is pressed, display unit 131 displays screen P142 (see FIG. 36).

Figure 36:
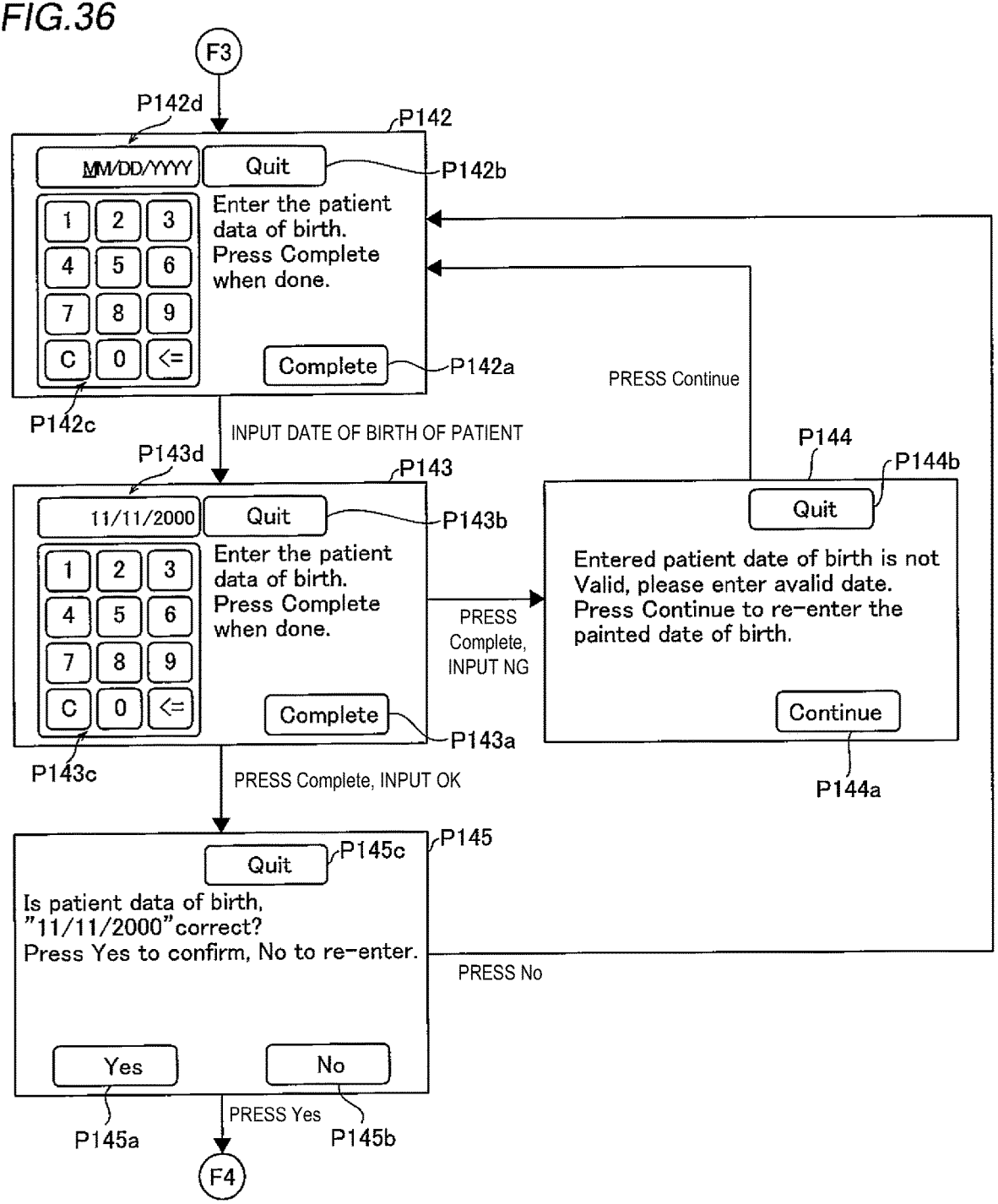
FIG. 36 is a diagram illustrating display example 4 for sample measurement.

As illustrated in FIG. 36, screen P142 shows a description for inputting the date of birth of the patient. Also, screen P142 shows Complete button P142a, Quit button P142b, input buttons P142c, and input region P142d. When input buttons P142c are operated, input region P142d displays inputted characters.

When Complete button P142a is pressed, display unit 131 displays screen P143. In the example of FIG. 36, "11/11/2000" is inputted as the date of birth of the patient. Screen P143 shows Complete button P143a, Quit button P143b, input buttons P143c, and input region P143d. When the Complete button P143a is pressed and the input is OK, display unit 131 displays screen P145. When Complete button P143a is pressed but the input is NG, display unit 131 displays screen P144.

Screen P144 shows a description that the date of birth of the patient is invalid, Continue button P144a, and Quit button P144b. When Continue button P144a is pressed, display unit 131 displays screen P142.

Screen P145 shows a question asking whether or not the date of birth of the patient is correct, Yes button P145a and No button P145b, and Quit button P145c. When No button P145b is pressed, display unit 131 displays screen P142. When Yes button P145a is pressed, display unit 131 displays screen P146 (see FIG. 37).

Figure 37:
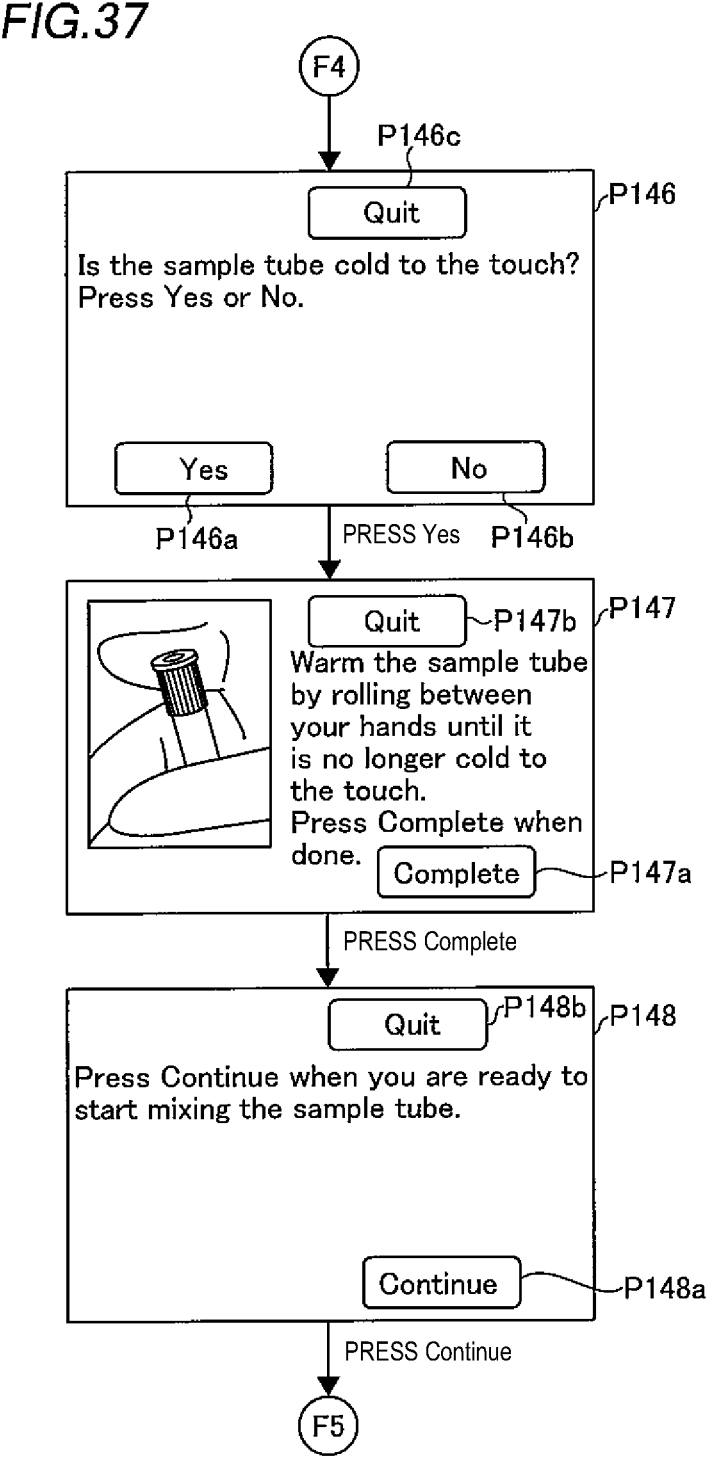
FIG. 37 is a diagram illustrating display example 5 for sample measurement.

As illustrated in FIG. 37, screen P146 shows a question asking whether or not the sample container is cold, Yes button P146a and No button P146b, and Quit button P146c. When Yes button P146a is pressed, display unit 131 displays screen P147. Screen P147 shows a picture and an instruction on how to warm the sample container. Also, screen P147 shows Complete button P147a and Quit button P147b. When Complete button P147a is pressed, display unit 131 displays screen P148.

Screen P148 shows a description to start stirring the sample, Continue button P148a, and Quit button P148b. When Continue button P148a is pressed, display unit 131 displays screen P149 (see FIG. 38).

Figure 38:
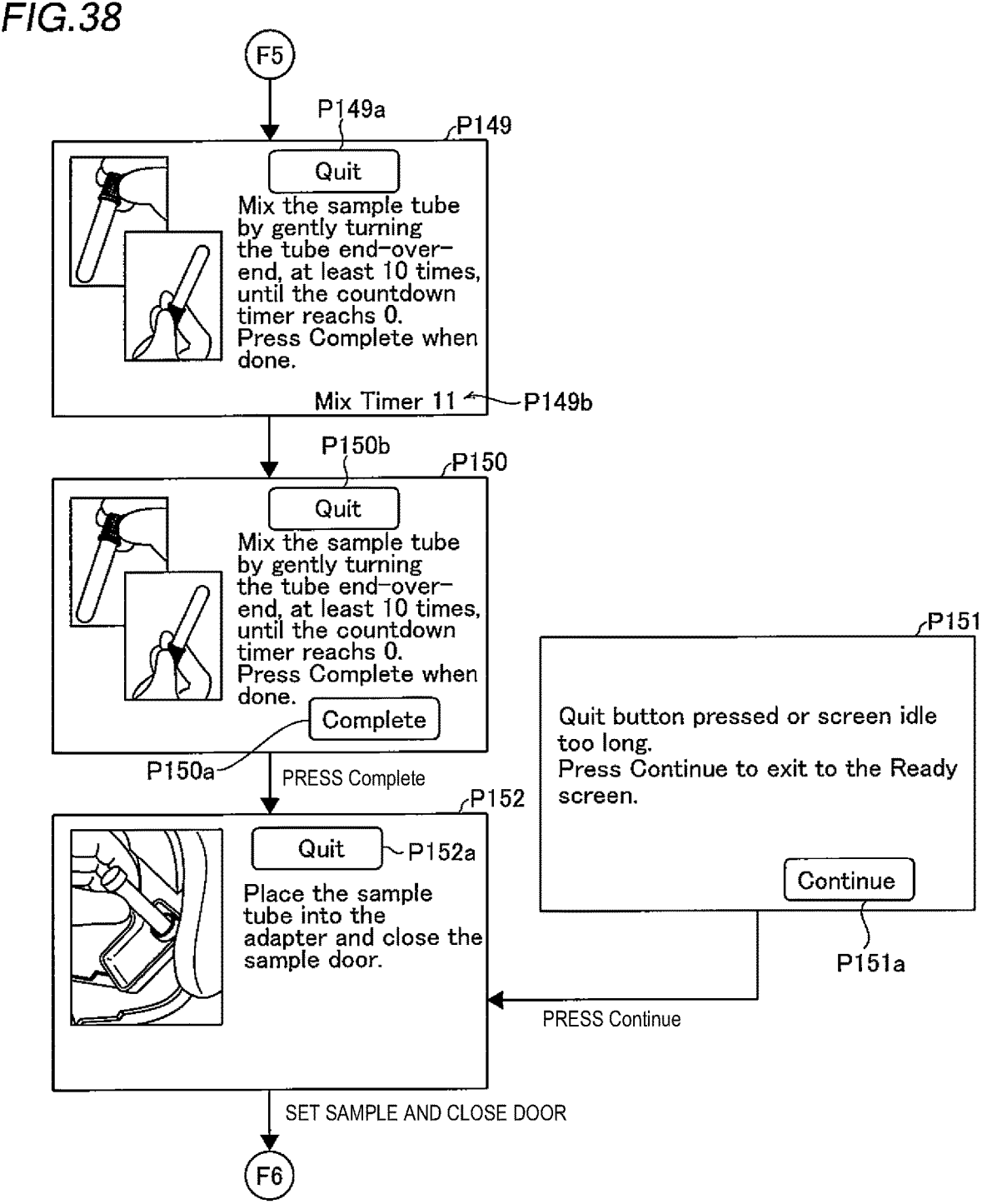
FIG. 38 is a diagram illustrating display example 6 for sample measurement.

As illustrated in FIG. 38, screen P149 shows a description to stir the sample, Quit button P149a, and timer P149b. Timer P149b is displayed counting down from 15 sec, for example. When the time counted down by timer P149b has elapsed, display unit 131 displays screen P150. Screen P150 shows Complete button P150a and Quit button P150b. When Complete button P150a is pressed, display unit 131 displays screen P152.

Here, display unit 131 displays screen P151 when the Quit button is pressed in any of the screens, or when a predetermined time period has elapsed with the screen left unoperated. Screen P151 shows Continue button P151a. When Continue button P151a is pressed, display unit 131 shows screen P152.

Screen P152 shows a picture and an instruction on how to set the sample container. Also, screen P152 shows Quit button P152a.

Figure 39:
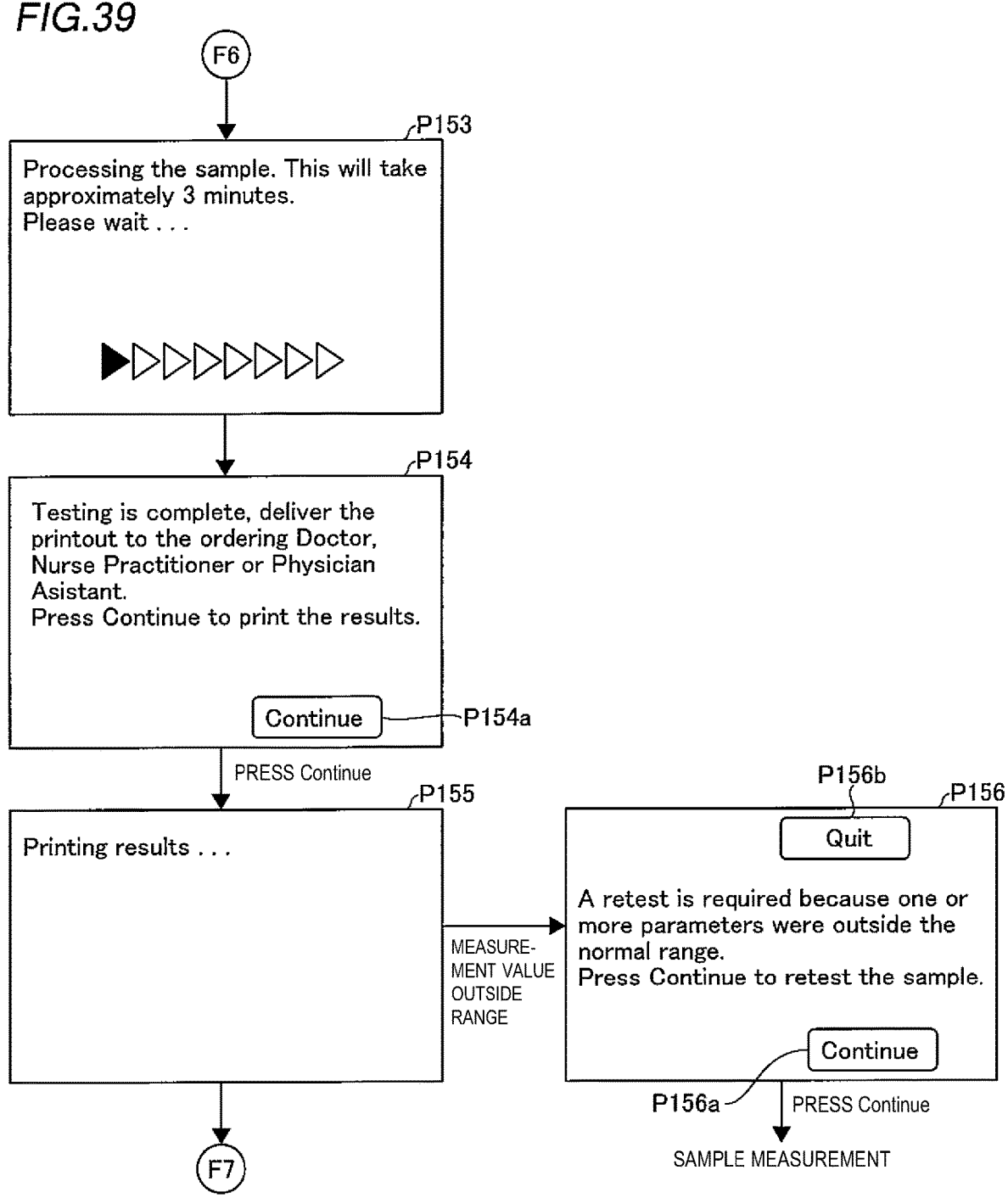
FIG. 39 is a diagram illustrating display example 7 for sample measurement.

When the sample container is set and the door is closed, display unit 131 displays screen P153, as illustrated in FIG. 39. Also, measurement of sample is performed. When the measurement of the sample finishes, display unit 131 displays screen P154. Screen P154 shows a description for printing and Continue button P154a. When Continue button P154a is pressed, display unit 131 displays screen P155.

Screen P155 shows a description that the printing is in progress. Also, print unit 135 prints the results. If one or more of the measurement results are outside normal range, display unit 131 displays screen P156. Screen P156 shows a description to perform measurement again, Continue button P156a, and Quit button P156b. When Continue button P156a is pressed, display unit 131 displays first screen P131 of sample measurement (see FIG. 33).

Figure 40:
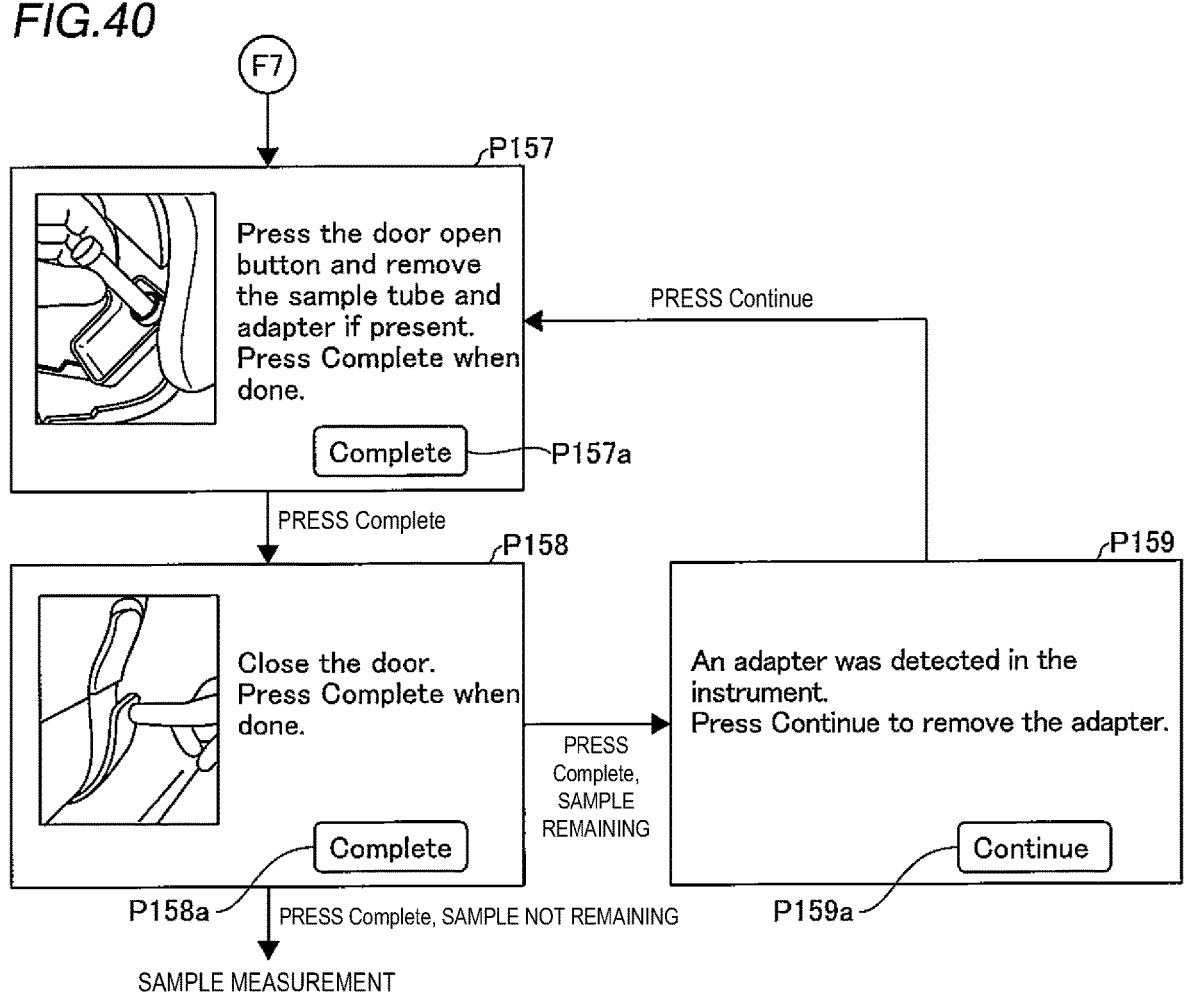
FIG. 40 is a diagram illustrating display example 8 for sample measurement.

As illustrated in FIG. 40, screen P157 shows a picture and an instruction on how to remove the sample container from specimen analyzer 100. Also, screen P157 shows Complete button P157a. When Complete button P157a is pressed, display unit 131 displays screen P158. Screen P158 shows a picture and an instruction on how to close the door. Also, screen P158 shows Complete button P158a. When Complete button P158a is pressed, the sample measurement process finishes. Thereafter, display unit 131 displays first screen P131 of sample measurement (see FIG. 33).

If the adapter is remaining when Complete button P158a is pressed, display unit 131 displays screen P159. Screen P159 shows Continue button P159a. When Continue button P159a is pressed, display unit 131 displays screen P157.

Thus, in the example of FIG. 40, display unit 131 displays print operation screen (see screen P154) for starting of the printing of analysis results 102.

In print operation screen P154, display unit 131 displays operational guidance and instructions to deal with printed sheet after printing.

The instructions to deal with the printed sheet include a message instructing to deliver the printed sheet to the ordering doctor.

Print unit 135 starts the printing of analysis results 102 based on the operations in accordance with print operation screen P154 (see screen P155). To be more specific, print unit 135 starts the printing of analysis results 102 based on the input of Continue button P154a.

Also, in the example of FIG. 39 and the example of FIG. 40, analysis unit 120 is capable of analyzing next specimen 101 if an operation is performed in accordance with the print operation screen. To be more specific, if a series of operations up to screen P158 including an operation on screen P154 completes, controller 140 causes display unit 131 to display P131 (see FIG. 33) to be ready for an analysis of next specimen 101.

In addition, if analysis results 102 include an abnormal value, controller 140 causes display unit 131 to display an abnormal value notification screen (see screen P156) to communicate that an abnormal value is included. When abnormal value notification screen P156 is displayed, analysis unit 120 is capable of retesting same specimen 101 when an operation is performed in accordance with abnormal value notification screen P156.

If analysis results 102 include an abnormal value, controller 140 prohibits print unit 135 from printing analysis results 102, and causes abnormal value notification screen P156 to show a message prompting to perform retesting. The example of screen P156 shows a message communicating it is necessary to retest because one or more analysis results 102 are outside normal range.

In the example of screen P156, when Continue button 156a is inputted, a series of processes for performing retest are executed. Here, by inputting Quit button 156b, analysis of another specimen 101 can be started.

(Display Example at Maintenance)

With reference to FIG. 41 to FIG. 48, a display example at maintenance is described.

Figure 41:
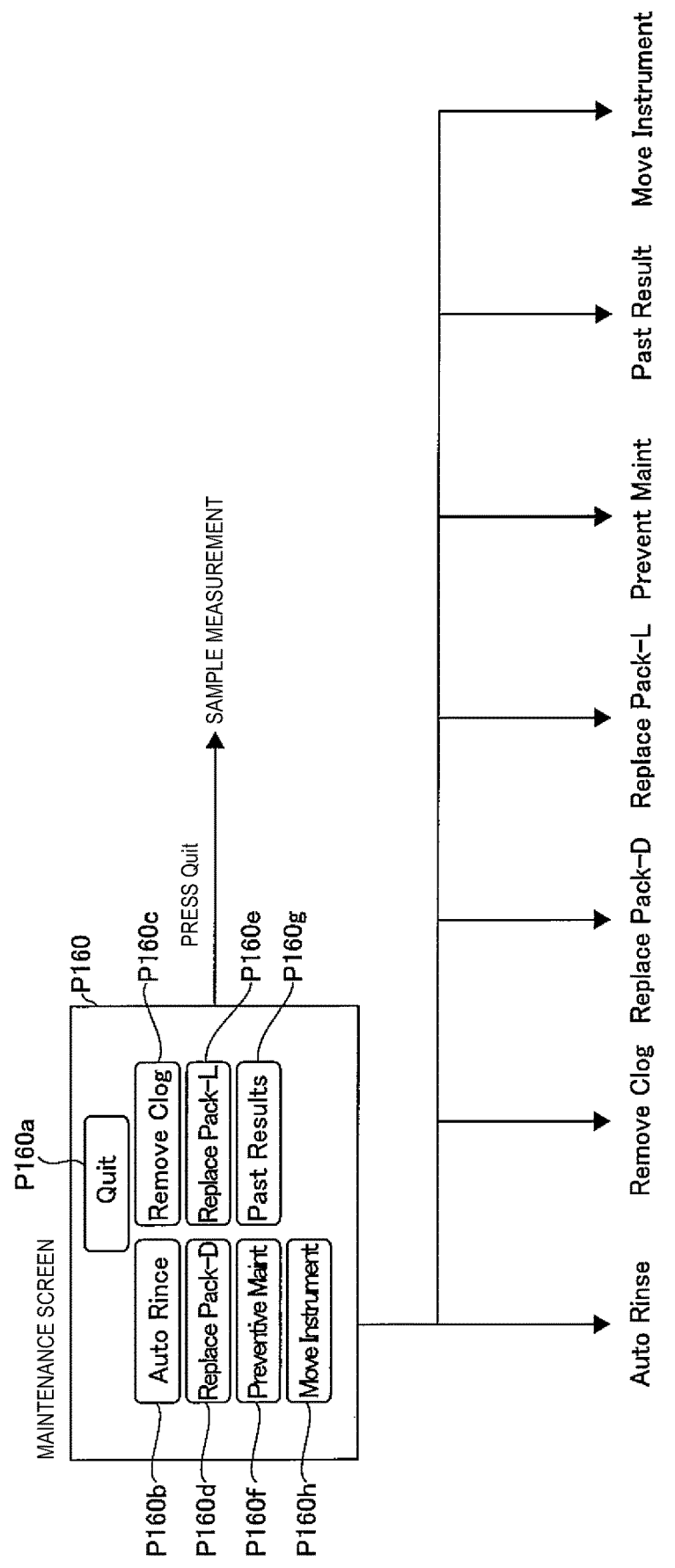
FIG. 41 is a diagram illustrating display example 1 for maintenance.

As illustrated in FIG. 41, screen P160 shows a screen for performing maintenance. To be more specific, screen P160 Quit button P160a, Auto Rince button P160b, Remove Clog button P160c, Replace Pack-D button P160d, Replace Pack-L button P160e, Preventive MaintP button P160f, Past Results button P160g, and Move Instrument button P160h.

Figure 42:
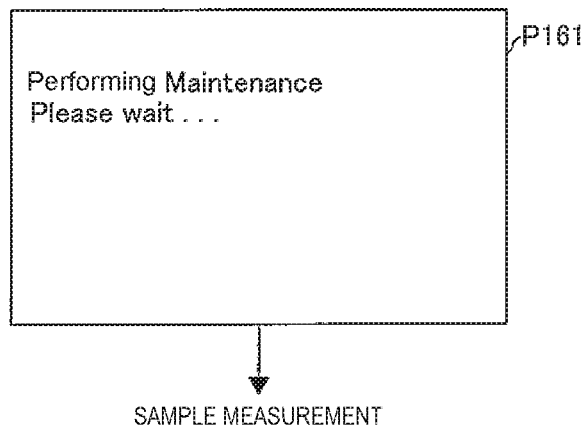
FIG. 42 is a diagram illustrating display example 2 for maintenance.

When Auto Rince button P160b is pressed, display unit 131 displays screen P161, as illustrated in FIG. 42. Also, a cleaning process with use of a diluted solution is performed. Thereafter, display unit 131 displays first screen P131 of sample measurement (see FIG. 33).

Figure 43:
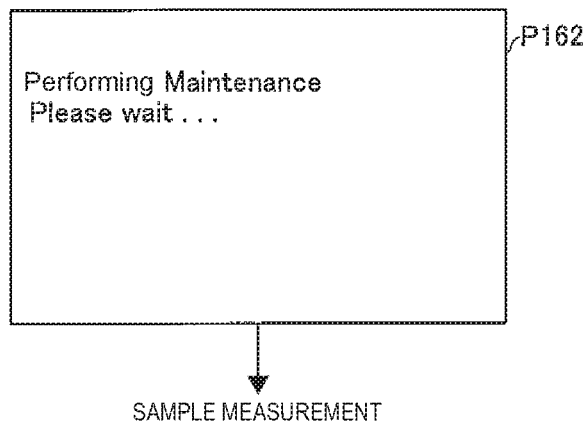
FIG. 43 is a diagram illustrating display example 3 for maintenance.

When Remove Clog button P160c is pressed, display unit 131 displays screen P162, as illustrated in FIG. 43. Also, a process of removing the clog of detector 123 is performed.

Figure 44:
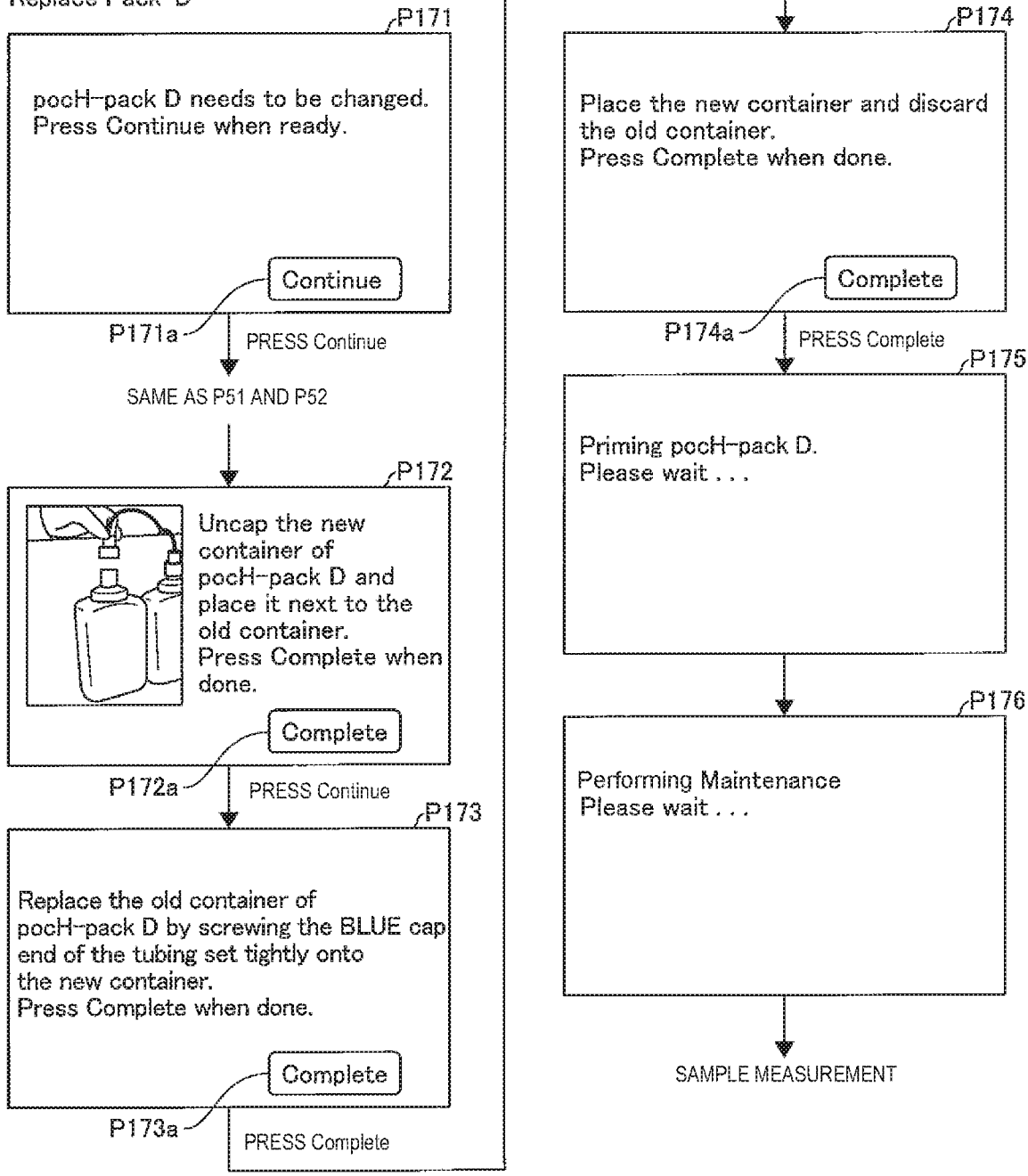
FIG. 44 is a diagram illustrating display example 4 for maintenance.

When Replace Pack-D button P160d is pressed, display unit 131 displays screen P171, as illustrated in FIG. 44. In addition, display unit 131 displays screen P171 also in the case where it is determined that the diluted solution has been used up. Screen P171 displays Continue button P171a. When Continue button P171a is pressed, display unit 131 displays screens similar to screens P51 and P52, and similar processes are performed. Thereafter, display unit 131 displays screen P172.

Screen P172 shows a picture and an instruction on how to place the reagent container. Also, screen P172 shows Complete button P172a. When Complete button P172a is pressed, display unit 131 displays screen P173. Screen P173 shows a description for replacing the reagent container. Also, screen P173 shows Complete button P173a. When Complete button P173a is pressed, display unit 131 displays screen P174.

Screen P174 shows a description to place and dispose of the reagent container. Also, screen P174 shows Complete button P174a. When Complete button P174a is pressed, display unit 131 displays screen P175. Also, the diluted solution is fed to specimen analyzer 100. Thereafter, display unit 131 displays screen P176. After that, display unit 131 displays first screen P131 of sample measurement (see FIG. 33).

When Replace Pack-L button P160e is pressed, display unit 131 displays screen P181, as illustrated in FIG. 45. In addition, display unit 131 displays screen P181 also in the case where it is determined that the hemolyzer has been used up. Screen P181 displays Continue button P181a. When Continue button P181a is pressed, display unit 131 displays screens similar to screens P51, P52, and P172 to P176, and similar processes are performed. Thereafter, display unit 131 displays first screen P131 of sample measurement (see FIG. 33).

When Preventive MaintP button P160f is pressed, display unit 131 displays screen P191, as illustrated in FIG. 46. Also, display unit 131 displays screen P191 when cleaning by CELLCLEAN is needed. Screen P191 shows Continue button P191a. When Continue button P191a is pressed, a process similar to the cleaning by CELLCLEAN is performed. Thereafter, a process similar to the QC measurement is performed, and display unit 131 displays first screen P131 of sample measurement (see FIG. 33).

Figure 47:
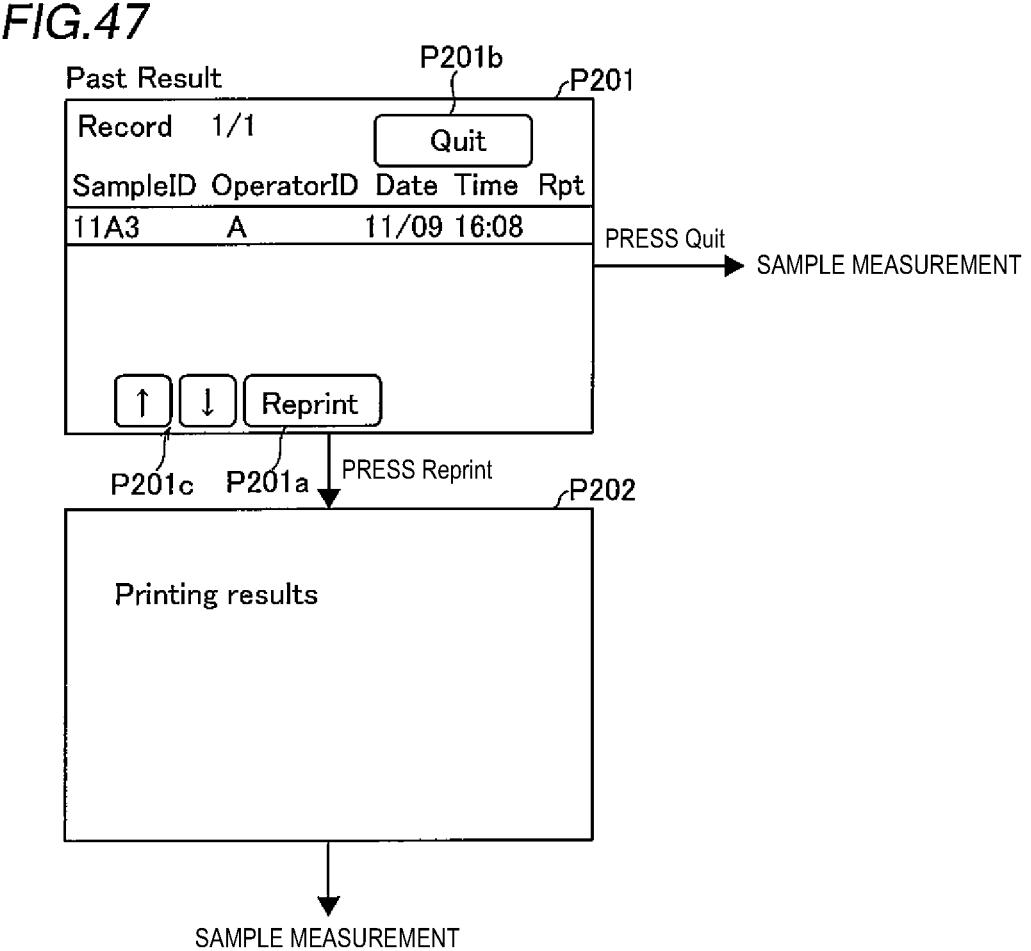
FIG. 47 is a diagram illustrating display example 7 for maintenance.

When Past Results button P160g is pressed, display unit 131 displays screen P201, as illustrated in FIG. 47. Screen P201 shows Reprint button P201a, Quit button P201b, and select button P201c. When select button P201c is used to select a past measurement and Reprint button P201a is pressed, past measurement results are printed. By pressing Reprint button 201a, display unit 131 displays screen P202. Then, print unit 135 prints the measurement results. Thereafter, display unit 131 displays first screen P131 of sample measurement (see FIG. 33).

Figure 48:
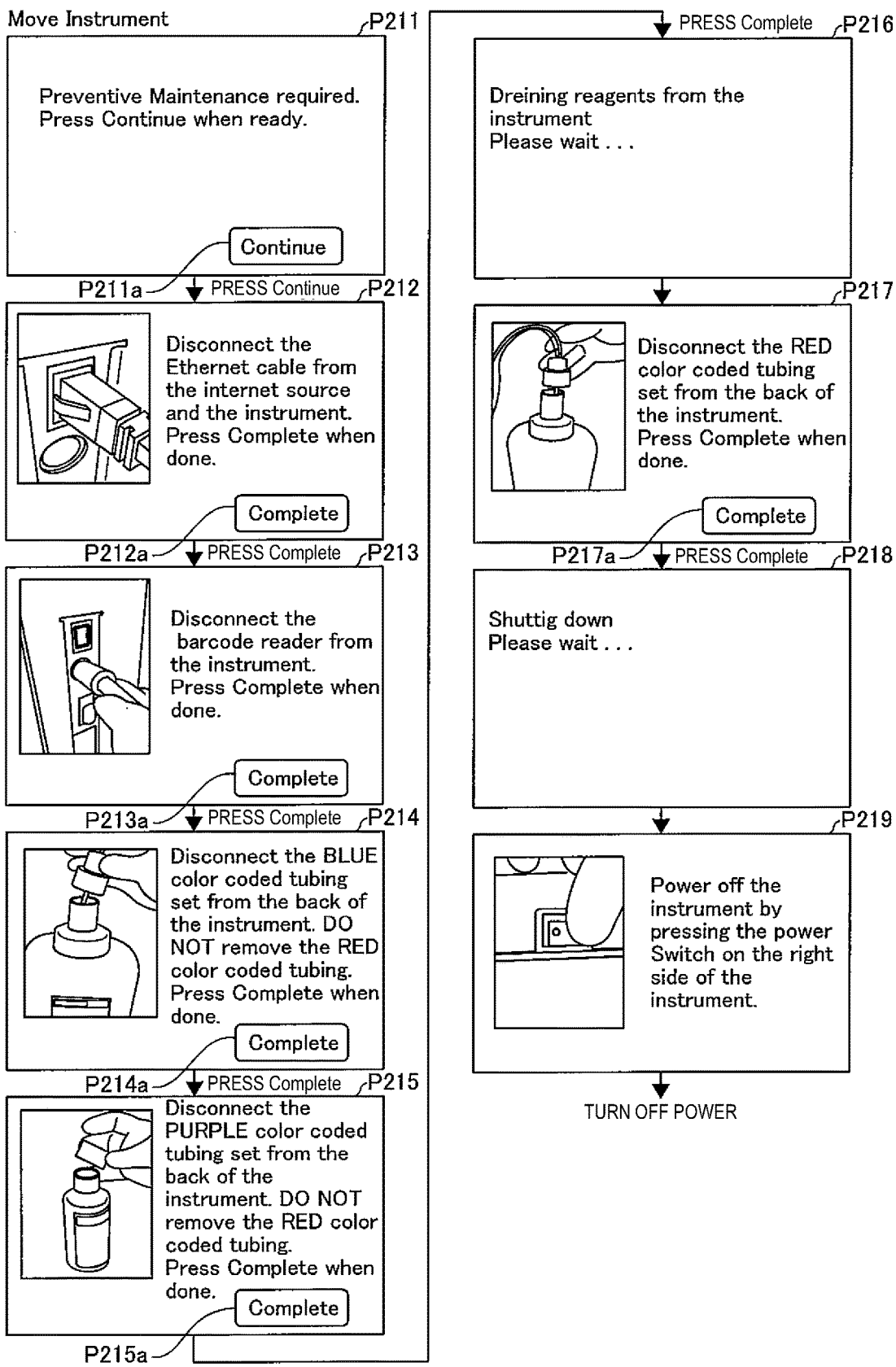
FIG. 48 is a diagram illustrating display example 8 for maintenance.

When Move Instrument button P160h is pressed, display unit 131 displays screen P211, as illustrated in FIG. 48. Screen P211 shows Continue button P211a. When Continue button P211a is pressed, display unit 131 displays screen P212. Screen P212 shows a picture and an instruction on how to remove the Ethernet cable from specimen analyzer 100. Also, screen P212 shows Complete button P212a. When Complete button P212a is pressed, display unit 131 displays screen P213.

Screen P213 shows a picture and an instruction on how to remove the barcode reader from specimen analyzer 100. Also, screen P213 shows Complete button P213a. When Complete button P213a is pressed, display unit 131 displays screen P214. Screen P214 shows a picture and an instruction on how to remove the container of the diluted solution from the tube. Also, screen P214 shows Complete button P214a. When Complete button P214a is pressed, display unit 131 displays screen P215.

Screen P215 shows a picture and an instruction on how to remove the container of the hemolyzer from the tube. Also, screen P215 shows Complete button P215a. When Complete button P215a is pressed, display unit 131 displays screen P216. Screen P216 shows a description to discharge the liquid. In addition, the liquid is discharged from specimen analyzer 100. Thereafter, display unit 131 displays screen P217.

Screen P217 shows a picture and an instruction on how to remove the container of the waste liquid from the tube. Also, screen P217 shows Complete button P217a. When Complete button P217a is pressed, display unit 131 displays screen P218. Screen P218 shows a description that shutdown is in progress. Thereafter, display unit 131 displays screen P219.

Screen P219 shows a picture and an instruction on how to power off specimen analyzer 100. Thereafter, the user powers off.

(Outputting of Analysis Results)

In the example illustrated in FIG. 2, analysis unit 120 perform analysis on seventeen analysis items in total, eight measurement items plus nine analysis items, as described above. In the embodiment, controller 140 performs control of causing print unit 135 to print analysis results 102, and prohibiting display unit 131 from displaying analysis results 102. Thus, as a result of analysis operations of specimen analyzer 100, the user obtains printed sheet 300 being print sheet 136 on which analysis results 102 are written, as illustrated in FIG. 49.

In the example of FIG. 49, printed on printed sheet 300 are facility information 301, apparatus information 302, date information 303, operator information 304, subject information 305, subject attribute information 306, result displaying section 307, message section 308, and reference value information 309. Note that although printed sheet 300 is separated for convenience in FIG. 49, the separated portions are actually connected, and printed sheet 300 is one piece of print sheet 136 on which printing has been performed.

Facility information 301 includes information on the name and the address of the facility such as a hospital where specimen analyzer 100 is installed.

Apparatus information 302 is information for identifying specimen analyzer 100 which performed analysis. Apparatus information 302 includes, for example, the model, the name, and the serial number of the apparatus.

Date information 303 is information for identifying the time point at which analysis was performed. Date information 303 includes the analysis date. In FIG. 49, date information 303 includes the analysis time in addition to the analysis date.

Operator information 304 is ID information for identifying the operator who operated specimen analyzer 100. Operator information 304 is not particularly limited, and is represented by three alphabetical letters, for example.

Subject information 305 is ID information for identifying the subject from which specimen 101 is collected. Subject information 305 is represented by a seven-digit number, for example.

Subject attribute information 306 is information on the subject from which specimen 101 is collected, and shows the characteristics and nature of the subject. Preferable as subject attribute information 306 is information useful for diagnosis based on analysis results 102. Subject attribute information 306 includes at least one of the date of birth, age, and sex, for example. It is possible to grasp the age of the subject using the date of birth. Subject attribute information 306 may be an age, or information on the corresponding one of the age sections. There is a case where the criteria for diagnosis based on analysis results 102 differ depending on the sex, in addition to the age. Hence, subject attribute information 306 may include sex. Furthermore, subject attribute information 306 may include body information such as the height and the weight of the subject.

Result displaying section 307 is an area where analysis results 102 are printed. Analysis results 102 include numerical information 102a. In addition, if analysis results 102 include an error, analysis results 102 include information 102b indicating the type of the abnormality. As illustrated in FIG. 49, regarding multiple analysis items, print unit 135 prints analysis results 102 for each of the analysis items. Regarding each analysis item, one line of result displaying section 307 is assigned one item. To be more specific, in each analysis item of result displaying section 307, the item name, numerical information 102a, and information 102b indicating the type of the abnormality (flag) are displayed in sequential order from left.

Information 102b indicating the type of the abnormality is printed to notify the user of the type of the abnormality when one or more of analysis results 102 are outside normal range, or when there is a predetermined analysis result error. If analysis results 102 include an abnormal value, controller 140 prints information 102b indicating the type of the abnormality as analysis results 102. Determination as to whether or not the results are normal or erroneous is made based on the numerical ranges for analysis result determination.

In the example of FIG. 50, for example, as information 102b indicating the type of the abnormality, print unit 135 prints information 102b indicating the type of the abnormality if analysis results 102 includes an abnormal value. Information 102b indicating the content of the error includes information 314 indicating a first error showing that numerical information 102a is included in a first erroneous ranges 372 (see FIG. 53), and information 315 indicating a second error showing that numerical information 102a is included in a second erroneous ranges 373 (see FIG. 53). Information 314 indicating a first error can include an indicator indicating a high value (High) and an indicator indicating a low value (Low) for each of analysis results 102. Information 315 indicating a second error can include an indicator indicating an erroneously high value (ALERT H) and an indicator indicating an erroneously low value (ALERT L), for example.

If a certain abnormal value included in analysis results 102 is included in a preset predetermined numerical range, controller 140 excludes the predetermined abnormal value in analysis result 102 from the content to be printed. An embodiment of displaying result displaying section 307 is described later.

In FIG. 49, displayed in message section 308 is a predetermined message to the user in a predetermined case. The predetermined message includes message 311 prompting further testing. Furthermore, the predetermined message includes, for example, message 312 recommending the user to act immediately. If analysis results 102 have no particular problem, no message is displayed in message section 308.

The intention of reference value information 309 is to provide information for evaluating analysis results 102 to the user. Thus, in addition to analysis results 102, print unit 135 prints reference value information 309 to evaluate analysis results 102. Analysis result 102 of each analysis item has a numerical range considered a normal range. Reference value information 309 of FIG. 49 is information on numerical ranges indicating normal ranges 371 of analysis results 102. Here, the normal range for each analysis item differs depending on subject attribute information 306 such as the age of the subject. In light of this, in FIG. 49, reference value information 309 possesses several types depending on subject attribute information 306 on the subject from which specimen 101 is collected. Print unit 135 prints: subject attribute information 306: and reference value information 309 corresponding to subject attribute information 306 out of several types of reference value information 309.

As described above, in the example of FIG. 49, in addition to analysis results 102, print unit 135 prints the analysis date, operator information 304 on the operator who performed analysis, and subject attribute information 306 on the subject from which the specimen is collected.

The information above is printed on the same surface of a single piece of print sheet 136. To be more specific, print unit 135 prints analysis results 102, subject attribute information 306, reference value information 309, and the predetermined message, if necessary, on the same surface of a single piece of print sheet 136. In the example of FIG. 49, all information to be printed is printed on the same surface of a single piece of print sheet 136.

(Output Rules and Display Embodiment of Analysis Results on Printed Sheet)

Subsequently, output rules and a display embodiment in result displaying section 307 of printed sheet 300 are described.

Controller 140 determines whether or not analysis results 102 can be outputted depending on numerical information 102a as analysis results 102. If numerical information 102a falls within a predetermined range, controller 140 prohibits outputting of numerical information 102a to printed sheet 300. Memory 142 of controller 140 stores data of numerical ranges for analysis result determination (see FIG. 53 to FIG. 55).

<First Determination Ranges>

As illustrated in FIG. 51, out of numerical information 102a as analysis results 102 of analysis unit 120, controller 140 performs control of prohibiting the outputting of numerical information 102a outside first determination ranges relating to reliability of analysis.

FIG. 52 illustrates an example of first determination ranges 350. First determination ranges 350 (see FIG. 52) are each a numerical range considered reliable enough for analysis itself by analysis unit 120. First determination ranges 350 are each a numerical range which surely has reproducibility, accuracy, linearity, etc. of analysis results 102 of specimen analyzer 100 within a predetermined range, and is a numerical range set as the specifications of specimen analyzer 100.

In the example of FIG. 52, first determination ranges 350 are each a linearity guarantee range for specimen analyzer 100. To be more specific, analysis unit 120 outputs analysis results proportional to the number and the concentration of the target components in specimen 101. Here, the linearity guarantee range is a range where the analysis results match the line of proportionality within a predetermined error range. In other words, the linearity guarantee range may be referred to as a measurable range for analysis unit 120. Out of the analysis items, first determination ranges 350 are set for five measurement items, WBC, RBC, HGB, HCT, and PLT, which are measured by detector 123. Regarding the measurement items, when numerical information 102a outside the numerical ranges illustrated in FIG. 52 is obtained as analysis results 102, controller 140 prohibits the outputting of numerical information 102a as a measurement error.

In the example of FIG. 51, even in the case of numerical information 102a within first determination ranges 350, controller 140 performs control of prohibiting outputting when numerical information 102a includes a predetermined abnormal value. Regarding numerical information 102a within first determination ranges 350, controller 140 prohibits outputting when the information is within second determination ranges 360 indicating a predetermined error of the specimen, and performs control of permitting outputting when the information is outside second determination ranges 360.

Figure 53:
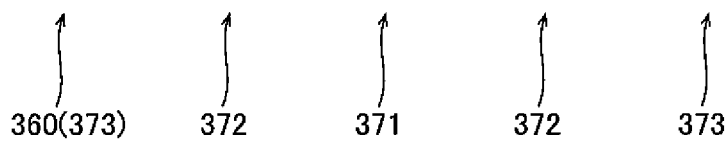
FIG. 53 is a diagram for explaining numerical ranges for evaluating analysis results for an infant.
Figure 54:
FIG. 54 is a diagram for explaining numerical ranges for evaluating analysis results for a youth.

First, regarding numerical information 102a within first determination ranges 350, analysis unit 120 performs analysis based on the numerical ranges for analysis result determination illustrated in FIG. 53 to FIG. 55. To be more specific, first determination ranges 350 include normal ranges (reference ranges) 371 indicating normal values, first erroneous ranges 372 wider than corresponding normal ranges 371, and second erroneous ranges 373 wider than first erroneous ranges 372. In the embodiment, second determination ranges 360 are set as second erroneous ranges 373.

<Normal Range>

Controller 140 outputs analysis results 102 included in normal ranges 371 illustrated in FIG. 53 to FIG. 55. In the example of printed sheet 300 illustrated in FIG. 50, for instance, the value of MCH (29.8 [pg]) falls within the normal range of an adult (see FIG. 55), and numerical information 102a is printed as it is. If analysis results 102 are included in normal ranges 371, this means there is no error. Thus, information 102b indicating the type of the abnormality for the analysis items is not printed.

As illustrated in FIG. 53 to FIG. 55, first erroneous ranges 372 include ranges of low value (Low) and ranges of high value (High). Second erroneous ranges 373 include ranges of erroneously low value (ALERT LOW) and ranges of erroneously high value (ALERT HIGH). To be more specific, first erroneous ranges 372 are ranges indicating minor errors near normal ranges 371, and second erroneous ranges 373 are ranges indicating significant errors further deviating from first erroneous ranges 372.

<First Erroneous Range>

In the example of FIG. 51, in the initial test, controller 140 prohibits the outputting of printed sheet 300 if numerical information 102a is included in first erroneous ranges 372. To be more specific, if numerical information 102a is included in first erroneous ranges 372, controller 140 does not output printed sheet 300 but causes the user to perform retest on same specimen 101 using abnormal value notification screen P156 for notifying that an abnormal value is included. Thus, in the initial test, all analysis results 102 are prohibited from being outputted if numerical information 102a is included in first erroneous ranges 372.

Controller 140 causes printed sheet 300 to output analysis results 102 obtained in retest. If initial analysis results 102 match retested analysis results 102, controller 140 causes print unit 135 to print analysis results 102, and if initial analysis results 102 do not match retested analysis results 102, controller 140 prohibits the printing of mismatched analysis results 102. To be more specific, if numerical information 102a of retest is included in first erroneous ranges 372 and if determination results of numerical information 102a match those of the initial test, controller 140 permits the outputting of that numerical information 102a, and outputs information indicating the type of the abnormality. For example, if numerical information 102a of the initial test is included in the range of "Low" and if numerical information 102a of retest is included in the range of "Low" as well, the controller outputs information 314 indicating a first error where numerical information 102a is included in first erroneous ranges 372, together with numerical information 102a.

In the example of printed sheet 300 illustrated in FIG. 50, the value of MCV (81.6 [fL]) corresponds to a low value (see FIG. 55) of an adult, and "Low" information 314 indicating a first error is printed together with analysis results. Note that if the analysis result corresponds to a high value, "High" is printed as information 314 indicating a first error.

If numerical information 102a of retest is included in first erroneous ranges 372 and if determination results of numerical information 102a do not match those of the initial test, controller 140 prohibits the outputting of that numerical information 102a, and outputs information indicating the type of the abnormality. For example, if numerical information 102a of the initial test is included in the range of "Low" and if numerical information 102a of retest is included in the range of "High," the controller prohibits the outputting of numerical information 102a. In this case, as the analysis items, information 314 indicating a first error is printed.

<Second Erroneous Range>

In the example of FIG. 51, out of numerical information 102a included in second erroneous ranges 373, controller 140 prohibits the outputting of numerical information 102a within second determination ranges 360, and permits the outputting of numerical information 102a outside second determination ranges 360. If numerical information 102a is included in second erroneous ranges 373, controller 140 outputs information 102b indicating the type of the abnormality. To be more specific, as has been illustrated in FIG. 50, controller 140 displays an indicator indicating an erroneously high value (ALERT H) or an indicator indicating an erroneously low value (ALERT L) as information 315 indicating a second error where numerical information 102a is included in second erroneous ranges 373.

Second determination ranges 360 are each a range of abnormal value presenting the possibility of having a predetermined serious disease. Possible predetermined serious diseases in the blood cell counting apparatus include, for example, leukemia, aplastic anemia, myelodysplastic syndromes, paroxysmal nocturnal hemoglobinuria, systemic lupus erythematosus, malignant lymphoma, disseminated intravascular coagulation, thrombotic thrombocytopenic purpura, hypersplenism, megaloblastic anemia, sepsis, tuberculosis, sarcoidosis, hemangioma, infectious diseases, and congenital thrombocytopenia.

Each of second determination ranges 360 is set as at least part of corresponding one of second erroneous ranges 373. Each of second determination ranges 360 is set within a range satisfying corresponding one of first determination ranges 350 and within a range of predetermined erroneously low value.

In the example of FIG. 53 to FIG. 55, each of second determination ranges 360 is set within a range of erroneously low value (ALERT LOW) of corresponding one of second erroneous ranges 373 set for at least one analysis item of white blood cell count (WBC), hemoglobin concentration (HGB), hematocrit value (HCT), and platelet count (PLT). In FIG. 53 to FIG. 55, the range of erroneously low value (ALERT L) of each of white blood cell count, hemoglobin concentration, hematocrit value, and platelet count is set as corresponding one of second determination ranges 360.

Thus, if numerical information 102a is included in a range of erroneously low value (ALERT L), controller 140 prohibits the outputting of numerical information 102a. If there is numerical information 102a within second determination ranges 360, controller 140 causes output unit 130 to output information 102b indicating the type of the abnormality. To be more specific, if numerical information 102a is included in a range of erroneously low value (ALERT L), controller 140 prints information 315 indicating a second error (ALERT L) being an erroneously low value.

If numerical information 102a is included in a range of erroneously high value (ALERT H), controller 140 permits the outputting of numerical information 102a. If numerical information 102a is included in a range of erroneously high value (ALERT H), controller 140 prints information 315 indicating a second error being an erroneously high value (ALERT H).

For example, in the example of printed sheet 300 illustrated in FIG. 50, the value of HGB (24.3 [g/dL]) corresponds to an erroneously high value of an adult, and "ALERT H" information 315 indicating a second error is printed together with numerical information 102a.

On the other hand, in the example of printed sheet 300 illustrated in FIG. 50, numerical information 102a is not printed for WBC and PLT. This is because numerical information 102a of WBC and PLT falls within second determination ranges 360 (see FIG. 55). In the example of FIG. 50, "ALERT L" information 315 indicating a second error is printed for the analysis items of WBC and PLT. Thus, it is possible to know which analysis items fall within second determination ranges 360 even though numerical information 102a is not outputted.

When excluding a predetermined abnormal value from the content to be printed, controller 140 causes substitute indication 313 to be printed in place of the predetermined abnormal value. For example, controller 140 substitutes numerical information 102a within second determination ranges 360 for substitute indication 313, and causes output unit 130 to print substitute indication 313. In the example of FIG. 50, numerical information WBC and PLT within second determination ranges 360 is printed in the form of substitute indication 313 "****." Note that any display embodiment of substitute indication 313 is possible as long as it can be distinguished from numerical information 102a. Thus, substitute indication 313 is preferably a character other than a number, a symbol, or a plane figure, for example. If numerical information 102a is within second determination ranges 360, controller 140 prints information 102b indicating the type of the abnormality together with substitute indication 313.

As described above, if numerical information 102a is included in first erroneous ranges 372 or second erroneous ranges 373, controller 140 outputs information 102b indicating the type of the abnormality as analysis results 102. Controller 140 prohibits the outputting of numerical information 102a within second determination ranges 360, and permits the outputting of information 102b indicating the type of the abnormality.

On the other hand, if numerical information 102a is outside first determination ranges 350, controller 140 substitutes numerical information 102a outside first determination ranges 350 for substitute indication 313 and causes output unit 130 to output substitute indication 313, and prohibits the outputting of information 102b indicating the type of the abnormality. To be more specific, if numerical information 102a falls within none of normal ranges 371, first erroneous ranges 372, and second erroneous ranges 373 described above, and is outside the linearity guarantee ranges, the numerical information is substituted for substitute indication 313 on printed sheet 300. Information 102b indicating the type of the abnormality such as information 314 or 315 is not printed.

In the example of FIG. 50, for the analysis items outside first determination ranges 350 and for the analysis items within second determination ranges 360, controller 140 prints the item names and prohibits the outputting of numerical information 102a. When excluding a predetermined abnormal value from the content to be printed, print unit 135 prints substitute indication 313 in place of the predetermined abnormal value.

Note that in the example of FIG. 51, the case where the outputting of numerical information 102a is prohibited for the analysis items other than the measurement items includes the case of a fractionation error of the analysis results. In the case of a fractionation error, controller 140 prohibits the outputting of numerical information 102a, and outputs information 102b indicating the type of the abnormality corresponding to the type of the fractionation error. Information 102b indicating the type of the abnormality corresponding to the type of the fractionation error includes "WBC," "RBC," "PLT," "WBC/PLT," and "WBC Diff". FIG. 50 illustrates an example where WBC Diff is displayed, and "WBC," "RBC," "PLT," and "WBC/PLT" are also displayed in the same manner.

"WBC" is printed if the number of particles of upper discriminator value or lower discriminator value is erroneously high in the particle size distribution of white blood cells. The discriminator value is a value for distinguishing the distribution of white blood cells from noise components called ghost. "RBC" is printed if the number of particles of upper discriminator value or lower discriminator value is erroneously high in the particle size distribution of red blood cells, if it is impossible to analyze red blood cell distribution width (RDW-SD and RDW-CV), or if the particle size distribution of red blood cells is bimodal. "PLT" is printed if the number of particles of upper discriminator value or lower discriminator value is erroneously high in the particle size distribution of platelets, or if it is impossible to analyze red blood cell distribution width (RDW-SD and RDW-CV). "WBC/PLT" is printed if the number of particles having a predetermined value or less is erroneously high in the particle size distribution of white blood cells. In the particle size distribution of white blood cells, "WBC Diff" is printed in any of the cases where it is impossible to fractionate into small-sized white blood cells and medium-sized white blood cells, where the discriminator value for fractionating into small-sized white blood cells and medium-sized white blood cells is high, where it is impossible to fractionate into medium-sized white blood cells and large-sized white blood cells, or where the discriminator value for fractionating into medium-sized white blood cells and large-sized white blood cells. In the cases of these fractionation errors, controller 140 substitutes numerical information 102a for a substitute indication.

As illustrated in FIG. 50, for each of the analysis items, controller 140 prohibits the outputting of numerical information 102a outside first determination ranges 350 and the outputting of numerical information 102a within second determination ranges 360. For this reason, in the case where numerical information 102a outside the linearity guarantee range is obtained or "ALERT L" numerical information 102a is obtained for any of the analysis items, other analysis items for which printable numerical information 102a is obtained are printed.

(Age Section)

FIG. 53 to FIG. 55 illustrate data examples of numerical ranges for analysis result determination, for each of the age sections. As examples of age sections, FIG. 53 illustrates an infant at the ages of two to eleven, FIG. 54 illustrates a youth at the ages of twelve to twenty, and FIG. 55 illustrates an adult at the ages of twenty one or more. The number of sections may be other than three.

In the examples of FIG. 53 to FIG. 55, out of normal ranges 371, first erroneous ranges 372, and second erroneous ranges 373, at least normal ranges 371 differ depending on the age sections. Controller 140 calculates the age of the subject from subject attribute information 306, and obtains the numerical ranges of the age section corresponding to the calculated age. Then, when numerical information 102a is obtained for each of the analysis items, analysis unit 120 analyzes which of normal ranges 371, first erroneous ranges 372, and second erroneous ranges 373, and second determination ranges 360 numerical information 102a falls within, based on the numerical ranges of the age section to which the subject belongs.

In addition, controller 140 prints normal ranges 371 of the age section to which the subject belongs on printed sheet 300 as reference value information 309. In the example of FIG. 49, it is possible to know from subject attribute information 306 (born in 1965) that the subject is an adult at the age of twenty one or more as of date information 303. Thus, FIG. 55 illustrates normal ranges 371 of the age section of an adult printed as reference value information 309. Reference value information 309 is printed for each of the analysis items. Here, in FIG. 53 to FIG. 55, the numerical ranges of "ALERT L" second determination ranges 360 are the same regardless of the age section. However, second determination ranges 360 may be different for each age section.

(Predetermined Message)

Subsequently, the predetermined message printed on printed sheet 300 is described. In the example of FIG. 49, if there is numerical information 102a within second determination ranges 360, controller 140 causes output unit 130 to output the predetermined message.

If numerical information 102a is within second erroneous ranges 373, controller 140 prints message 311 prompting further testing. To be more specific, if there is numerical information 102a corresponding to an erroneously high value (ALERT H) or an erroneously low value (ALERT L) within second determination ranges 360 for any of the analysis items, message 311 prompting further testing is printed. In FIG. 49, as an example, the message "RECOMMEND FURTHER TESTING" is printed.

Also, if numerical information 102a is within second erroneous ranges 373, controller 140 further prints message 312 recommending immediate action. In FIG. 49, as an example, message 312 "Potential ALERT Value should be acted upon IMMEDIATELY" is printed.

Also, numerical information 102a of all analysis items is within normal ranges 371, controller 140 does not display message 311 and message 312. Controller 140 may display a message in message section 308 based on display conditions for other messages. For example, regarding numerical information 102a of three analysis items of WBC, RBC, and HGB, if those three items are not erroneously low values (ALERT L), but if all of those three items are low values (Low), controller 140 prints message 311 prompting further testing but does not print message 312.

As described above, controller 140 controls the print content of analysis results 102. "END REPORT" printed on the end of printed information shows the end of printed sheet 300. Note that memory 142 of controller 140 stores data necessary to output analysis results 102 such as first determination ranges 350 and second determination ranges 360, information 102b indicating the type of the abnormality, and message 311 and message 312.

(Modified Example of Second Determination Range)

FIG. 53 to FIG. 55 illustrates an example where second determination ranges 360 are set to ranges of erroneously low value (ALERT L) within second erroneous ranges 373. However, all of second erroneous ranges 373 may be set to second determination ranges 360, for example. To be more specific, second determination ranges 360 may be set also to ranges of erroneously high value (ALERT H), in addition to ranges of erroneously low value (ALERT L).

FIG. 56 illustrates a printing example where both erroneously low values (ALERT L) and an erroneously high value (ALERT H) are set as second determination ranges 360. In the example of FIG. 50, numerical information 102a is printed for the HGB item corresponding to an erroneously high value (ALERT H). In the example of FIG. 56, on the other hand, the outputting of numerical information 102a is prohibited for the HGB item corresponding to an erroneously high value (ALERT H), and substitute indication 313 is printed instead of numerical information 102a. In FIG. 56, numerical information 102a corresponding to an item being an erroneously low value is substituted for substitute indication 313. "ALERT L" is assigned to an item of erroneously low value as information 315 indicating a second error, and "ALERT H" is assigned to an item of erroneously high value (ALERT H) as information 315 indicating a second error. Thus, it is possible to recognize which of an erroneously low value and erroneously high value numerical information 102a is even when the numerical information is not printed.

(Modified Example of Printing Embodiment)

The example of FIG. 50 and the example of FIG. 56 illustrate examples of substituting numerical information 102a falling within second determination ranges 360 for substitute indication 313 and printing substitute indication 313. However, the configuration may be such that numerical information 102a falling within second determination ranges 360 is not displayed, for example. The example of FIG. 57 illustrates an example where numerical information 102a falling within second determination ranges 360 is not displayed when both erroneously low values and an erroneously high value are set as second determination ranges 360. In FIG. 57, from the content to be printed, controller 140 excludes numerical information 102a falling within second determination ranges 360 together with the item names of the analysis items. Thus, information 102b indicating the type of the abnormality is not printed either. For this reason, in the example of FIG. 57, the analysis items themselves of WBC, HGB, and PLT with numerical information 102a falling within second determination ranges 360 have been excluded from result displaying section 307.

On the other hand, also in the example of FIG. 57, if there is numerical information 102a falling within second determination ranges 360, controller 140 causes message 311 prompting further testing in message section 308 to be printed. In the example of FIG. 57, message 312 recommending immediate action is also printed. The user can recognize there is an error in analysis results 102 by message 311 prompting further testing and message 312 recommending immediate action even in the case where numerical information 102a falling within second determination ranges 360 is deleted together with the analysis items in result displaying section 307.

(Modified Example of Output Rules for Analysis Result on Printed Sheet)

The example of FIG. 51 illustrates an example where in the initial test, controller 140 prohibits the outputting of printed sheet 300 if numerical information 102a is included in first erroneous ranges 372, and causes retest to be performed. However, printed sheet 300 may be outputted in the initial test. In the initial test, if numerical information 102a is included in first erroneous ranges 372, controller 140 may substitute numerical information 102a for substitute indication 313 and output the symbol, or remove numerical information 102a as a not-displayed item from the print content together with the item names of the analysis items.

FIG. 58 illustrates a modified example of output rules for analysis results 102. In a first modification of FIG. 58, controller 140 permits the outputting of numerical information 102a included in normal ranges 371. Controller 140 prohibits the outputting of numerical information 102a outside first determination ranges 350, numerical information 102a within first erroneous ranges 372, numerical information 102a within second erroneous ranges 373, and numerical information 102a in the case of a fractionation error. Controller 140 substitutes numerical information 102a for substitute indication 313 as in FIG. 56, where the outputting of the numerical information is prohibited. In the first modification, controller 140 permits the outputting of information 102b indicating the type of the abnormality, out of analysis results 102.

In the case of a second modification of FIG. 58, controller 140 permits the outputting of numerical information 102a included in normal ranges 371. Controller 140 prohibits the outputting of numerical information 102a outside first determination ranges 350, numerical information 102a within first erroneous ranges 372, numerical information 102a within second erroneous ranges 373, and numerical information 102a in the case of a fractionation error. Controller 140 does not display numerical information 102a on printed sheet 300, where the outputting of the numerical information is prohibited. To be more specific, numerical information 102a not within normal ranges 371 is not printed on printed sheet 300 as in FIG. 57. In the second modification, controller 140 also prohibits the outputting of information 102b indicating the type of the abnormality, out of analysis results 102. Thus, in the second modification, when an analysis item having numerical information 102a outside normal ranges 371 is obtained, all of its item name, numerical information 102a, and information 102b indicating the type of the abnormality are removed from printed sheet 300, and the item itself is not printed.

Additionally, the initial test and the retest are not distinguished in the first modification and the second modification of FIG. 58. To be more specific, in the initial test, if numerical information 102a is included in first erroneous ranges 372, the outputting of numerical information 102a is prohibited and printed sheet 300 is outputted.

(Error Display of Display Unit)

Subsequently, an error display of display unit 131 is described. If analysis results 102 include an abnormal value, controller 140 causes print unit 135 to print information 102b indicating the type of the abnormality as analysis results 102, and if there is an error with the apparatus other than with analysis results 102, the controller causes display unit 131 to display information indicating there is an error. Analysis results 102 are outputted collectively on printed sheet 300, and display unit 131 displays information other than on analysis results 102. Information displayed by display unit 131 includes information on instructions concerning the series of operations illustrated in FIG. 7 to FIG. 48, and on an apparatus error.

To be more specific, display unit 131 displays information indicating there is an error if there is an error with the apparatus other than with analysis results 102. Thus, print unit 135 prints an error with analysis results 102, and display unit 131 displays an apparatus error. An apparatus error is not printed by print unit 135, but is displayed by display unit 131.

Figure 59:
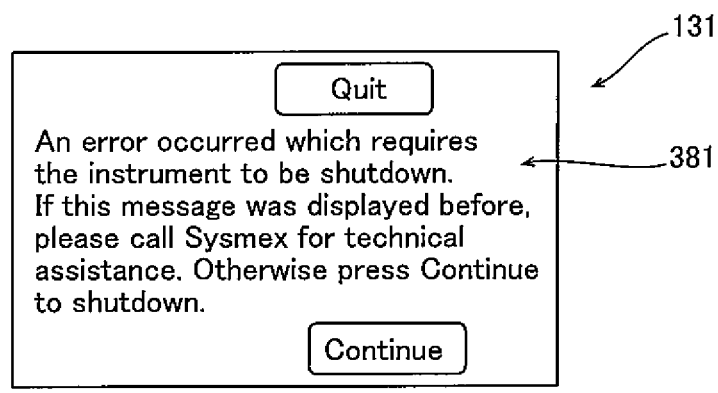
FIG. 59 is a diagram illustrating an example of an error display screen.

Display unit 131 displays information indicating there is an error for at least one of an error with analysis unit 120 and an error with a quality control process of analysis unit 120, for example. In analysis unit 120, when there is an error in e.g. drive mechanism 122, fluid circuit 124, or detector 123, controller 140 causes display unit 131 to display information 381 indicating there is an error as illustrated in FIG. 59. In addition, in the quality control process, for example, controller 140 causes display unit 131 to display information (screen P117) indicating there is an error illustrated in FIG. 30 when the quality control process fails such as when an analysis result of a QC reagent exceeds a reference range set for the QC reagent.

Note that the embodiments disclosed herein should be considered illustrative and non-limited in all respects. The scope of the invention is given by the scope of claims, not by the description of the embodiments described above, and moreover includes all modifications (modified examples) within the meaning and the scope equivalent to the scope of claims.

The invention claimed is:

1. A specimen analyzer comprising:
an analysis unit comprising one or more detectors, which perform measurement of a specimen collected from a subject;
a manual input unit comprising one or more of a touch panel, a keyboard and a mouse, the manual input unit receiving an input of information by manual operation;
an information read unit comprising one or more of a barcode reader, a two-dimensional code reader, an RFID reader and a camera, the information read unit obtaining information by reading an information record section attached to a consumable;
a display; and
a processor programmed to:
cause the display to show a screen with a message prompting a user to input the information on the consumable with the information read unit;
cause the display to shift to a next screen concerning placement or replacement of the consumable in response to an input of the information on the consumable with the information read unit; and
cause the display to not shift to the next screen concerning placement or replacement of the consumable in response to an input of the information on the consumable with the manual input unit.

2. The specimen analyzer according to claim 1, wherein the processor is programmed to perform operations further comprising causing the display to display a message based on the inputted information.

3. The specimen analyzer according to claim 2, wherein the processor is programmed to perform operations further comprising acquiring an expiration date of the consumable based on the information on the consumable, and causing the display to display a message based on the expiration date.

4. The specimen analyzer according to claim 2, wherein the consumable comprises a disposable consumable, and reading an information record section of the disposable consumable after use of the disposable consumable, causes the processor to perform operations comprising not permitting use of the consumable, and causing the display to display an error message.

5. The specimen analyzer according to claim 2, wherein the processor is programmed to perform operations further comprising acquiring whether the consumable is usable based on the information on the consumable, and causing the display to display an error message when the consumable is unusable.

6. The specimen analyzer according to claim 1, wherein the information read unit receives an input of the information on each consumable by reading the information record section provided in the consumable.

7. The specimen analyzer according to claim 1, further comprising
a communication unit comprising a network interface, the network interface capable of communicating with an external server, wherein
the processor is programmed to perform operations further comprising causing the communication unit to transmit the information on the consumable inputted with the information read unit to the server.

8. The specimen analyzer according to claim 7, wherein the processor is programmed to perform operations further comprising not permitting the input of the information on the consumable with the information read unit when communicating with the server via the communication unit is not possible.

9. The specimen analyzer according to claim 7, wherein the processor is programmed to perform operations further comprising permitting use of the consumable if the information on the consumable inputted with the information read unit is registered in the server.

10. The specimen analyzer according to claim 9, wherein the processor is programmed to perform operations further comprising permitting use of the consumable if a lot number included in the information on the consumable is registered in the server.

11. The specimen analyzer according to claim 1, wherein the processor is programmed to perform operations further comprising not shifting to a next process concerning placement or replacement of the consumable unless the information on the consumable is input with the information read unit.

12. The specimen analyzer according to claim 1, wherein the information on the consumable includes at least one of a type, an expiration date, a lot number, and a serial number of the consumable.

13. The specimen analyzer according to claim 1, wherein the analysis unit analyzes the specimen by use of the consumable.

14. The specimen analyzer according to claim 1, wherein the specimen comprises blood, and
the analysis unit analyzes the number of blood cells and a concentration of a component contained in the blood.

15. The specimen analyzer according to claim 1, wherein the consumable comprises at least one of: a reagent used for analysis, a quality control sample, and a cleaning liquid.

16. A specimen analysis method comprising:
inputting information on a consumable by causing an information read unit to read an information record section attached to the consumable, and placing the consumable or replacing an old consumable with the consumable;
analyzing a specimen collected from a subject;
displaying a screen with a message prompting a user to input the information on the consumable with the information read unit;
shifting to a next screen concerning placement or replacement of the consumable in response to an input of the information on the consumable with the information read unit; and
continuously displaying the screen with the message in response to an input of the information on the consumable with an manual input unit.

* * * * *